United States Patent
Roth

(10) Patent No.: US 9,055,924 B2
(45) Date of Patent: Jun. 16, 2015

(54) TYMPANIC PROBE COVER

(71) Applicant: Jason Roth, Boca Raton, FL (US)

(72) Inventor: Jason Roth, Boca Raton, FL (US)

(73) Assignee: ARC Devices Limited, Galway (IE)

( * ) Notice: Subject to any disclaimer, the term of this patent is extended or adjusted under 35 U.S.C. 154(b) by 0 days.

(21) Appl. No.: 14/074,886

(22) Filed: Nov. 8, 2013

(65) Prior Publication Data

US 2014/0088434 A1 Mar. 27, 2014

Related U.S. Application Data

(63) Continuation of application No. 13/624,874, filed on Sep. 21, 2012, now Pat. No. 8,452,382.

(51) Int. Cl.
| | |
|---|---|
| *A61B 5/00* | (2006.01) |
| *A61B 5/01* | (2006.01) |
| *G01J 5/02* | (2006.01) |
| *G01J 5/08* | (2006.01) |
| *G01J 5/00* | (2006.01) |

(52) U.S. Cl.
CPC ............ *A61B 5/6817* (2013.01); *A61B 5/6887* (2013.01); *A61B 5/01* (2013.01); *A61B 2562/0233* (2013.01); *A61B 2562/0271* (2013.01); *G01J 5/025* (2013.01); *G01J 5/0809* (2013.01); *G01J 5/0025* (2013.01); *A61B 5/0086* (2013.01); *A61B 5/0075* (2013.01); *A61B 5/015* (2013.01)

(58) Field of Classification Search
CPC . G01J 5/021; G01J 5/0893; G01J 2005/0048; G01J 5/0815; G01K 13/002

USPC .................. 374/158, 209, 163, 121; 600/184
See application file for complete search history.

(56) References Cited

U.S. PATENT DOCUMENTS

| | | | | |
|---|---|---|---|---|
| 4,155,226 | A * | 5/1979 | Altman ........................... | 62/467 |
| 4,322,012 | A | 3/1982 | Conti | |
| 4,602,642 | A | 7/1986 | O'Hara et al. | |
| 5,368,038 | A | 11/1994 | Fraden | |
| 5,743,644 | A | 4/1998 | Kobayashi | |
| 7,572,056 | B2 | 8/2009 | Lane | |
| 7,766,485 | B2 * | 8/2010 | Momiuchi et al. ............. | 353/62 |
| 7,787,938 | B2 | 8/2010 | Pompei | |
| 8,136,986 | B2 * | 3/2012 | Lane et al. .................... | 374/158 |
| 8,517,603 | B2 | 8/2013 | Fraden | |
| 2001/0017880 | A1 * | 8/2001 | Beerwerth et al. ............ | 374/158 |
| 2004/0013162 | A1 | 1/2004 | Beerwerth | |
| 2004/0047392 | A1 * | 3/2004 | Wu et al. ....................... | 374/121 |
| 2004/0057493 | A1 * | 3/2004 | Ishikawa et al. ............. | 374/120 |
| 2005/0207470 | A1 * | 9/2005 | Bennett et al. ................. | 374/130 |
| 2007/0183475 | A1 | 8/2007 | Hutcherson | |
| 2008/0175301 | A1 | 7/2008 | Chen | |

(Continued)

FOREIGN PATENT DOCUMENTS

| | | | | |
|---|---|---|---|---|
| DE | 4040812 | A * | 6/1992 | |
| JP | 61231422 | A * | 10/1986 | |
| JP | 09257770 | A * | 10/1997 | |

*Primary Examiner* — Gail Kaplan Verbitsky
(74) *Attorney, Agent, or Firm* — Michael G. Smith, Esq.

(57) ABSTRACT

A digital non-contact tympanic thermometer has a tympanic probe with an IR sensor at the end of the probe in which the digital non-contact tympanic thermometer can be converted to a digital non-contact non-tympanic thermometer for non-tympanic surfaces by placement of removeable probe cover over the tympanic cover in which the probe cover includes a parabolic condenser at the tip of the probe cover that increases gathering of incoming infrared energy.

16 Claims, 36 Drawing Sheets

(56) References Cited

U.S. PATENT DOCUMENTS

| | | |
|---|---|---|
| 2009/0172591 A1 | 7/2009 | Pomper |
| 2009/0182526 A1* | 7/2009 | Quinn et al. .................. 702/131 |
| 2011/0228811 A1 | 9/2011 | Fraden |
| 2012/0130251 A1 | 5/2012 | Huff |
| 2013/0245488 A1* | 9/2013 | Quinn et al. .................. 600/549 |
| 2013/0245489 A1* | 9/2013 | Mullin et al. .................. 600/549 |
| 2014/0046192 A1* | 2/2014 | Mullin et al. .................. 600/474 |

* cited by examiner

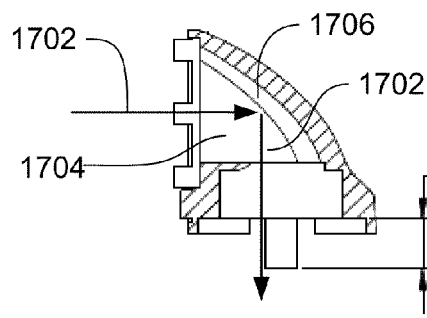
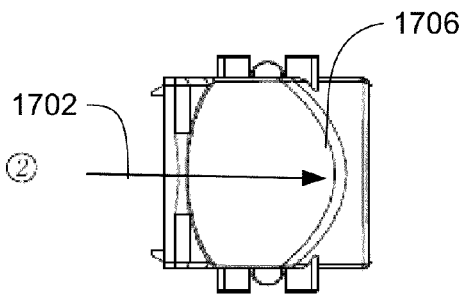
FIG. 17          FIG. 18
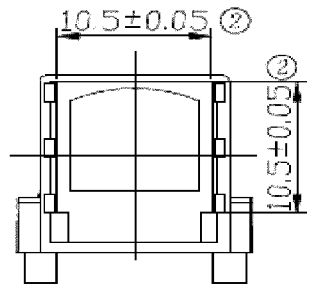
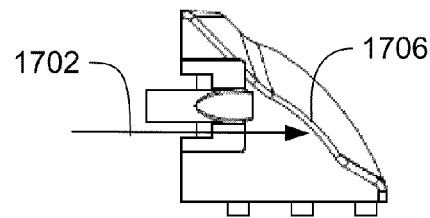
FIG. 19          FIG. 20
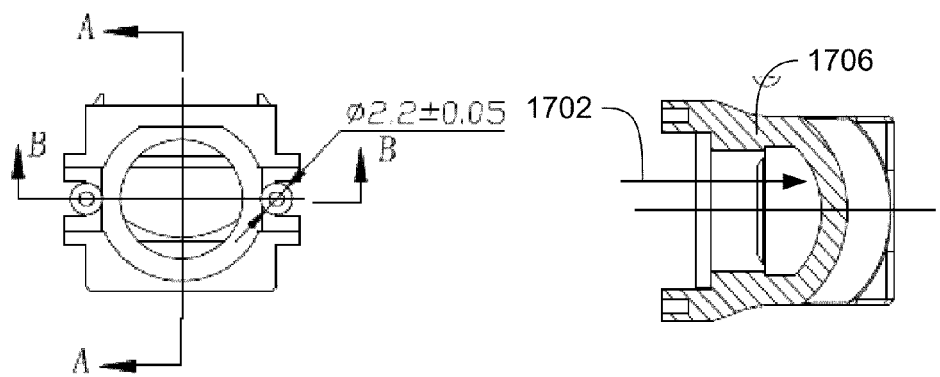
FIG. 21          FIG. 22
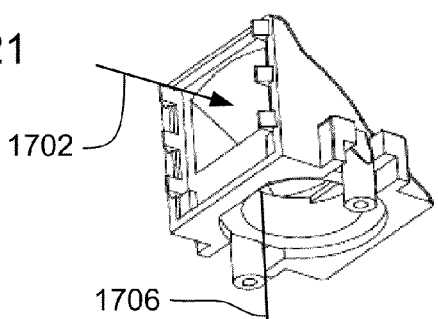
FIG. 23

3900

| Non-Contact Thermometer | Mobile Device | Cloud |
|---|---|---|
| connect to Mobile Device via USB 3902 | download calibration App 3910 | |
| recognize Mobile Device 3904 | recognize Non-Contact Thermometer 3912 | |
| enter F4 mode 3906 | start execution of calibration App 3914 | |
| send configuation data to Mobile Device 3908 | | |
| | calibration App receive configuration data from Non-Contact Thermometer 3916 | |
| | calibration App presents navigation menus and receives selection of the Non-Contact Thermometer 3918 | |
| | generate diagnostic instructions for the selected non-Contact Thermometer 3920 | |
| | transmit the Generated diagnostic instructions to the selected Non-Contact Thermometer 3922 | |
| receive the Generated diagnostic instructions for the Non-Contact Thermometer 3924 | | |
| perform the Generated diagnostic instructions 3926 | | |
| transmit the results of the Performed diagnostic instructions to the Mobile Device 3928 | | |
| | receive the results of the Performed diagnostic instructions from the Non-Contact Thermometer 3930 | |
| | Generate calibration instructions for the selected Non-Contact Thermometer 3932 | |
| | transmit the Generated calibration instructions to the selected Non-Contact Thermometer 3934 | |

| Non-Contact Thermometer | Mobile Device | Cloud |
|---|---|---|
| receive the Generated calibration instructions for the Non-Contact Thermometer 3936 | | |
| perform the Generated calibration instructions 3938 | | |
| transmit the results of the Performed calibration instructions to the Mobile Device 3940 | | |
| | receive the results of the Performed calibration instructions from the Non-Contact Thermometer 3942 | |
| | store the results of the performed calibration instructions and the GPS location of the mobile device and the date/time 3944 | |
| | transmit through the Cloud a notice of the completed calibration and the date/time to a compliance office 3946 | |
| | | receive notice of the completed calibration and the date/time 3948 |

FIG. 40

TYMPANIC PROBE COVER

FIELD

This disclosure relates generally to digital thermometers, and more particularly to tympanic temperature measurement by an infrared sensor and by a contact sensor.

BACKGROUND

Conventional non-contact digital thermometers do not provide temperature measurement of both tympanic aspects and forehead aspects of a subject.

BRIEF DESCRIPTION

In one aspect, a tympanic probe cover includes a probe cover body that has a geometry to fit an ear canal, the probe cover body having an upper free frontal end, the upper free frontal end of the probe cover body having a tip, the probe cover body does not include any further structures, a probe cover window at the upper free frontal end of the probe cover body that closes off the upper free frontal end of the probe cover body, probe cover window being attached to the probe cover body by a weaving, the probe cover window being transparent to infrared radiation at a radiation range relevant for human temperature measurement, a probe cover base that is attached at a bottom of the probe cover body that is an opposite end of the upper free frontal end of the probe cover body and that also includes an infrared parabolic condenser inside the tip of the upper free frontal end of the probe cover body.

In another aspect, a tympanic probe cover includes a probe cover body that has a geometry to fit an ear canal, the probe cover body having an upper free frontal end, the probe cover body does not include any further structures, a probe cover window at the upper free frontal end of the probe cover body that closes off the upper free frontal end of the probe cover body, the probe cover window being transparent to infrared radiation at a radiation range relevant for human temperature measurement, a probe cover base that is attached at a bottom of the probe cover body that is an opposite end of the upper free frontal end of the probe cover body and also includes an infrared parabolic condenser inside the probe cover body.

In yet another aspect, a tympanic probe cover includes a probe cover body that has a geometry to fit an ear canal, the probe cover body having an upper free frontal end, the probe cover body does not include any further structures, a probe cover window at the upper free frontal end of the probe cover body that closes off the upper free frontal end of the probe cover body, the probe cover window being transparent to infrared radiation at a radiation range relevant for human temperature measurement and also includes an infrared parabolic condenser inside the probe cover body.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 17-23 are block diagrams of a sensor collector to guide electromagnetic energy to measure temperature, according to an implementation;

FIG. 39-40 is a series of sequence diagrams of the interaction between a mobile device and a hand-held medical device, according to an implementation;

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into four sections. In the first section, apparatus of a tympanic probe and a tympanic probe cover are described. In the second section, an overview of implementations is described. In the third section, apparatus of implementations are described. In the fourth section, implementations of methods are described. In the fifth section, a hardware and operating environment in conjunction with which implementations may be practiced are described. Finally, in the sixth section, a conclusion of the detailed description is provided.

Tympanic Probe

The primary purpose of the tympanic probes and the tympanic probe covers described in FIG. 1-8 is to convert a digital tympanic contact-thermometer to a digital non-contact non-tympanic thermometer by placing a removeable probe cover over a tympanic probe of the digital tympanic contact-thermometer, in which the removable probe cover includes a parabolic condenser at the tip of the removable probe cover that increases gathering of incoming infrared energy and the tympanic probe has an IR sensor at the end of the probe.

Figure 1:
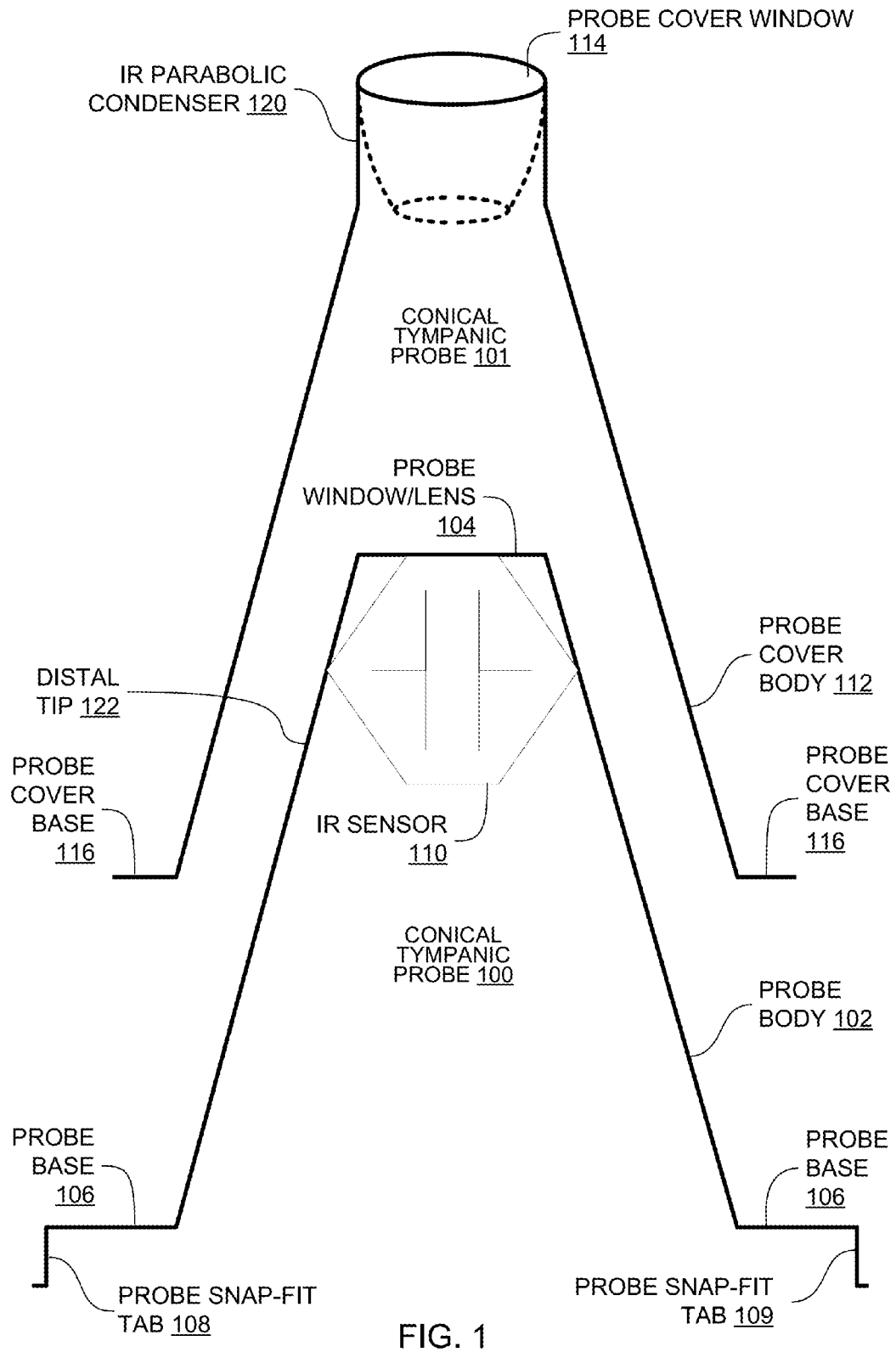
FIG. 1 is a side view cross section diagram of a conical tympanic probe having an IR sensor, snap-fit tabs on a base and a symmetrical conical tympanic probe cover having a parabolic condenser according to an implementation.

FIG. 1 is a side view cross section diagram of a conical tympanic probe 100 having an IR sensor, snap-fit tabs on a base and a symmetrical conical tympanic probe cover 101 having a parabolic condenser according to an implementation.

The tympanic probe 100 includes a probe body 102 that has a geometry to fit an ear canal (the ear canal not shown) and a probe window/lens 104 that is transparent to infrared radiation. The probe body 102 does not include any additional structures, such as padding around the probe body 102, in order to prevent measurement errors by the infrared radiation thermometer because the distance between the IR sensor and the tympanic membrane surface that is imposed by the probe body 102 provides a consistent and predictable bias in the thermal energy received by the IR sensor. A probe base 106 is attached at the bottom of the probe body 102 and probe snap-fit tabs 108 and 109 are attached to the probe base 106. The probe window/lens 104 is either a lens that focuses infrared energy on the infrared sensor of the thermometer or the probe window/lens 104 is window that passes through substantially all incoming infrared energy.

At an upper free frontal end, the tympanic probe 100 is closed off by an infrared probe window/lens 104 that is formed of a thin film transparent to infrared radiation in the radiation range relevant for temperature measurement. In FIG. 1, the probe window/lens 104 is affixed to the probe body 102 as a separate member, as by weaving. Where the probe body 102 is made of foamed plastic only, the film of the probe window/lens 104 is formed out of the foamed plastic by hot stamping or pressing. Adjacent to the infrared probe window/lens 104 and inside the upper free frontal end, the tympanic probe 100 includes an infrared sensor 110.

The tympanic probe cover 101 includes a probe cover body 112 shaped to fit an ear canal (not shown) and a probe cover window 114 that is transparent to infrared radiation. The probe cover body 112 does not include any additional structures, such as padding around the probe cover body 112, in order to prevent measurement errors by the infrared radiation thermometer because the distance between the IR sensor and the tympanic membrane surface that is imposed by the probe cover body 112 provides a consistent and predictable bias in the thermal energy received by the IR sensor. A probe cover base 116 is attached at the bottom of the probe cover body 112. At an upper free frontal end, the tympanic probe cover 101 is closed off by an infrared probe cover window 114 that is formed of a thin film that is transparent to infrared radiation in the radiation range relevant for temperature measurement. In FIG. 1, the probe cover window 114 is affixed to the probe cover body 112 as a separate member, such as by weaving. Adjacent to the infrared probe cover window 114 and inside a tip of the upper free frontal end of the tympanic probe cover 101, the tympanic probe cover 101 includes an infrared parabolic funnel condenser 120. The parabolic funnel geometry of the condenser is notably superior at gathering infrared energy from a wide angle. The parabolic funnel geometry gathers infrared energy from a wider angle than conventional straight-line waveguides and reflectors. The parabolic funnel geometry of the infrared parabolic funnel condenser 120 is a three-dimensional parabolic funnel, not a two-dimensional curved reflector or waveguide, which gather infrared energy from a much wider angle than curved reflectors and waveguides of less incidental angles than the three-dimensional parabolic funnel geometry of the infrared parabolic funnel condenser 120. The superior geometry of the infrared parabolic funnel condenser 120 is implemented either using generally similar dimensions of conventional reflectors which would provide higher signal strength by the IR sensor 110, which is implemented with a less expensive IR sensor 110 having lower sensitivity than conventional IR sensors, or the infrared parabolic funnel condenser 120 is implemented using generally similar dimensions of conventional reflectors which would provide higher signal strength by the IR sensor 110, which is implemented with a conventional priced IR sensor having similar sensitivity to conventional IR sensors, which provides a IR detection of greater certainty.

Figure 2:
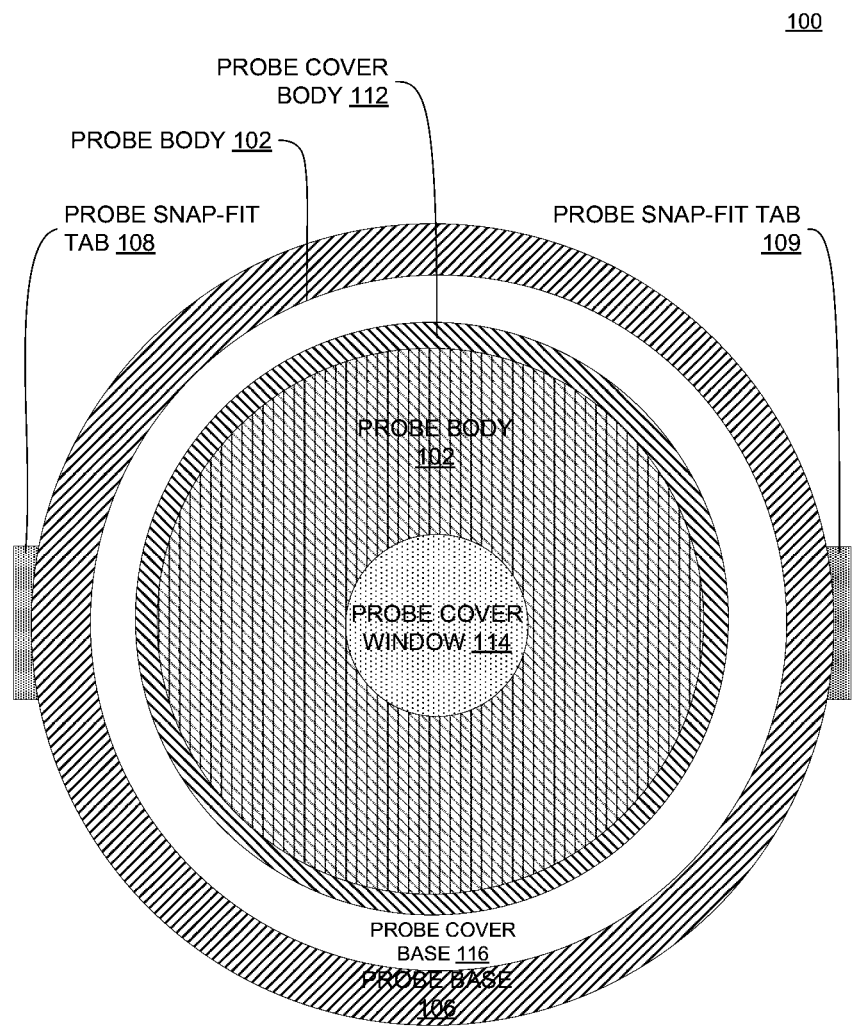
FIG. 2 is a top view diagram of a conical tympanic probe having an IR sensor, snap-fit tabs on a base and a symmetrical conical tympanic probe cover having a parabolic condenser according to an implementation.

FIG. 2 is a top view cross section diagram of a conical tympanic probe 100 having an IR sensor, snap-fit tabs on a base and a symmetrical conical tympanic probe cover 101 having a parabolic condenser according to an implementation.

Figure 3:
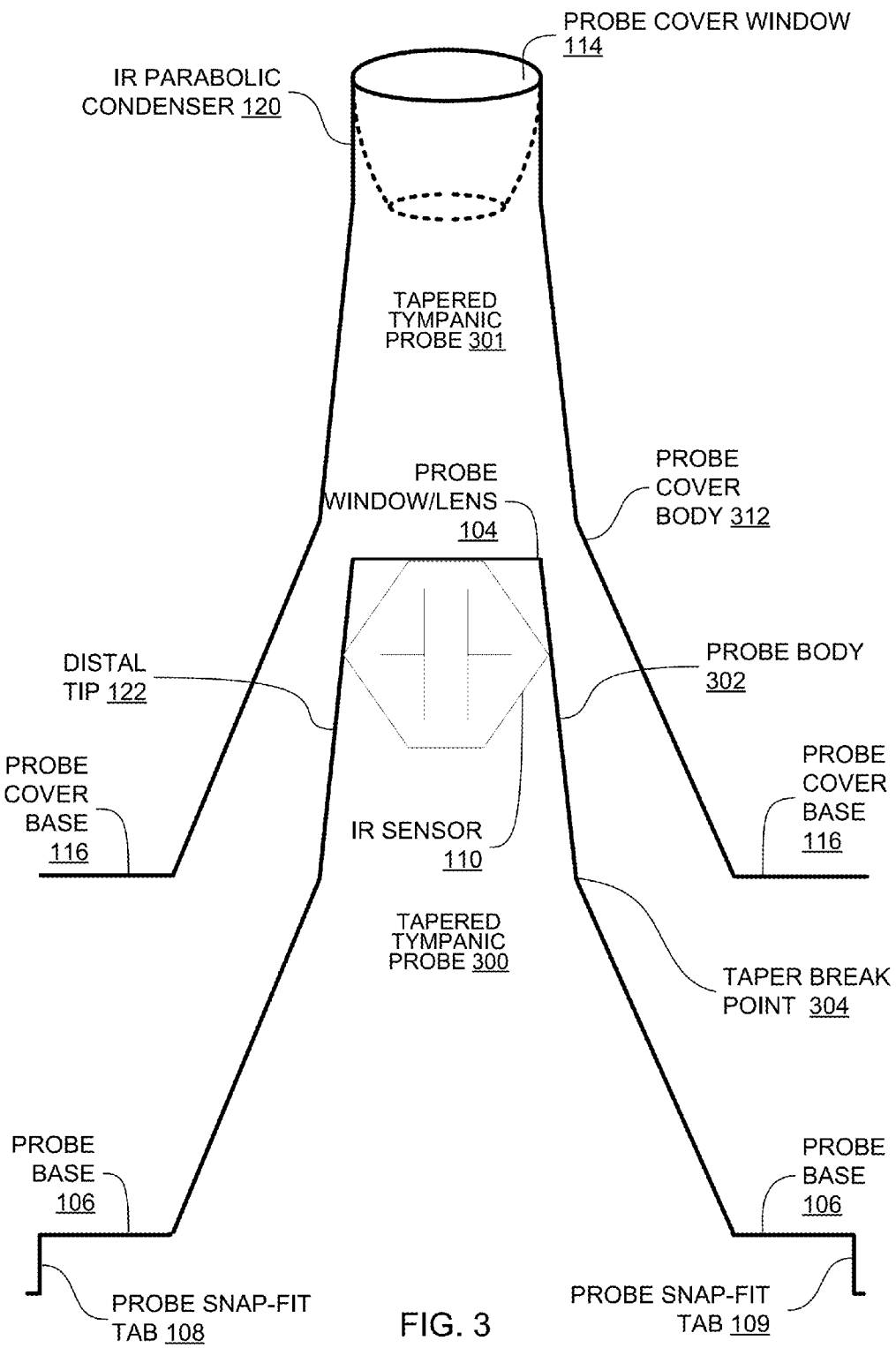
FIG. 3 is a side view cross section diagram of a tapered tympanic probe having snap-fit tabs on a base, according to an implementation.

FIG. 3 is a side view cross section diagram of a tapered tympanic probe 300 having an IR sensor, snap-fit tabs on a base and a symmetrical tapered tympanic probe cover 301 having a parabolic condenser according to an implementation.

The tympanic probe 300 includes a probe body 302 shaped to fit an ear canal (not shown) and a window/lens 104 that is transparent to infrared radiation. The probe body 302 does not include any additional structures, such as padding around the body 302, in order to prevent measurement errors by the infrared radiation thermometer because the distance between the IR sensor and the tympanic membrane surface that is imposed by the probe body 302 provides a consistent and predictable bias in the thermal energy received by the IR sensor. A probe base 106 is attached at the bottom of the probe body 302 and probe snap-fit tabs 108 and 109 are attached to the base 106. The tympanic probe 300 is tapered more narrowly at the top of the tympanic probe 300 than at the bottom of the tympanic probe 300 between the probe taper break point 304. The probe body 302 extends slightly conically towards its free end where the probe window/lens 104 is integrally formed, having a stepped tapered end portion corresponding at its end to the outside diameter of an infrared waveguide. By virtue of this tapered end portion, the clinical thermometer is suitable for use on both children who have a relatively narrow ear canal and adults who have a wider ear canal. As shown in FIG. 3, the installed tympanic probe 100 includes a thin-walled tubular probe body 102 tapering conically towards its free end and made from a plastic material. In this embodiment, the probe body 302 is dispensed with entirely, the tympanic probe 100 then being only comprised of foamed plastic material or forming a honeycombed air chamber structure.

A tympanic probe cover 301 includes a probe cover body 312 shaped to fit an ear canal (not shown) and a probe cover window 114 that is transparent to infrared radiation. The probe cover body 312 does not include any additional structures, such as padding around the probe cover body 312, in order to prevent measurement errors by the infrared radiation thermometer because the distance between the IR sensor and the tympanic membrane surface that is imposed by the probe cover body 312 provides a consistent and predictable bias in the thermal energy received by the IR sensor. A probe cover base 116 is attached at the bottom of the probe cover body 312. At an upper free frontal end, the tympanic probe cover 301 is closed off by an infrared probe cover window 114 that is formed of a thin film that is transparent to infrared radiation in the radiation range relevant for temperature measurement. In FIG. 1, the probe cover window 114 is affixed to the probe cover body 312 as a separate member, such as by weaving. Adjacent to the infrared probe cover window 114 and inside a tip of the upper free frontal end of the tympanic probe cover 301, the tympanic probe cover 301 includes an infrared parabolic funnel condenser 120.

Figure 4:
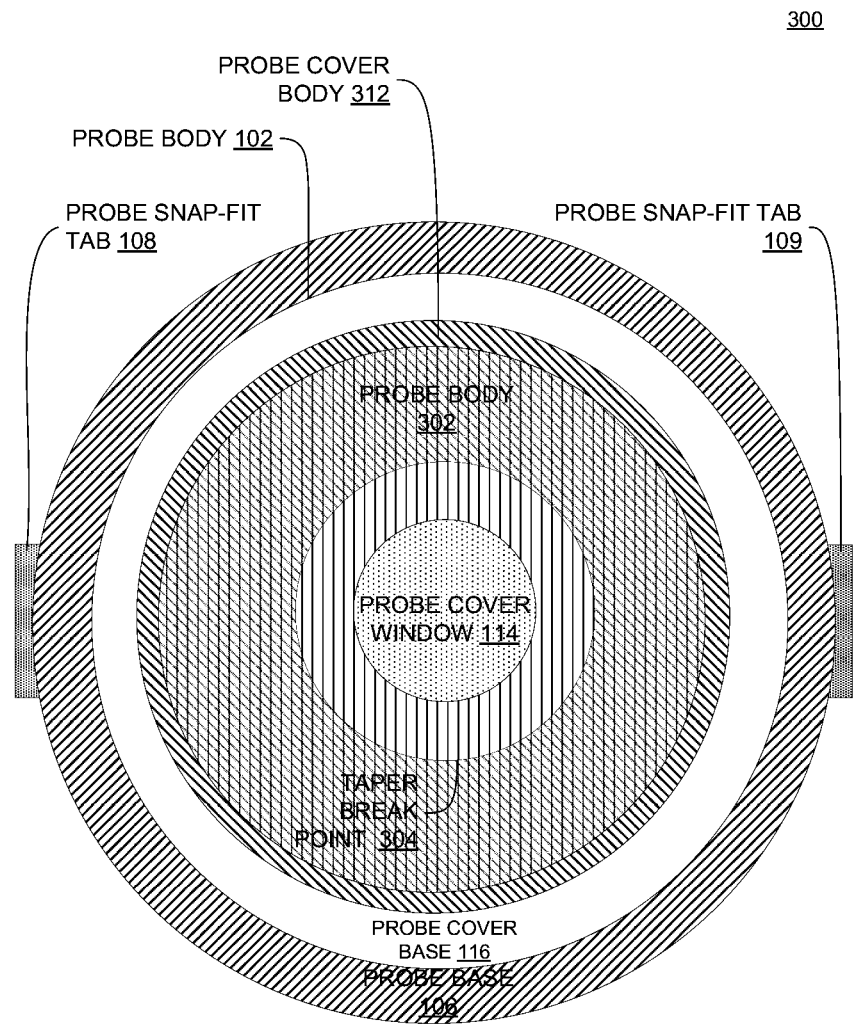
FIG. 4 is a top view block diagram of a tapered tympanic probe having snap-fit tabs on a base, according to an implementation.

FIG. 4 is a top view block diagram of a tapered tympanic probe 300 having snap-fit tabs on a base, according to an implementation.

Figure 5:
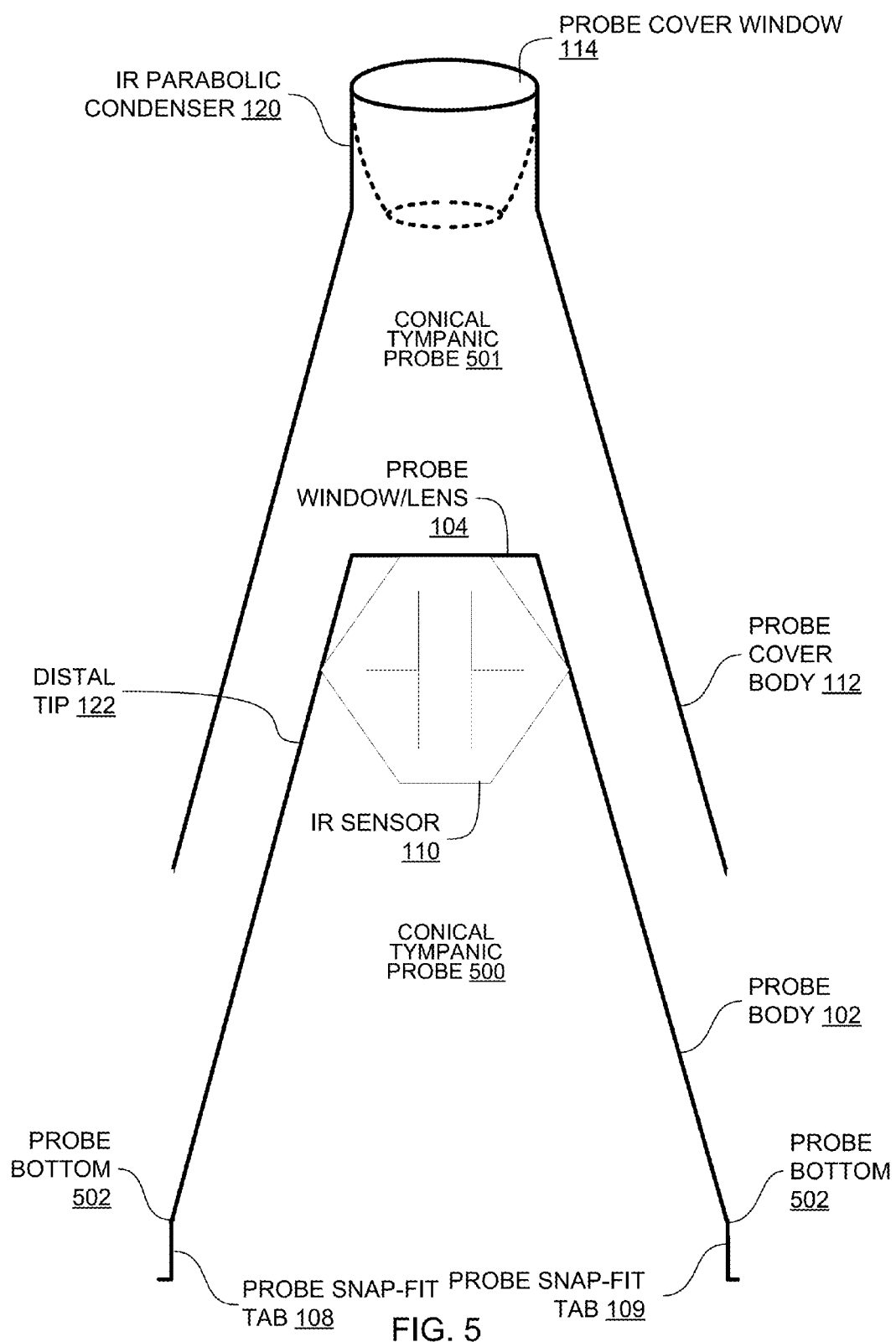
FIG. 5 is a side view cross section diagram of a conical tympanic probe having snap-fit tabs on a bottom end, according to an implementation.

FIG. 5 is a side view cross section diagram of a conical tympanic probe 500 having snap-fit tabs on a bottom end, according to an implementation. The tympanic probe 500 includes a probe body 102 shaped to fit an ear canal (not shown) and a probe window/lens 104 that is transparent to infrared radiation. The probe body 102 does not include any additional structures, such as padding around the probe body 102, in order to prevent measurement errors by the infrared radiation thermometer because the distance between the IR sensor and the tympanic membrane surface that is imposed by the probe body 102 provides a consistent and predictable bias in thermal energy received by the IR sensor. The probe body 102 has a probe bottom 502 and probe snap-fit tabs 108 and 109 are attached to the probe bottom 502.

A tympanic probe cover 501 includes a probe cover body 112 shaped to fit an ear canal (not shown) and a probe cover window 114 that is transparent to infrared radiation. The probe cover body 112 does not include any additional structures, such as padding around the probe cover body 112, in order to prevent measurement errors by the infrared radiation thermometer because the distance between the IR sensor and the tympanic membrane surface that is imposed by the probe cover body 112 provides a consistent and predictable bias in the thermal energy received by the IR sensor. At an upper free frontal end, the tympanic probe cover 501 is closed off by an infrared probe cover window 114 that is formed of a thin film that is transparent to infrared radiation in the radiation range relevant for temperature measurement. In FIG. 5, the probe cover window 114 is affixed to the probe cover body 112 as a separate member, such as by weaving. Adjacent to the infrared probe cover window 114 and inside a tip of the upper free frontal end of the tympanic probe cover 501, the tympanic probe cover 501 includes an infrared parabolic funnel condenser 120.

Figure 6:
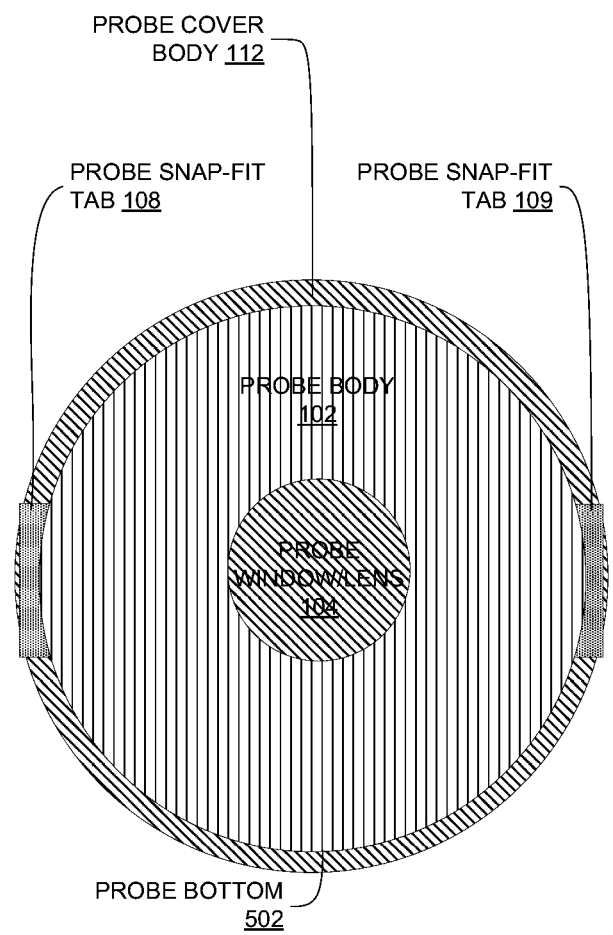
FIG. 6 is a top view block diagram of a conical tympanic probe having snap-fit tabs on a bottom end, according to an implementation.

FIG. 6 is a top view block diagram of a conical tympanic probe 500 having snap-fit tabs on a bottom end, according to an implementation.

Figure 7:
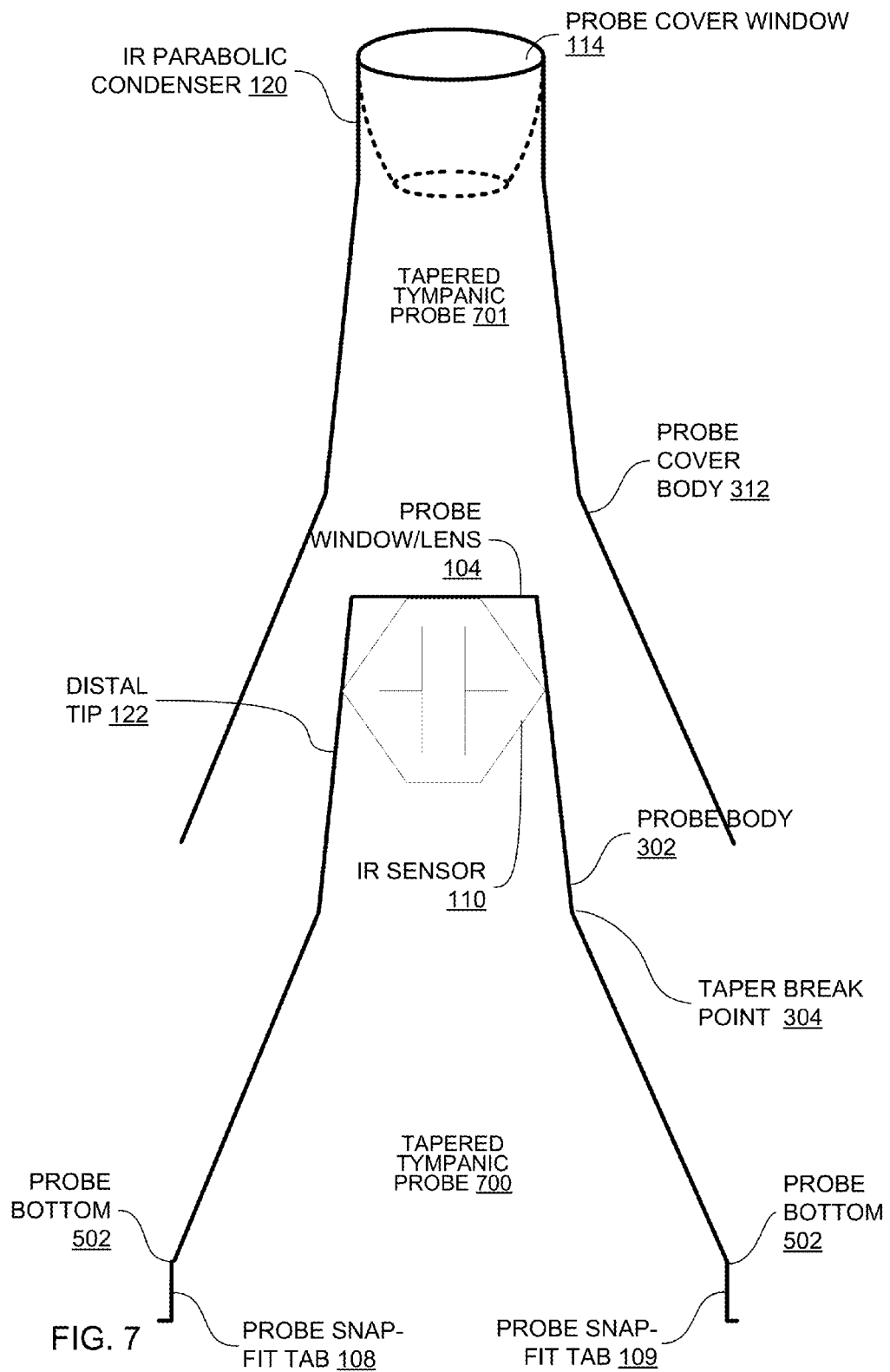
FIG. 7 is a side view cross section diagram of a tapered tympanic probe having snap-fit tabs on a bottom end, according to an implementation.

FIG. 7 is a side view cross section diagram of a tapered tympanic probe 700 having snap-fit tabs on a bottom end, according to an implementation. The tympanic probe 700 includes a probe body 102 shaped to fit an ear canal (not shown) and a window/lens 104 that is transparent to infrared radiation. The probe body 102 does not include any additional structures, such as padding around the probe body 102, in order to prevent measurement errors by the infrared radiation thermometer because the distance between the IR sensor and the tympanic membrane surface that is imposed by the probe body 102 provides a consistent and predictable bias in thermal energy received by the IR sensor. The probe body 102 has a probe bottom 502 and probe snap-fit tabs 108 and 109 are attached to the probe bottom 502. The tympanic probe 700 is tapered more narrowly at the top of the tympanic probe 300 than at the bottom of the tympanic probe 300 between the probe taper break point 304.

Figure 8:
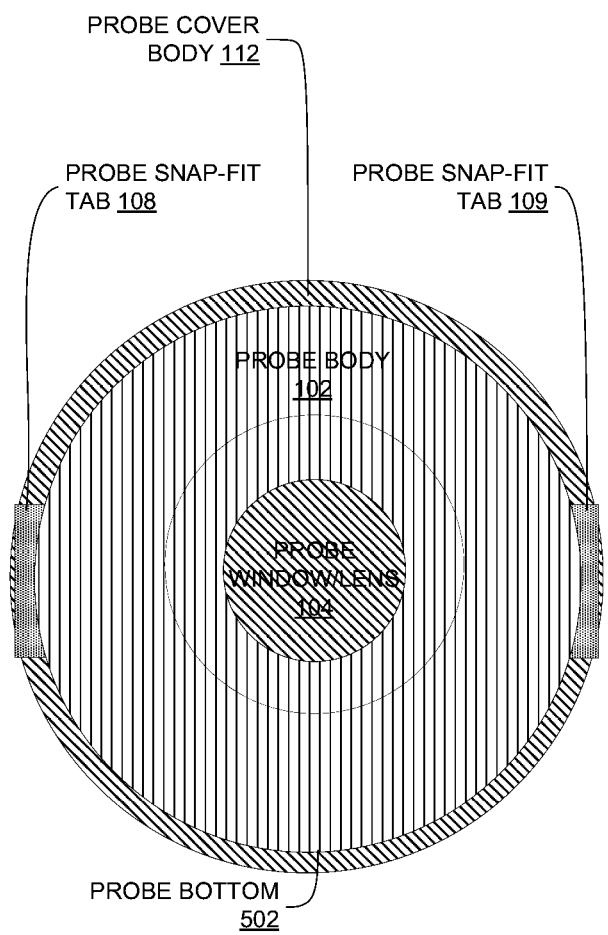
FIG. 8 is a top view block diagram of a tapered tympanic probe having snap-fit tabs on a bottom end, according to an implementation.

FIG. 8 is a top view block diagram of a tapered tympanic probe 700 having snap-fit tabs on a bottom end, according to an implementation.

In some implementations of FIG. 1-8, the conical tympanic probe 100, the tapered tympanic probe 300, the conical tympanic probe 500 and the tapered tympanic probe 700, the tapered tympanic probe 300, the conical tympanic probe 500 and the tapered tympanic probe 700 is made from a stainless steel or other similar thermally conductive material and includes at least one temperature sensing element (not shown), such as a thermocouple or a thermistor, which is housed within a distal tip 122 thereof. The conical tympanic probe 100, the tapered tympanic probe 300, the conical tympanic probe 500 and the tapered tympanic probe 700 can also include a resistive or other heating element (not shown), also preferably housed in the distal tip 122 thereof, which produces pre-heating of the probe in order to acclimate same prior to any temperature measurement in order to hasten the overall measurement time.

Apparatus Implementations

In this section, particular apparatus of implementations are described by reference to a series of diagrams.

Figure 9:
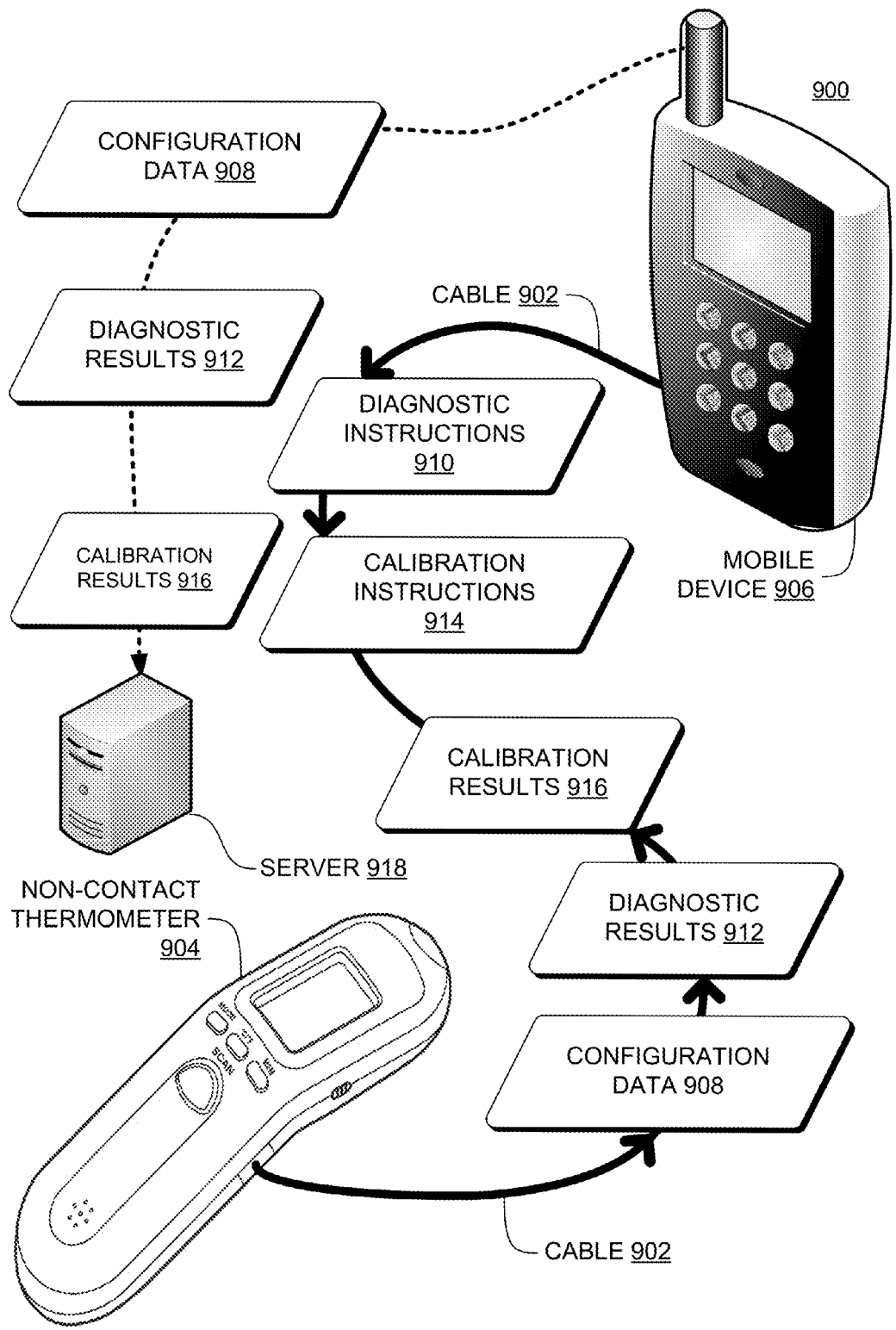
FIG. 9 is a block diagram of an apparatus to manage diagnostics and calibration of a hand-held medical device by a mobile device, according to an implementation.

FIG. 9 is a block diagram of an apparatus 900 to manage diagnostics and calibration of a hand-held medical device by a mobile device, according to an implementation. System 900 provides a convenient means to perform diagnostics and calibration of a hand-held medical device.

After a hand-held medical device 904 is connected to a mobile device 906 through a cable 902 or a wireless connection, configuration data 908 is transmitted from the hand-held medical device 904 through the cable 902 and to the mobile device 906. Examples of the hand-held medical device 904 are the non-contact thermometers as described in FIG. 11-16. The configuration data 908 describes and represents the hardware characteristics and functional capabilities of the hand-held medical device 904. The mobile device 906 generates diagnostic instructions 910 from the configuration data 908 and transmits the diagnostic instructions 910 through the cable 902 to the hand-held medical device 904. The hand-held medical device 904 performs or executes the diagnostic instructions 910 from which diagnostic results 912 are generated and transmitted through the cable 902 to the mobile device 906.

The mobile device 906 generates calibration instructions 914 from the configuration data 908 and transmits the calibration instructions 914 through the cable 902 to the hand-held medical device 904. The hand-held medical device 904 performs or executes the calibration instructions 914 from which calibration results 916 are generated and transmitted through the cable 902 to the mobile device 906. In some implementations, the mobile device 906 generates a notice of the completed calibration in reference to the date/time and the calibration results 916 and transmits the notice of the completed calibration to a server 918 of a compliance office. In some implementations, the mobile device 906 transmits the configuration data 908, the diagnostic results 912 and/or the calibration results 916 to the server 918 of the compliance office.

Figure 10:
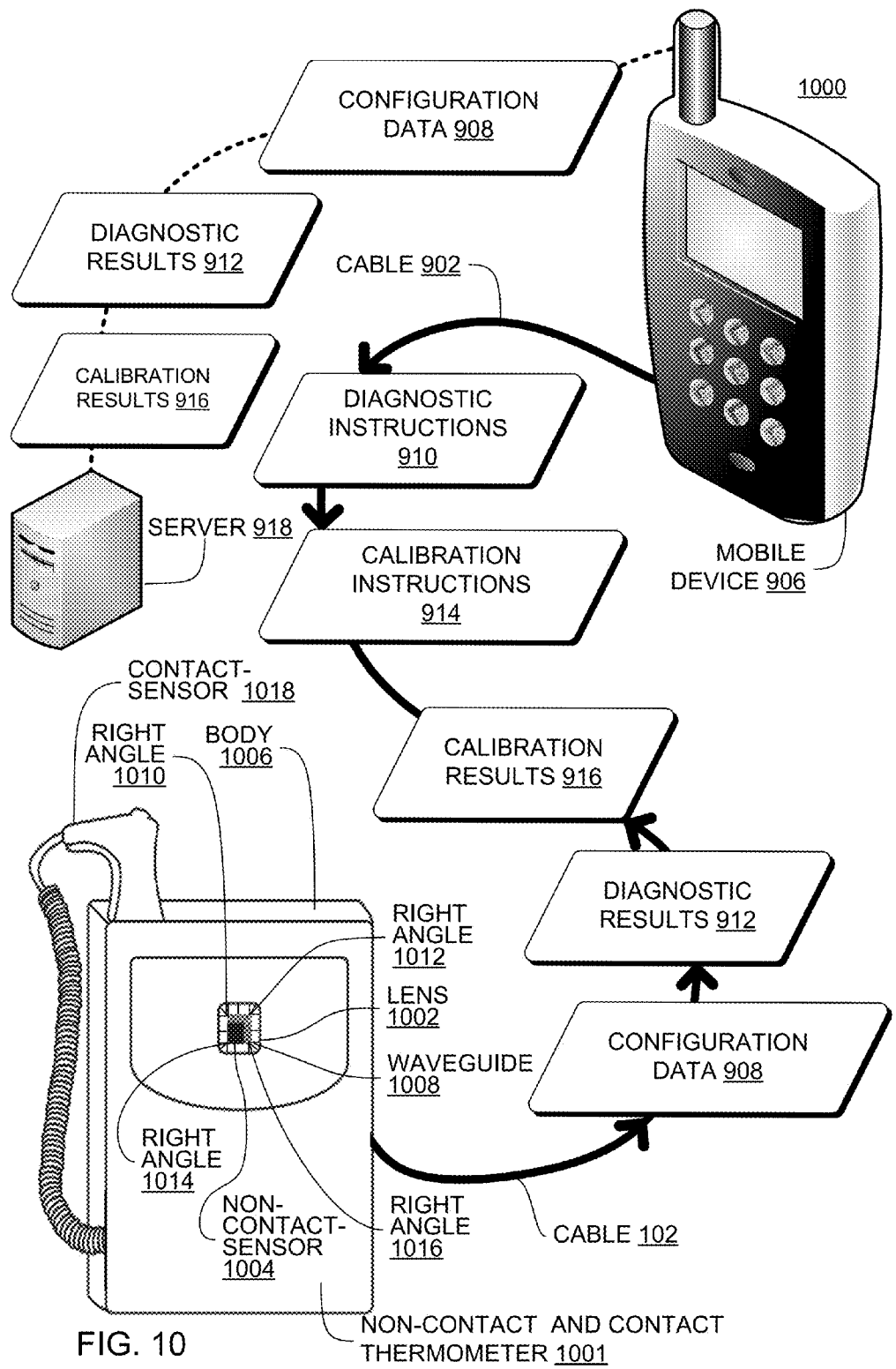
FIG. 10 is a block diagram of an apparatus to manage diagnostics and calibration of a non-contact and contact thermometer by a mobile device, according to an implementation.

FIG. 10 is a block diagram of an apparatus 1000 to manage diagnostics and calibration of a non-contact and contact thermometer by a mobile device, according to an implementation. System 1000 provides a convenient means to perform diagnostics and calibration of a non-contact and contact thermometer 1001. The non-contact and contact thermometer 1001 is handheld and battery powered for intermittent measurement and monitoring of human or animal body temperature of people of all ages. The non-contact and contact thermometer 1001 measures both infrared energy emitted from the skin surface of the human or animal and direct body temperature.

The non-contact and contact thermometer 1001 includes a lens 1002 of the non-contact sensor 1004, the lens 1002 being mounted on the exterior of the body 1006 of the non-contact and contact thermometer 1001. The non-contact sensor 1004 behind the lens 1002 detects temperature in response to remote sensing of a surface a human or animal. A right-angled waveguide 1008 is positioned in proximity to the non-contact sensor 1004. The right-angled waveguide 1008 includes at least one flat planar surface and right angles 1010, 1012, 1014 and 1016. The non-contact and contact thermometer 1001 also includes the contact sensor 1018 that is mounted on the exterior of the body 1006 of the non-contact and contact thermometer 1001. The contact sensor 1018 detects temperature in response to direct contact with the human or animal. The dual sensors 1004 and 1018 provide both convenience and heightened accuracy in detecting temperatures in humans or animals. In some situations, the non-contact sensor 1004 provides an initial instrument of temperature detection of a human or animal and the contact sensor 1018 provides a second instrument of temperature detection of the human or animal.

After the non-contact and contact thermometer 1001 is connected to a mobile device 906 through the cable 902, configuration data 908 is transmitted from the non-contact and contact thermometer 1001 through the cable 902 and to the mobile device 906. The configuration data 908 describes and represents the hardware characteristics and functional capabilities of non-contact and contact thermometer 1001. The mobile device 906 generates diagnostic instructions 910 from the configuration data 908 and transmits the diagnostic instructions 910 through the cable 902 to the non-contact and contact thermometer 1001. The non-contact and contact thermometer 1001 performs or executes the diagnostic instructions 910 from which diagnostic results 912 are generated and transmitted through the cable 902 to the mobile device 906.

The mobile device 906 generates calibration instructions 914 from the configuration data 908 and transmits the calibration instructions 914 through the cable 902 to the non-contact and contact thermometer 1001. The non-contact and contact thermometer 1001 performs or executes the calibration instructions 914 from which calibration results 916 are generated and transmitted through the cable 902 to the mobile device 906. In some implementations, the mobile device 906 generates a notice of the completed calibration in reference to the date/time and the calibration results 916 and transmits the notice of the completed calibration to the server 918 of the compliance office. In some implementations, the mobile device 906 transmits the configuration data 908, the diagnostic results 912 and/or the calibration results 916 to the server 918 of the compliance office.

Figure 11:
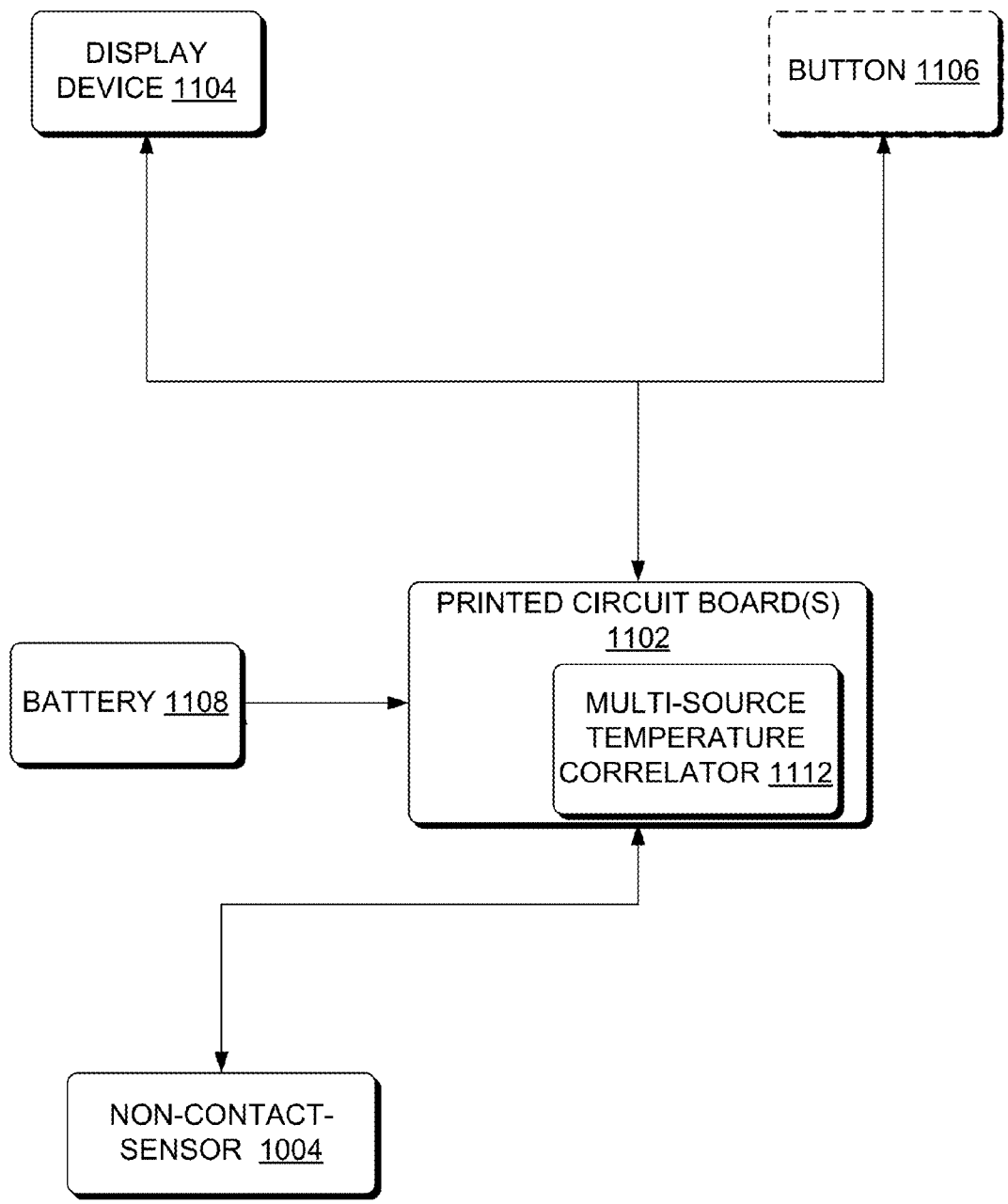
FIG. 11 is a block diagram of apparatus to measure temperature from multiple source points, according to an implementation.

FIG. 11 is a block diagram of apparatus 1100 to measure temperature from multiple source points, according to an implementation. A source point is an external point or position. Apparatus 1100 is handheld and battery powered for intermittent measurement and monitoring of human or animal body temperature of people of all ages. Apparatus 1100 measures electromagnetic energy emitted from multiple source points of the skin surface, such as infrared energy, of the human or animal and direct body temperature. Apparatus 1100 is operationally simple enough to be used by consumers in the household environment, yet accurate enough to be used by professional medical facilities.

Apparatus 1100 includes one or more printed circuit board(s) 1102.

Apparatus 1100 also includes a display device 1104 that is operably coupled to the one or more printed circuit board(s) 1102. Some implementations of apparatus 1100 also include a button 1106 that is operably coupled to the one or more printed circuit board(s) 1102. Apparatus 1100 also includes a battery 1108, such as a lithium ion battery, that is operably coupled to the one or more printed circuit board(s) 1102.

Apparatus 1100 also includes a non-contact sensor 1004 that is operably coupled to the one or more printed circuit board(s) 1102. The non-contact sensor 1004 detects temperature in response to remote sensing of a surface a human or animal. In some implementations, the hand-held medical device is an infrared temperature sensor. All humans or animals radiate infrared energy. The intensity of this infrared energy depends on the temperature of the human or animal, thus the amount of infrared energy emitted by a human or animal can be interpreted as a proxy or indication of the temperature of the human or animal. The non-contact sensor 1004 measures the temperature of a human or animal based on the electromagnetic energy radiated by the human or animal. The measurement of electromagnetic energy is taken by the non-contact sensor 1004 which constantly analyzes and registers the ambient temperature. When the operator of apparatus 1100 holds the non-contact sensor 1004 about 5-8 cm (2-3 inches) from the forehead and activates the radiation sensor, the measurement is instantaneously measured. To measure a temperature using the non-contact sensor 1004, pushing the button 1106 causes a reading of temperature measurement from the non-contact sensor 1004 and the measured temperature is thereafter displayed on the display device 1104.

Body temperature of a human or animal can be measured in many surface locations of the body. Most commonly, temperature measurements are taken of the forehead, mouth (oral), inner ear (tympanic), armpit (axillary) or rectum (core). In addition, temperature measurements are taken of a tympanic membrane surface (an internal tympanic membrane surface in an ear canal). An ideal place to measure temperature is the forehead in addition to the tympanic membrane surface. When electromagnetic energy is sensed from two or more source points, for example, the forehead and the external tympanic membrane surface, a multi-source temperature correlator 1112 performs one or more of the correlating actions in the methods as described in FIG. 44-46. The multi-source temperature correlator 1112 correlates the temperatures sensed by the non-contact sensor 1004 from the multiple source points (e.g. the forehead and the tympanic surface) to another temperature, such as a core temperature of the subject, an axillary temperature of the subject, a rectal temperature of the subject and/or an oral temperature of the subject. The multi-source temperature correlator 1112 can be implemented as a component on a microprocessor, such as controller chip 5404 in FIG. 54 or read-only memory.

The apparatus 1100 also detects the body temperature of a human or animal regardless of the room temperature because the measured temperature of the non-contact sensor 1004 is adjusted in reference to the ambient temperature in the air in the vicinity of the apparatus. The human or animal must not have undertaken vigorous physical activity prior to temperature measurement in order to avoid a misleading high temperature. Also, the room temperature should be moderate, 50° F. to 120° F.

The thermometer 1001 provides a non-invasive and non-irritating means of measuring human or animal temperature to help ensure good health.

In some implementations, the apparatus 1100 includes only one printed circuit board 1102, in which case the printed circuit board 1102 includes not more than one printed circuit board 1102. In some implementations, the apparatus 1100 includes two printed circuit boards 1102, such as a first printed circuit board and a second printed circuit board. In some implementations, the printed circuit board(s) 1102 include a microprocessor. In some implementations, the apparatus 1100 includes only one display device 1104, in which case the display device 1104 includes not more than one display device 1104. In some implementations, the display device 1104 is a liquid-crystal diode (LCD) display device. In some implementations, the display device 1104 is a light-emitting diode (LED) display device. In some implementations, the apparatus 1100 includes only one battery 1108, which case the battery 1108 includes not more than one battery 1108.

When evaluating results, the potential for daily variations in temperature can be considered. In children less than 6 months of age daily variation is small. In children 6 months to 2 years old the variation is about 1 degree. By age 6 variations gradually increase to 2 degrees per day. In adults there is less body temperature variation.

While the apparatus 1100 is not limited to any particular printed circuit board(s) 1102, display device 1104, button 1106, battery 1108 and a multi-source temperature correlator 1112, for sake of clarity a simplified printed circuit board(s) 1102, display device 1104, button 1106, battery 1108 and multi-source temperature correlator 1112 are described.

Figure 12:
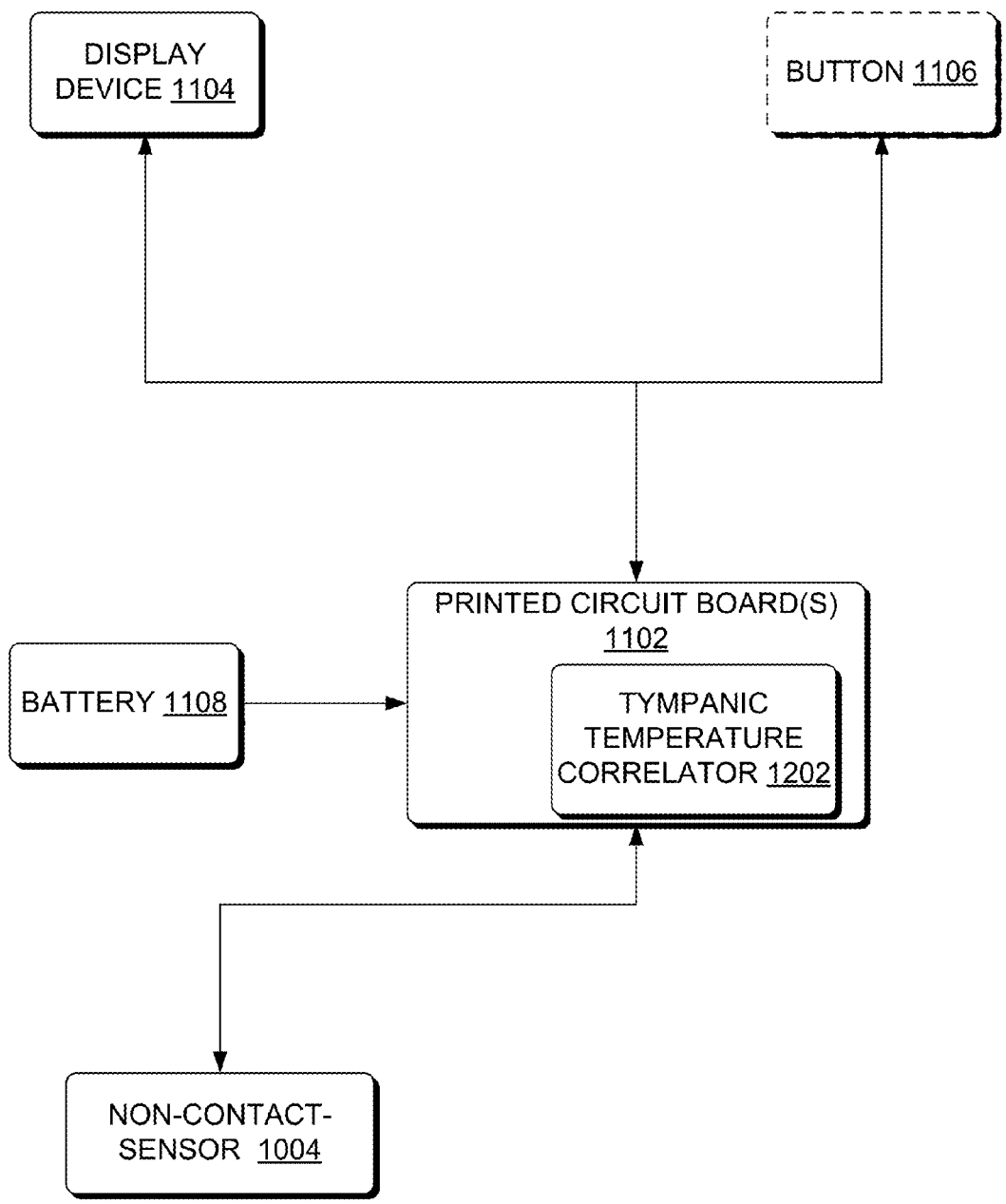
FIG. 12 is a block diagram of apparatus to measure temperature from a tympanic source point, according to an implementation.

FIG. 12 is a block diagram of apparatus 1200 to measure temperature from a tympanic source point, according to an implementation. Apparatus 1200 is handheld and battery powered for intermittent measurement and monitoring of human or animal body temperature of people of all ages. Apparatus 1200 measures electromagnetic energy, such as infrared energy, emitted from a source point of the skin surface of a tympanic membrane surface of the human or animal. Apparatus 1200 is operationally simple enough to be used by consumers in the household environment, yet accurate enough to be used by professional medical facilities.

Apparatus 1200 includes one or more printed circuit board(s) 1102 and a display device 1104 that is operably coupled to the one or more printed circuit board(s) 1102. Some implementations of apparatus 1200 also include a button 1106 that is operably coupled to the one or more printed circuit board(s) 1102. Apparatus 1200 also includes a battery 1108, such as a lithium ion battery, that is operably coupled to the one or more printed circuit board(s) 1102.

Apparatus 1200 also includes a non-contact-sensor 1004 that is operably coupled to the one or more printed circuit board(s) 1102. The non-contact-sensor 1004 detects temperature in response to remote sensing of a surface a human or animal. When the operator of apparatus 1200 holds the non-contact-sensor 1004 about 5-8 cm (2-3 inches) from the tympanic membrane surface and activates the non-contact-sensor 1004, the measurement is instantaneously measured.

Figure 44:
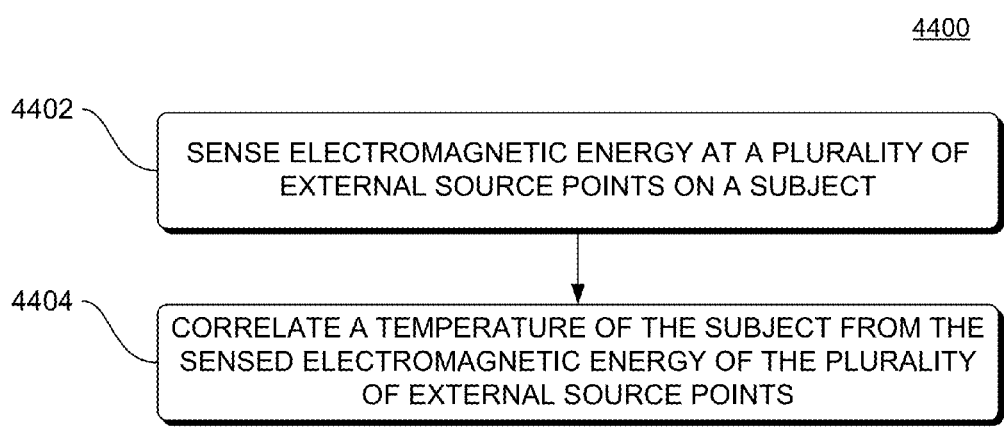
FIG. 44 is a flowchart of a method to measure temperature from multiple source points.
Figure 45:
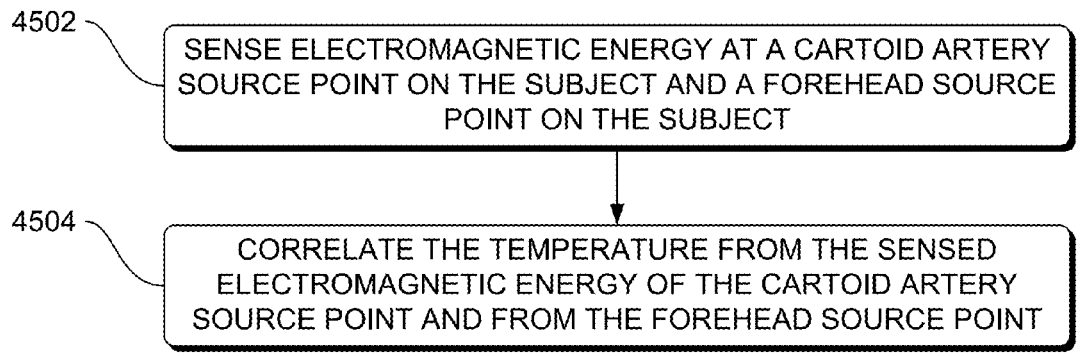
FIG. 45 is a flowchart of a method to measure temperature of a forehead and a tympanic surface, according to an implementation.
Figure 46:
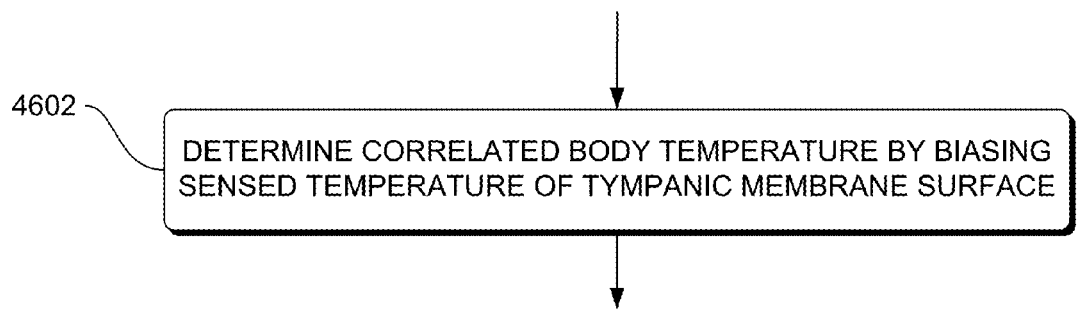
FIG. 46 is a flowchart of a method of determining correlated temperature of tympanic membrane surface, according to an implementation.

When electromagnetic energy is sensed by the non-contact-sensor 1004 from the tympanic membrane surface on the right side of a human neck, a tympanic temperature correlator 1202 performs one or more of the correlating actions in the methods as described in FIG. 44-46. The tympanic temperature correlator 1202 correlates the temperatures sensed by the non-contact-sensor 1004 from the tympanic source point to another temperature, such as a core temperature of the subject, an axillary temperature of the subject, a rectal temperature of the subject and/or an oral temperature of the subject. The tympanic temperature correlator 1202 can be implemented as a component on a microprocessor, such as controller chip 5404 in FIG. 54 or read-only memory.

The apparatus 1200 also detects the body temperature of a human or animal regardless of the room temperature because the measured temperature of the non-contact-sensor 1004 is adjusted in reference to the ambient temperature in the air in the vicinity of the apparatus 1200. The human or animal must not have undertaken vigorous physical activity prior to temperature measurement in order to avoid a misleading high temperature. Also, the room temperature should be moderate, 50° F. to 120° F.

In some implementations, the apparatus 1200 includes only one printed circuit board 1102, in which case the printed circuit board 1102 includes not more than one printed circuit board 1102. In some implementations, the apparatus 1200 includes two printed circuit boards 1102, such as a first printed circuit board and a second printed circuit board. In some implementations, the printed circuit board(s) 1102 include a microprocessor. In some implementations, the apparatus 1200 includes only one display device 1104, in which case the display device 1104 includes not more than one display device 1104. In some implementations, the display device 1104 is a liquid-crystal diode (LCD) display device. In some implementations, the display device 1104 is a light-emitting diode (LED) display device. In some implementations, the apparatus 1200 includes only one battery 1108, which case the battery 1108 includes not more than one battery 1108.

While the apparatus 1200 is not limited to any particular printed circuit board(s) 1102, display device 1104, button 1106, battery 1108, a non-contact-sensor 1004 and a tympanic temperature correlator 1202, for sake of clarity a simplified printed circuit board(s) 1102, display device 1104, button 1106, battery 1108, a non-contact-sensor 1004 and a tympanic temperature correlator 1202 are described.

Figure 13:
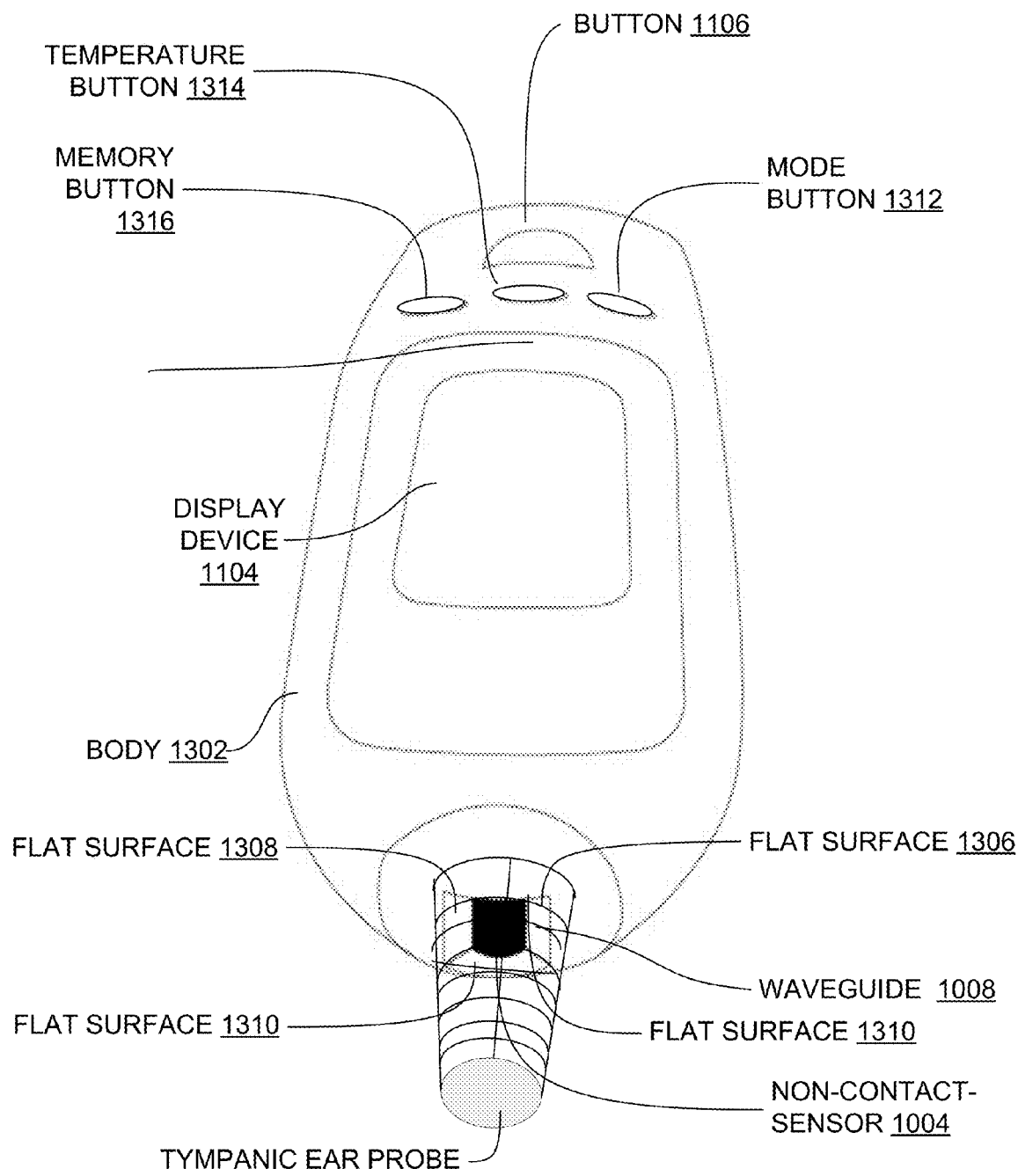
FIG. 13 is an isometric top-view block diagram of an apparatus to measure temperature using both a hand-held medical device with a right-angled waveguide and not including a contact thermometer, according to an implementation.

FIG. 13 is an isometric top-view block diagram of an apparatus 1300 to measure temperature using both a hand-held medical device with a right-angled waveguide and not including a contact thermometer, according to an implementation. Apparatus 1300 is handheld and battery powered for intermittent measurement and monitoring of human or animal body temperature of people of all ages. Apparatus 1300 measures non-contact infrared energy emitted from the skin surface of the human or animal. Apparatus 1300 can be used by consumers in the household environment.

Apparatus 1300 includes the display device 1104 that is mounted on the exterior of a body 1302 or other housing of the apparatus 1300. Apparatus 1300 also includes the button 1306 that is mounted on the exterior of the body 1302 or other housing of the apparatus 1300. Apparatus 1300 also includes a sensor (not shown in FIG. 13) of the non-contact sensor 1004 that is mounted in the interior of the body 1302 of the apparatus 1300. The non-contact sensor 1004 detects temperature in response to remote sensing of a surface a human or animal. The waveguide 1008 is positioned in proximity to the IR sensor (not shown). The waveguide 1008 includes at least one flat planar surface. The apparatus 1300 includes 4 flat planar surfaces 1306, 1308, 1310 and 1312.

Apparatus 1300 also includes a mode button 1312 that when pressed by an operator toggles or switches between three different detection modes, a first detection mode being detection and display of surface temperature, a second detection mode being detection and display of body temperature and a third detection mode being detection and display of room temperature.

Apparatus 1300 also includes a temperature button 1314 that when pressed by an operator toggles or switches between two different temperature modes, a first temperature mode being display of temperature in Celsius and a second temperature mode being display of temperature in Fahrenheit.

Apparatus 1300 also includes a memory button 1316 that when pressed by an operator toggles or switches between a plurality of past temperature readings. In one implementation, the plurality of past temperature readings is 40.

A tympanic probe (100 in FIG. 1-2, 300 in FIG. 3-4, 500 in FIG. 5-6 or 700 in FIG. 7-8) is installed on the forward end of apparatus 1300 suitable for use as a clinical thermometer when the tympanic probe 100 is inserted into an ear canal.

To take a person's body temperature, the tympanic probe 100 is introduced into the ear canal of an ear. In the presence of a tympanic probe 100 of a radiation thermometer, the infrared radiation emitted by the tympanic membrane surface (not shown) passes through a window/lens 104 that is transparent to infrared radiation in the relevant measurement range at the forward end of the tympanic probe 100 and is directed, through the body 102 that acts as an infrared waveguide extending coaxially with the lengthwise axis of the tympanic probe 100, to the waveguide 1008, entering an infrared sensor (e.g. 1406 in FIG. 14). The temperature increase produced in the infrared sensor results in an electrical output voltage from which the radiation temperature is derived, which temperature is indicated to the user as by means of the digital display device 1104. The body 102 is preferably fabricated from plastic. The snap-fit tabs 108 and 109 are inserted into small slots in the housing of the apparatus 1300 and by compressive pressure, hold the tympanic probe adjacent to the housing of the apparatus 1300. In some implementations, mechanical sensors detect and determine the presence of the snap-fit tabs 108 and 109 in the small slots in the housing of the apparatus 1300, which is a function also described in block 5002 in FIG. 50.

Figure 14:
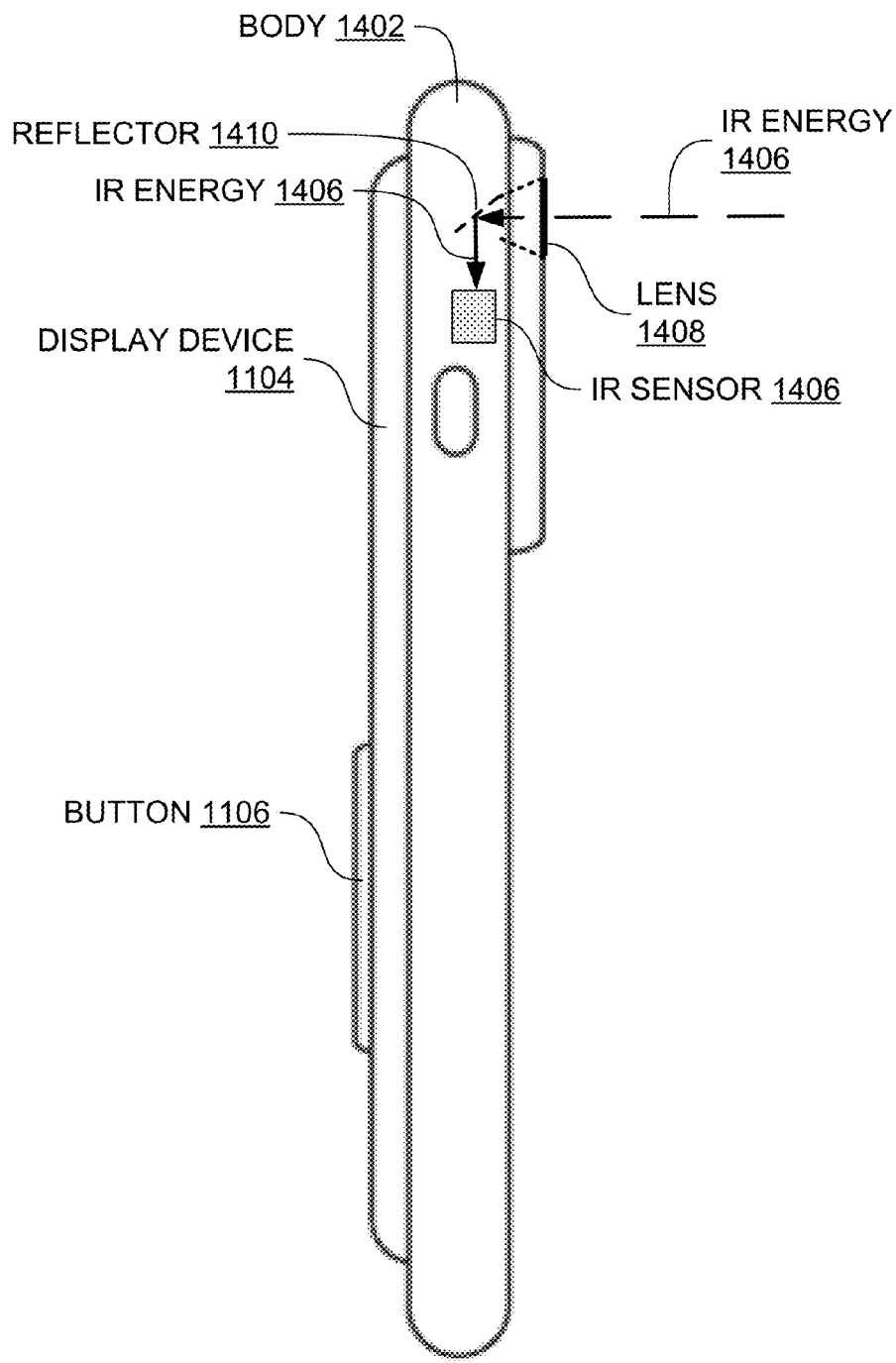
FIG. 14 is a side-view block diagram of an apparatus to measure temperature using a hand-held medical device with a right-angled waveguide, according to an implementation.

FIG. 14 is a side-view block diagram of an apparatus 1400 to measure temperature using a hand-held medical device with a right-angled waveguide, according to an implementation. Apparatus 1400 is handheld and battery powered for intermittent measurement and monitoring of human or animal body temperature of people of all ages. Apparatus 1400 measures non-contact infrared energy emitted from the skin surface of the human or animal. Apparatus 1400 can be used by consumers in the household environment.

Apparatus 1400 includes the display device 1104 that is mounted on the exterior of a body 1402 or other housing of the apparatus 1400. Apparatus 1400 also includes the button 1106 that is mounted on the exterior of the body 1402 or other housing of the apparatus 1400.

Apparatus 1400 includes the non-contact sensor having an infrared sensor 1404. The infrared sensor 1404 is operable to receive infrared energy 1406 via a pathway to the infrared sensor 1404. Apparatus 1400 includes a lens 1408 that is positioned over the pathway. In some implementations, the lens 1408 has only right-angled edges, the lens 1408 being square in geometry, that is transverse to the pathway to the infrared sensor 1406. The pathway intersects the lens 1408. A reflector 1410 that is positioned at a 45 degree angle to the infrared sensor 1404. The lens 1408 has a longitudinal axis that is perpendicular to a longitudinal axis of the infrared sensor. The reflector 1410 is positioned at a 45 degree angle to the lens 1404. The pathway is coincident to the IR energy 1406 that passes through the lens 1408, reflects off of the reflector 1410 and to the IR sensor 1404.

Apparatus 1400 also includes the sensor 1303 of the non-contact sensor 1004, the sensor 1303 being mounted in the interior of the body 1302 of the apparatus 1400. The non-contact sensor 1004 detects temperature in response to remote sensing of a surface of a human or animal. The contact sensor 1018 detects temperature in response to direct contact with the human or animal. The dual sensors 1004 and 1018 provide improved convenience and heightened accuracy in detecting temperatures in humans or animals. In some situations, the hand-held medical device 1004 is used as initial instrument of temperature detection of a human or animal and the contact sensor 1018 is used as a second instrument of temperature detection of the human or animal.

Figure 15:
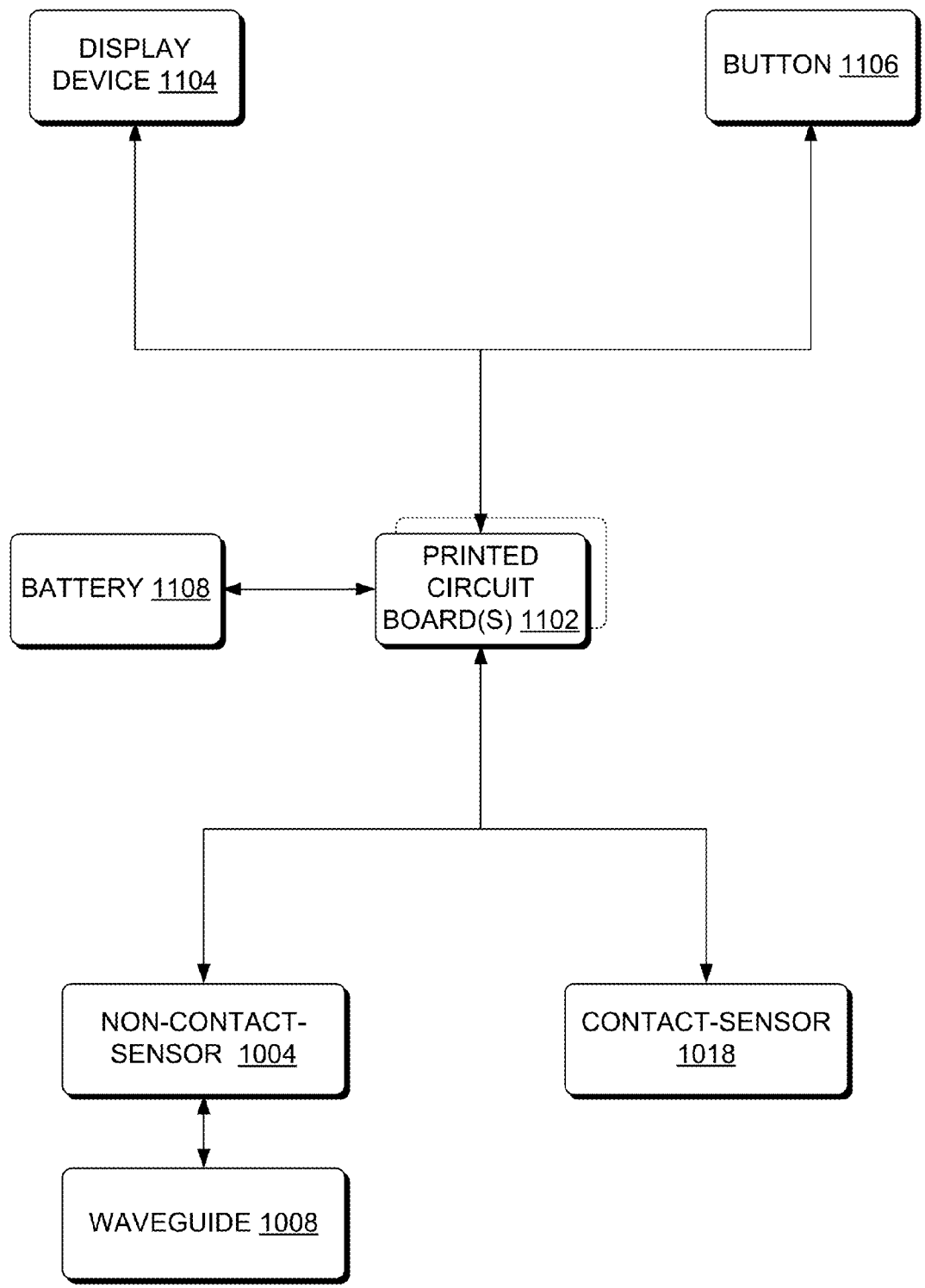
FIG. 15 is a block diagram of apparatus to measure temperature, according to an implementation having a right-angled waveguide.

FIG. 15 is a block diagram of apparatus 1500 to measure temperature, according to an implementation. Apparatus 1500 is handheld and battery powered for intermittent measurement and monitoring of human or animal body temperature of people of all ages. Apparatus 1500 measures both electromagnetic energy emitted from the skin surface, such as infrared energy, of the human or animal and direct body temperature. Apparatus 1500 is operationally simple enough to be used by consumers in the household environment, yet accurate enough to be used by professional medical facilities.

Apparatus 1500 includes one or more printed circuit board(s) 1102.

Apparatus 1500 also includes a display device 1104 that is operably coupled to the one or more printed circuit board(s) 1102. Some implementations of apparatus 1500 also include a button 1106 that is operably coupled to the one or more printed circuit board(s) 1102. Apparatus 1500 also includes a battery 1108, such as a lithium ion battery, that is operably coupled to the one or more printed circuit board(s) 1102.

Apparatus 1500 also includes a non-contact sensor 1004 that is operably coupled to the one or more printed circuit board(s) 1102. The non-contact sensor 1004 detects temperature in response to remote sensing of a surface a human or animal. In some implementations the hand-held medical device is an infrared temperature sensor.

Some implementations of apparatus 1500 also include a contact sensor 1018 that is operably coupled to the one or more printed circuit board(s) 1102. The contact sensor 1018 detects temperature in response to direct contact with a human or animal.

A right-angled waveguide 1008 is positioned in proximity to the hand-held medical device 1004. The geometry of the right-angled waveguide 1008 has at least one right-angle and at least flat planar surface. In some implementations, the geometry of the right-angled waveguide 1008 has only right-angled edges. In general, a waveguide is a structure of a passageway or pathway which guides waves, such as electromagnetic waves. Waves in open space propagate in all directions, as spherical waves. In this way the wave lose power proportionally to the square of the distance; that is, at a distance R from the source, the power is the source power divided by R2. The waveguide confines the wave to propagation in one dimension, so that (under ideal conditions) the wave loses no power while propagating. Waves are confined inside the waveguide due to total reflection from the waveguide wall, so that the propagation inside the waveguide can be described approximately as a "zigzag" between the walls. There are different types of waveguides for each type of wave. The original and most common implementation of a waveguide is a hollow conductive metal pipe used to carry high frequency radio waves, particularly microwaves. Waveguides differ in their geometry which can confine energy in one dimension such as in slab waveguides or a waveguide can confine energy in two dimensions as in fiber or channel waveguides. As a rule of thumb, the width of a waveguide needs to be of the same order of magnitude as the wavelength of the guided wave.

A conventional geometry of a waveguide has a circular cross-section, which is most useful for gathering electromagnetic waves that have a rotating, circular polarization in which the electrical field traces out a helical pattern as a function of time. However, infrared energy emitted from a surface of a human does not have a rotating, circular polarization in which the electrical field traces out a helical pattern as a function of time. Therefore, in apparatus that measures infrared energy of a human as a proxy of temperature of the human, circular and rounded waveguides should not be used. The waveguide 1008 is not conical in geometry because a conical waveguide reflects the electromagnetic waves in a somewhat incoherent manner in which the electromagnetic waves are received at the sensor with a decreased degree of coherency, thus decreasing the signal strength; and the conical waveguide reflects a significant portion of electromagnetic waves out of the waveguide and away from the sensor, thus further reducing the signal strength of the electromagnetic waves received by the sensor and therefore further reducing the accuracy and speed of the non-contact temperature sensing. More specifically, waveguide 1008 is not a conical funnel in which the conical funnel has an opening at one end of a longitudinal axis that has a larger diameter than an opening at the other end of the longitudinal axis.

The dual sensors 1004 and 1018 provide improved convenience and heightened accuracy in detecting temperatures in humans or animals. In some situations, the hand-held medical device 1004 provides an initial temperature detection of a human or animal and the contact sensor 1018 provides a second detection of temperature detection of the human or animal. The non-contact sensor 1004 eliminates need for contact with the skin, yet the contact sensor 1018 provides a more accurate detection of human or animal body temperature to supplement or verify the temperature detected by the hand-held medical device.

In some implementations, the apparatus 1500 includes only one printed circuit board 1102, in which case the printed circuit board 1102 includes not more than one printed circuit board 1102. In some implementations, the apparatus 1500 includes two printed circuit boards 1102, such as a first printed circuit board and a second printed circuit board. In some implementations, the printed circuit board(s) 1102 include a microprocessor. In some implementations, the apparatus 1500 includes only one display device 1104, in which case the display device 1104 includes not more than one display device 1104. In some implementations, the display device 1104 is a liquid-crystal diode (LCD) display device. In some implementations, the display device 1104 is a light-emitting diode (LED) display device. In some implementations, the apparatus 1500 includes only one battery 1108, which case the battery 1108 includes not more than one battery 1108.

While the apparatus 1500 is not limited to any particular printed circuit board(s) 1102, display device 1104, button 1106, battery 1108, non-contact sensor 1004 and a contact sensor 1018, for sake of clarity a simplified printed circuit board(s) 1102, display device 1104, button 1106, battery 1108, non-contact sensor 1004 and a contact sensor 1018 are described.

Figure 16:
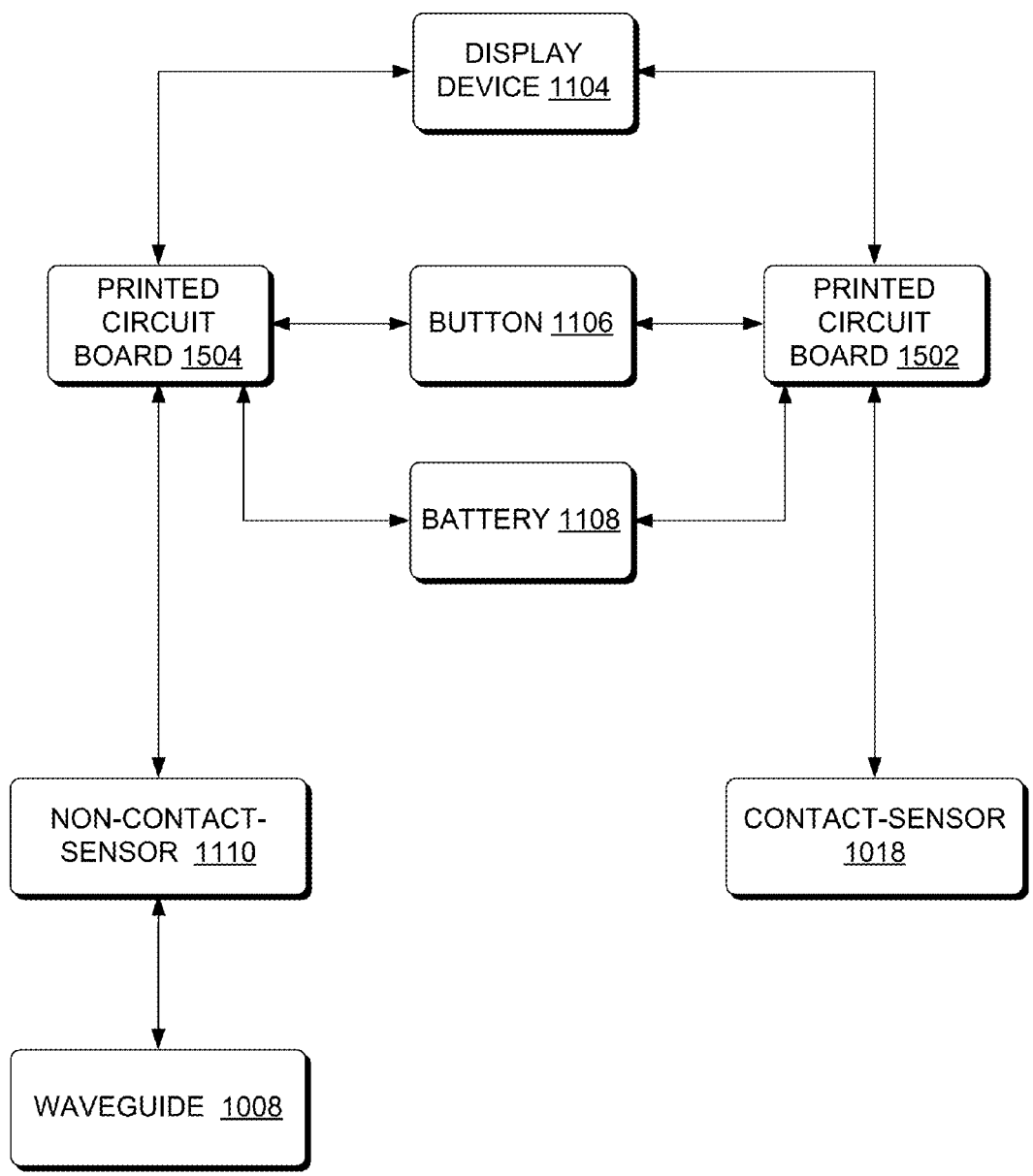
FIG. 16 is a block diagram of apparatus to measure temperature, according to an implementation in which each of a hand-held medical device and a contact thermometer are controlled by a separate printed circuit board and the hand-held medical device has a right-angled waveguide, according to an implementation.

FIG. 16 is a block diagram of apparatus 1600 to measure temperature, according to an implementation in which each of a hand-held medical device and a contact thermometer are controlled by a separate printed circuit board and the hand-held medical device has a right-angled waveguide, according to an implementation.

Apparatus 1600 includes the contact sensor 1018 that is operably coupled to a first printed circuit board 1602, a non-contact sensor 1004 that is operably coupled to a second printed circuit board 1604, the display device 1104 that is operably coupled to the first printed circuit board 1602 and the second printed circuit board 1604, the button 1106 that is operably coupled to the first printed circuit board 1602 and the second printed circuit board 1604 and the battery 1108 that is operably coupled to the first printed circuit board 1602 and the second printed circuit board 1604. In apparatus 1600, the display device 1104, the button 1106 and the battery 1108 are shared, but each thermometer has a dedicated printed circuit board.

A right-angled waveguide 1008 is positioned in proximity to the hand-held medical device. The geometry of the right-angled waveguide 1008 has at least one right-angle. In some implementations, the geometry of the right-angled waveguide 1008 has only right-angled edges.

Some implementations of apparatus in FIG. 11-16 include an ambient air temperature sensor that is operably coupled to, or a part of, the printed circuit board(s) 1102, 1602 or 1604.

Figure 53:
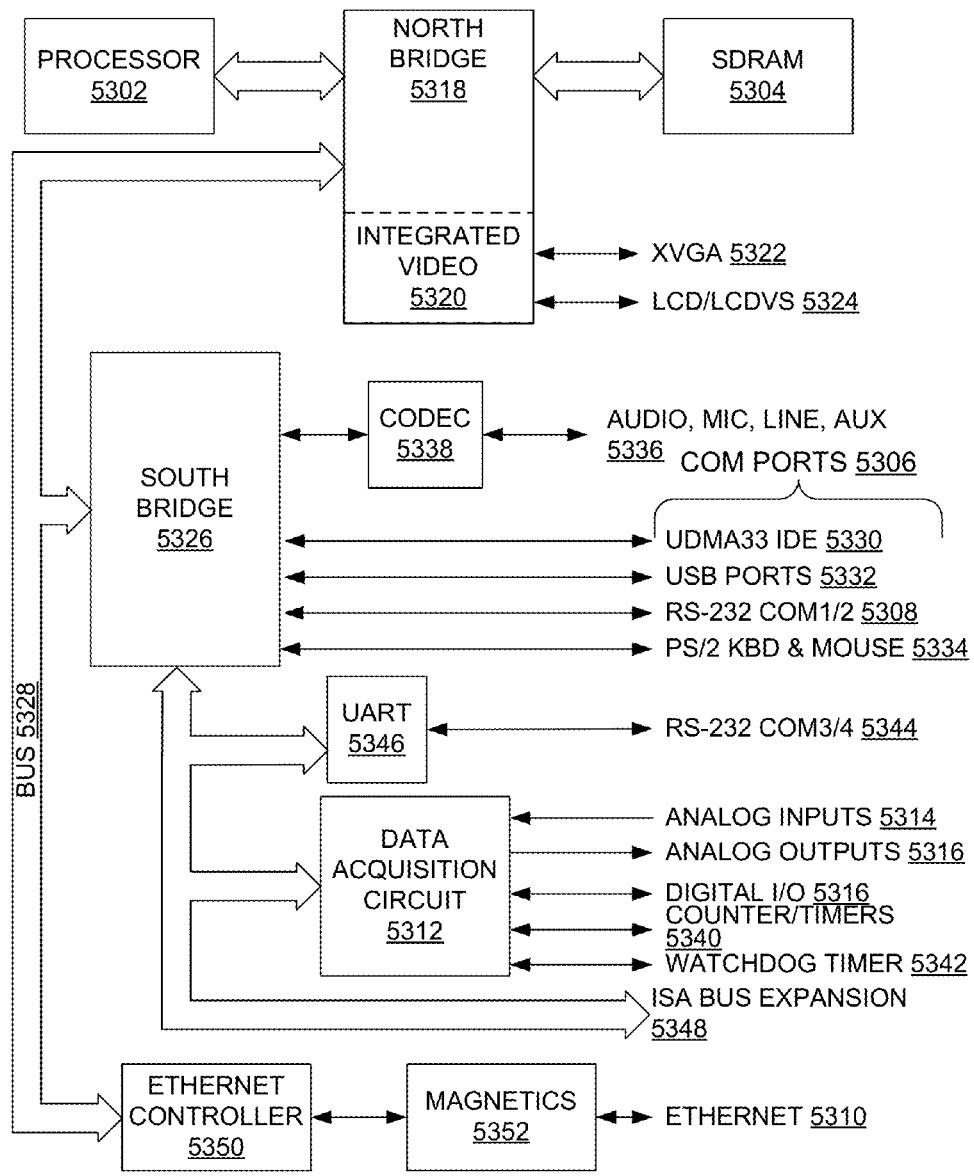
FIG. 53 is a block diagram of a thermometer control computer, according to an implementation.
Figure 54:
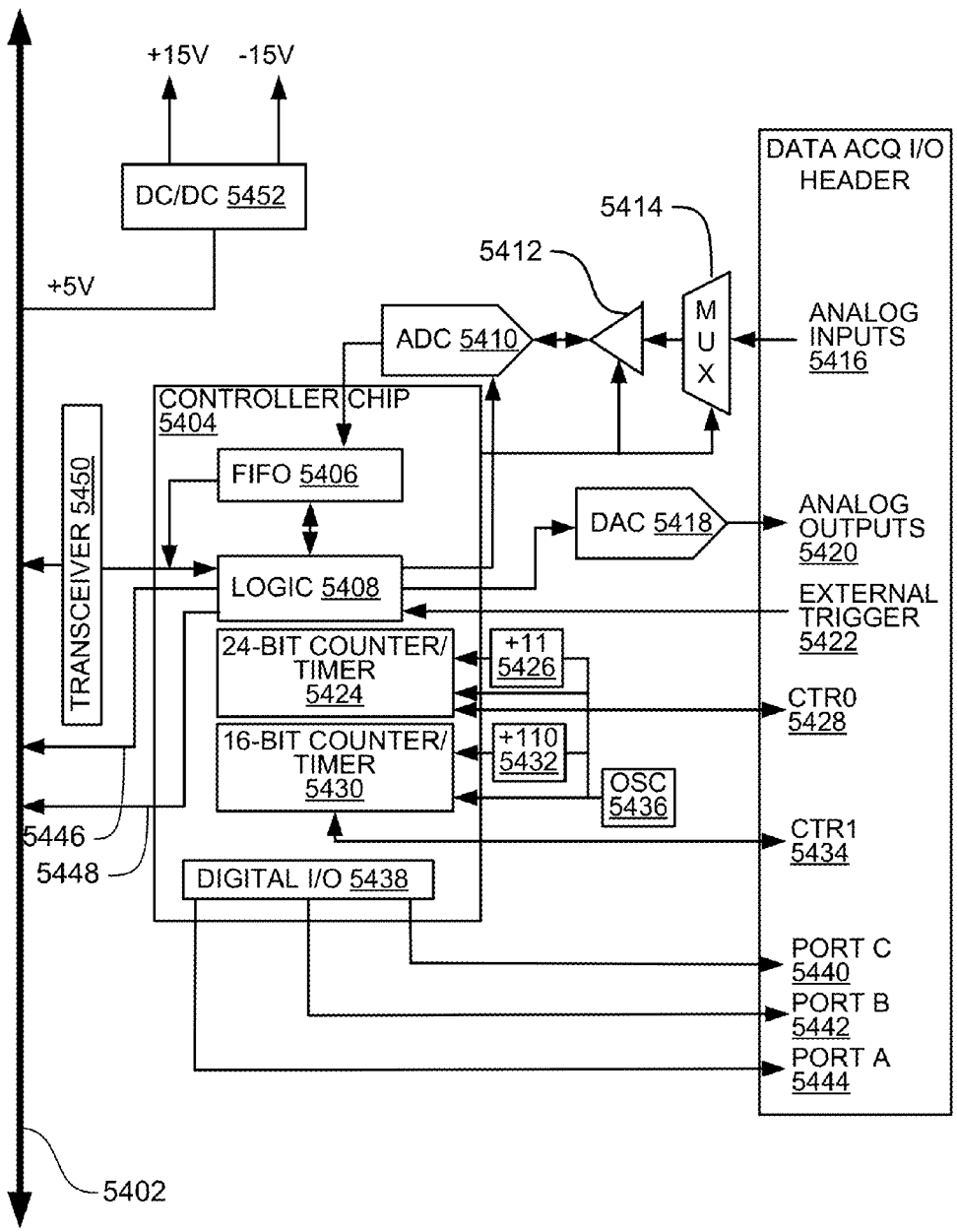
FIG. 54 is a block diagram of a data acquisition circuit of a thermometer control computer, according to an implementation

FIG. 17-23 are block diagrams of a sensor collector to guide electromagnetic energy to measure temperature, according to an implementation. FIG. 17 is a side cut-away view of the sensor collector to guide electromagnetic energy. The electromagnetic energy 1702 enters the cavity 1704 of the sensor collector and reflects off of the shroud 1706 and through the bottom opening. The shroud 1706 has in an inside surface that is concave. The shroud 1706 is one example of the reflector 1410 in FIG. 14. FIG. 53 is a top view of the sensor collector to guide electromagnetic energy. FIG. 54 is a front view of the sensor collector to guide electromagnetic energy. FIG. 20 is a side view of the sensor collector to guide electromagnetic energy. FIG. 21 is a bottom view of the sensor collector to guide electromagnetic energy. FIG. 22 is a top cut-away view of the sensor collector to guide electromagnetic energy. FIG. 23 is a bottom isometric view of the sensor collector to guide electromagnetic energy.

Figure 24:
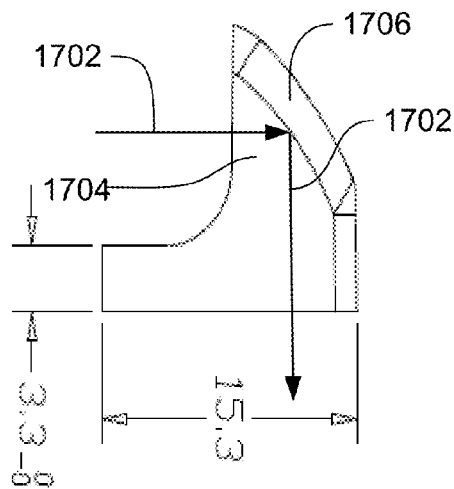
FIG. 24-29 are block diagrams of a shroud of a sensor collector to guide electromagnetic energy to measure temperature, according to an implementation.
Figure 25:
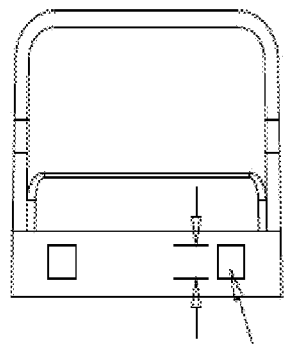
Figure 26:
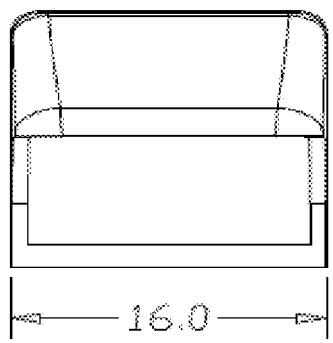
Figure 27:
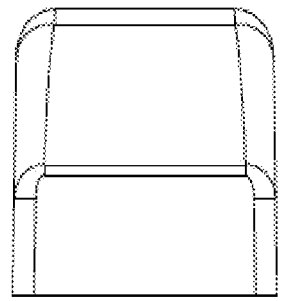
Figure 28:
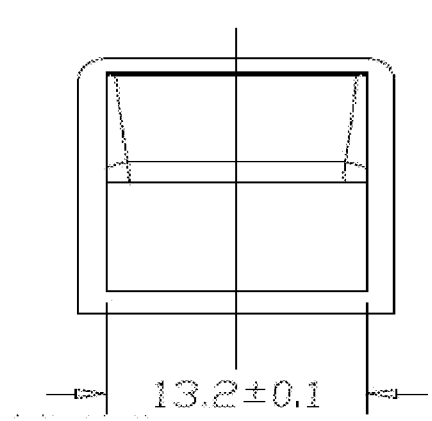
Figure 29:
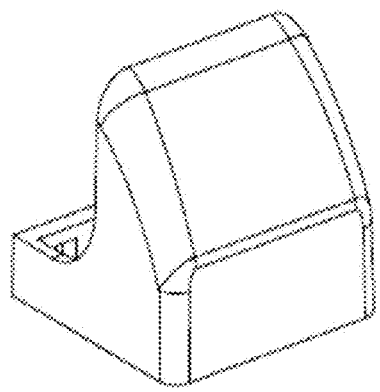

FIG. 24-29 are block diagrams of a shroud of a sensor collector to guide electromagnetic energy to measure temperature, according to an implementation. FIG. 24 is a side view of a shroud of a sensor collector to guide electromagnetic energy. The electromagnetic energy 1702 enters the cavity 1704 of the sensor collector and reflects off of the shroud 1706 and through the bottom opening. FIG. 25 is a bottom view of a shroud of a sensor collector to guide electromagnetic energy. FIG. 26 is a front cut-away view of a shroud of a sensor collector to guide electromagnetic energy. FIG. 27 is a front view of a shroud of a sensor collector to guide electromagnetic energy. FIG. 29 is a front cut-away view of a shroud of a sensor collector to guide electromagnetic energy. FIG. 29 is a back top isometric view of a shroud of a sensor collector to guide electromagnetic energy.

Figure 30:
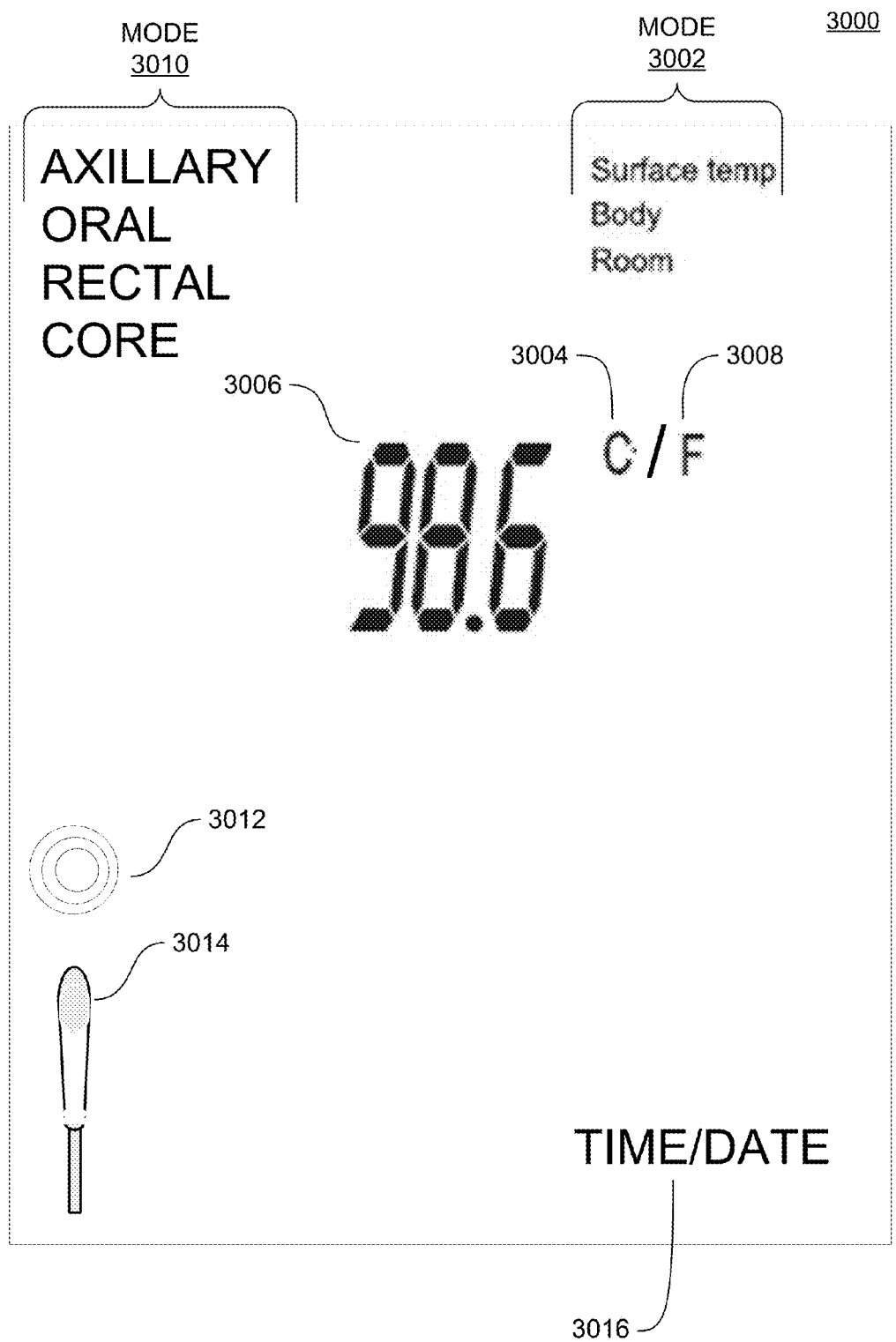
FIG. 30 is a representation of display that is presented on the display device of apparatus in FIG. 11-16, according to an implementation that manages both a non-contact sensor and a contact sensor.

FIG. 30 is a representation of display that is presented on the display device of apparatus in FIG. 11-16, according to an implementation that manages both a non-contact sensor and a contact sensor.

Some implementations of display 3000 include a representation of three detection modes 3002, a first detection mode being detection and display of surface temperature, a second detection mode being detection and display of body temperature and a third detection mode being detection and display of room temperature.

Some implementations of display 3000 include a representation of Celsius 3004 that is activated when the apparatus is in Celsius mode.

Some implementations of display 3000 include a representation of a sensed temperature 3006.

Some implementations of display 3000 include a representation of Fahrenheit 3008 that is activated when the apparatus is in Fahrenheit mode.

Some implementations of display 3000 include a representation of a mode 3010 of site temperature sensing, a first site mode being detection of an axillary surface temperature, a second site mode being detection of an oral temperature, a third site mode being detection of a rectal temperature and a fourth site mode being detection of a core temperature.

Some implementations of display 3000 include a representation of a scanner mode 3012 that is activated when the sensed temperature 3006 is from a non-contact sensor 1004.

Some implementations of display 3000 include a representation of a probe mode 3014 that is activated when the sensed temperature 3006 is from a contact sensor 1018.

Some implementations of display 3000 include a representation of the current time/date 3016 of the apparatus.

Figure 31:
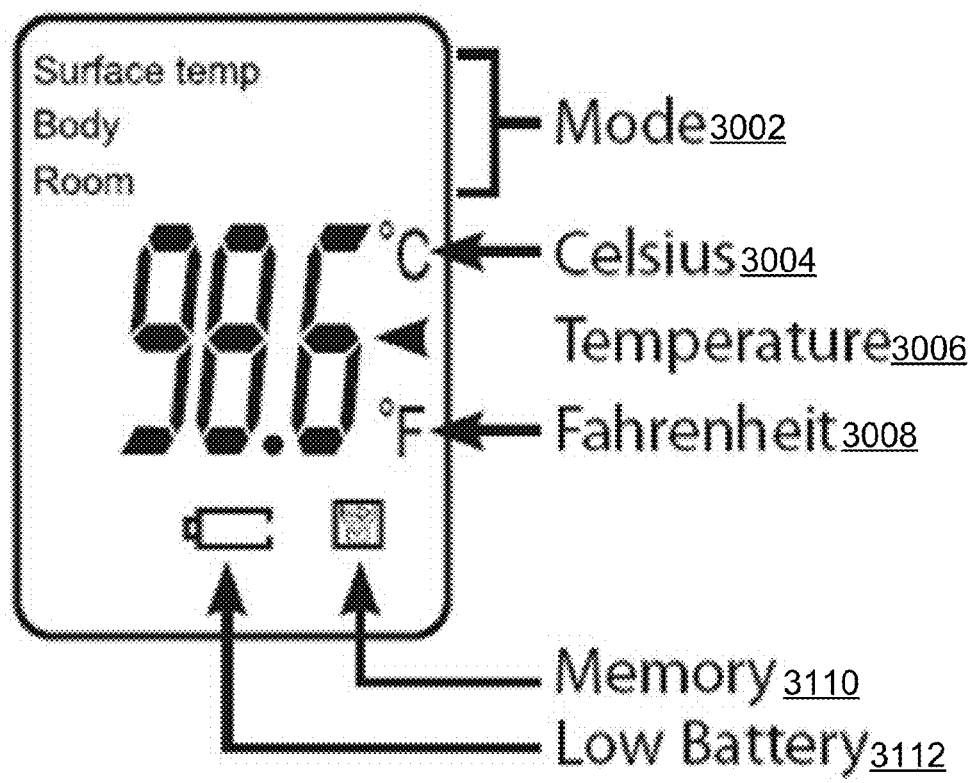
FIG. 31 is a representation of display that is presented on the display device of apparatus in FIG. 11-16, according to an implementation.

FIG. 31 is a representation of display 3100 that is presented on the display device of apparatus in FIG. 11-16, according to an implementation.

Some implementations of display 3100 include a representation of three detection modes 3002, a first detection mode being detection and display of surface temperature, a second detection mode being detection and display of body temperature and a third detection mode being detection and display of room temperature.

Some implementations of display 3100 include a representation of Celsius 3004 that is activated when the apparatus is in Celsius mode.

Some implementations of display 3100 include a representation of a temperature 3006.

Some implementations of display 3100 include a representation of Fahrenheit 3008 that is activated when the apparatus is in Fahrenheit mode.

Some implementations of display 3100 include a representation of memory 3110.

Some implementations of display 3100 include a representation of battery charge level 3112.

Figure 32:
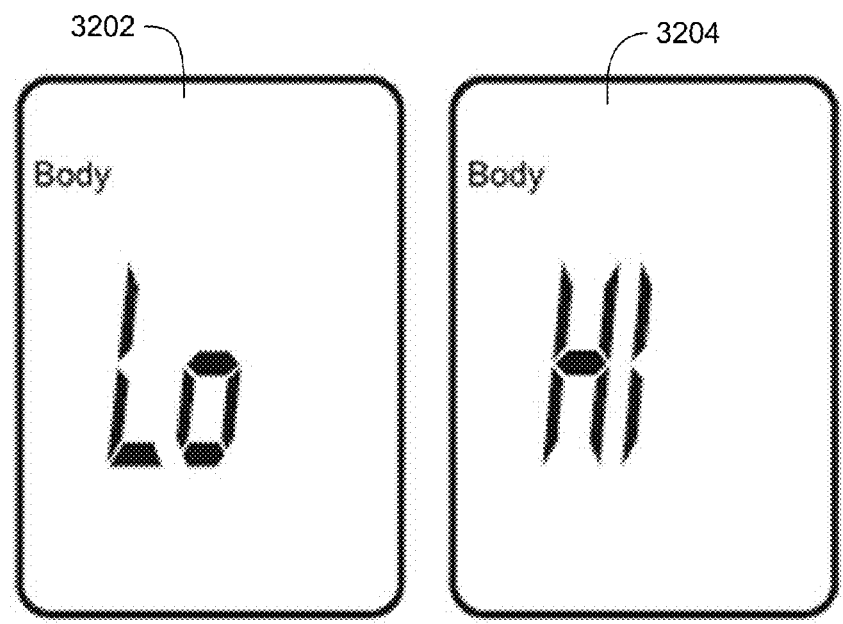
FIG. 32 is a representation of text displays that are presented on the display device of apparatus in FIG. 11-16, according to an implementation.

FIG. 32 is a representation of text displays 3200 that are presented on the display device of apparatus in FIG. 11-16, according to an implementation. Some implementations of display 3200 include a text representation that a sensed body temperature 3202 is "Lo" as in "low". Some implementations of display 3200 include a text representation that a sensed body temperature 3204 is "Hi" as in "high".

FIG. 33-38 are representations of graphical displays that are presented on the display device of apparatus in FIG. 11-16, according to implementations. The double-arrow bracket 3302 in FIG. 33-38 represents a general range of normal temperatures.

Figures 33, 34, 35:
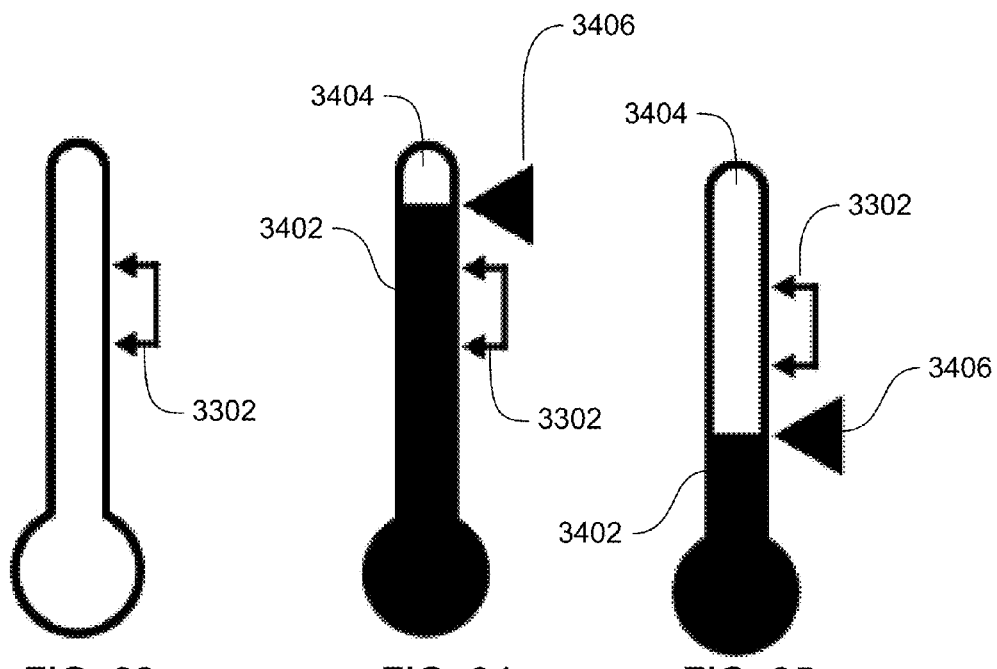
FIG. 33-38 are representations of graphical displays that are presented on the display device of apparatus in FIG. 11-16, according to implementations.

FIG. 33 is a graphical display that represents a state of having no sensed temperature. The empty thermometer in FIG. 33 indicates that no temperature sensing activity has completed.

FIG. 34 is a graphical display that represents a state of having sensed a high temperature. The thermometer in FIG. 34 having a contrasting color 3402 that is located above the general ranges of normal temperature indicates a higher than normal temperature. In FIG. 34-38, the contrasting color 3402 contrasts to the remainder 3404 of the interior of the thermometer image. In the example shown in FIG. 34-38, the contrasting color 3402 is black which contrasts with the white of the remainder 3404 of the interior of the thermometer image. FIG. 34 includes a pointer 3406 indicating the sensed temperature.

FIG. 35 is a graphical display that represents a state of having sensed a low temperature. The thermometer in FIG. 35 having only a contrasting color that is located below the general ranges of normal temperature indicates a lower than normal temperature. FIG. 35 includes a pointer 3406 indicating the sensed temperature.

Figures 36, 37, 38:
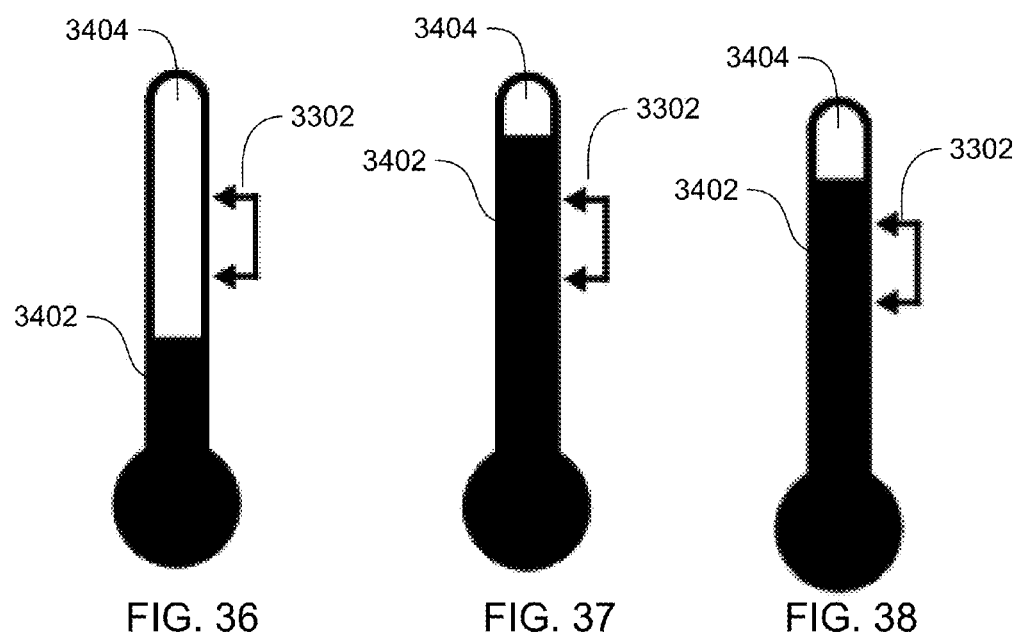

FIG. 36 is a graphical display that represents a state of having sensed a low temperature. The thermometer in FIG. 36 having contrasting color located only below the general ranges of normal temperature indicates a lower than normal temperature.

FIG. 37 is a graphical display that represents a state of having sensed a high temperature. The thermometer in FIG. 37 having contrasting color that is located above the general ranges of normal temperature indicates a higher than normal temperature.

FIG. 38 is a graphical display that represents a state of having sensed a high temperature. The thermometer in FIG. 38 having contrasting color that is located above the general ranges of normal temperature indicates a higher than normal temperature.

Use Cases of Apparatus

In one example of use of the apparatus shown in FIG. 11-16, an operator performs a scan with the hand-held medical device, the operator determines that a contact temperature is helpful or necessary and the operator performs a reading with a contact sensor 1018. In another example of use of the apparatus shown in FIG. 11-16, the operator performs a reading with the contact sensor 1018, the operator determines that a non-contact temperature is helpful or necessary and the operator performs a scan with the hand-held medical device 1004.

To perform a scan with the hand-held medical device 1004, the operator uses a button to select one three modes of the apparatus, 1) oral 2) rectal or 3) axillary. The operator pushes the scan button 1186 to initiate a non-contact temperature scan. The apparatus displays the detected temperature that is calculated in reference to the selected mode.

To determine that a contact temperature is helpful or necessary, the operator reviews the temperature displayed by the apparatus and determines that a temperature reading using a different technique, such as either contact or non-contact) would be informative.

To perform a reading with the contact sensor 1018, the operator removes a contact sensor 1018 probe from a receiver and places a disposable probe over the contact sensor 1018, and the operator inserts the probe of the contact sensor 1018 into the mouth of a human or animal. The apparatus senses in increase in temperature through the contact sensor 1018 and in response the apparatus starts a timer. After expiration of the timer, the apparatus displays on the display device 1104 the sensed temperature at the time of the timer expiration and generates an audio alert and in response the operator removes the probe of the contact sensor 1018 from the mouth of the human or animal, places the probe of the contact sensor 1018 into the receiver and reads the displayed temperature on the display device 1104.

Method Implementations

In the previous section, apparatus of the operation of an implementation was described. In this section, the particular methods performed by a hand-held medical device and a mobile device of such an implementation are described by reference to a series of flowcharts in FIG. 39-43. In this section, the particular methods performed by apparatus 1100, 1200, 1400, 1400 and 1600 of such an implementation are described by reference to a series of flowcharts in FIG. 44-49.

FIG. 39-40 are a series of sequence diagrams of the interaction between a mobile device and a hand-held medical device, according to an implementation.

In FIG. 39, the hand-held medical device is connected to a mobile device via a wireless connection (such as a Bluetooth® wireless connection) or a USB cable or other cable, at block 3902. Bluetooth® is a proprietary open wireless technology standard for exchanging data over short distances (using short-wavelength radio transmissions in the ISM band from 2400-2480 MHz) from fixed and mobile devices, creating personal area networks (PANs) with high levels of security. Created by telecoms vendor Ericsson in 2794, Bluetooth® was originally conceived as a wireless alternative to RS-232 data cables. It can connect several devices, overcoming problems of synchronization. Bluetooth® uses a radio technology called frequency-hopping spread spectrum, which chops up the data being sent and transmits chunks of it on up to 79 bands (1 MHz each; centered from 2402 to 2480 MHz) in the range 2,400-2,483.5 MHz (allowing for guard bands). This range is in the globally unlicensed Industrial, Scientific and Medical (ISM) 2.4 GHz short-range radio frequency band. It usually performs 800 hops per second, with AFH enabled. Originally Gaussian frequency-shift keying (GFSK) modulation was the only modulation scheme available subsequently, since the introduction of Bluetooth 2.0+EDR, π/4-DQPSK and 8DPSK modulation may also be used between compatible devices. Devices functioning with GFSK are said to be operating in basic rate (BR) mode where an instantaneous data rate of 1 Mbit/s is possible. The term Enhanced Data Rate (EDR) is used to describe π/4-DPSK and 8DPSK schemes, each giving 2 and 3 Mbit/s respectively. The combination of these (BR and EDR) modes in Bluetooth® radio technology is classified as a "BR/EDR radio". Bluetooth® is a packet-based protocol with a master-slave structure. One master may communicate with up to 7 slaves in a piconet; all devices share the master's clock. Packet exchange is based on the basic clock, defined by the master, which ticks at 312.5 μs intervals. Two clock ticks make up a slot of 625 μs; two slots make up a slot pair of 1250 μs. In the simple case of single-slot packets the master transmits in even slots and receives in odd slots; the slave, conversely, receives in even slots and transmits in odd slots. Packets may be 1, 3 or 5 slots long but in all cases the master transmit will begin in even slots and the slave transmit in odd slots. Bluetooth® provides a secure way to connect and exchange information between devices such as faxes, mobile phones, telephones, laptops, personal computers, printers, Global Positioning System (GPS) receivers, digital cameras, and video game consoles.

In FIG. 39, the hand-held medical device recognizes the mobile device, at block 3904.

In FIG. 39, the hand-held medical device enters a calibration and diagnostic mode, at block 3906.

In FIG. 39, the hand-held medical device sends configuration data to the mobile device, at block 3908. One example of the configuration data is configuration data 908 in FIG. 9.

In FIG. 39, the mobile device downloads a calibration App, at block 3910. In general, an App of a mobile device is a software application that is executable on the mobile device. In some implementations, an app is stored on RAM 5106 or flash memory 5108 and executed (performed) by main processor 5102 in FIG. 51. The calibration App includes computer-executable instructions that In FIG. 39, the mobile device recognizes the hand-held medical device, at block 3912. In FIG. 39, the mobile device starts execution of the calibration App, at block 3914. In FIG. 39, the calibration App of the mobile device receives configuration data from the hand-held medical device, at block 3916. In FIG. 39, the calibration App of the mobile device presents navigation menus and receiving selection of the hand-held medical device, at block 3918.

In FIG. 39, the mobile device generates diagnostic instructions for the selected hand-held medical device, at block 3920. The diagnostic instructions are generated specifically for the hand-held medical device. One example of the diagnostic instructions are diagnostic instructions 910 in FIG. 9.

In FIG. 39, the mobile device transmits the generated diagnostic instructions to the selected hand-held medical device, at block 3922.

In FIG. 39, the hand-held medical device receives the generated diagnostic instructions for the hand-held medical device from the mobile device, at block 3924.

In FIG. 39, the hand-held medical device performing the generated diagnostic instructions, at block 3926. The performance of the generated diagnostic instructions yields diagnostic results. One example of the diagnostic results are the diagnostic results 912 in FIG. 9.

In FIG. 39, the hand-held medical device transmits the results of the performed diagnostic instructions to the mobile device, at block 3928.

In FIG. 39, the mobile device receives the results of the performed diagnostic instructions from the hand-held medical device, at block 3930. One example of the diagnostic results are the diagnostic results 912 in FIG. 9.

In FIG. 39, the mobile device generates calibration instructions for the selected hand-held medical device, at block 3932.

In FIG. 39, the mobile device transmits the generated calibration instructions to the selected hand-held medical device, at block 3934. One example of the calibration instructions are calibration instructions 914 in FIG. 9.

In FIG. 40, the hand-held medical device receives generated calibration instructions for the hand-held medical device from the mobile device, at block 3936. One example of the calibration instructions are calibration instructions 914 in FIG. 9.

In FIG. 40, the hand-held medical device performs the generated calibration instructions, yielding results of performed calibration instructions, at block 1138. One example of the calibration results are the calibration results 916 in FIG. 9.

In FIG. 40, the hand-held medical device transmits the results of the performed calibration instructions to the mobile device, at block 3940.

In FIG. 40, the mobile device receives the results of the performed calibration instructions from the hand-held medical device, at block 3942. One example of the calibration results are the calibration results 916 in FIG. 9.

In FIG. 40, the mobile device stores the results of the performed calibration instructions and the GPS location of the mobile device and the date/time, at block 3944.

In FIG. 40, the mobile device transmits through the Cloud a notice of the completed calibration and the date/time to the compliance office, at block 3946.

Figure 41:
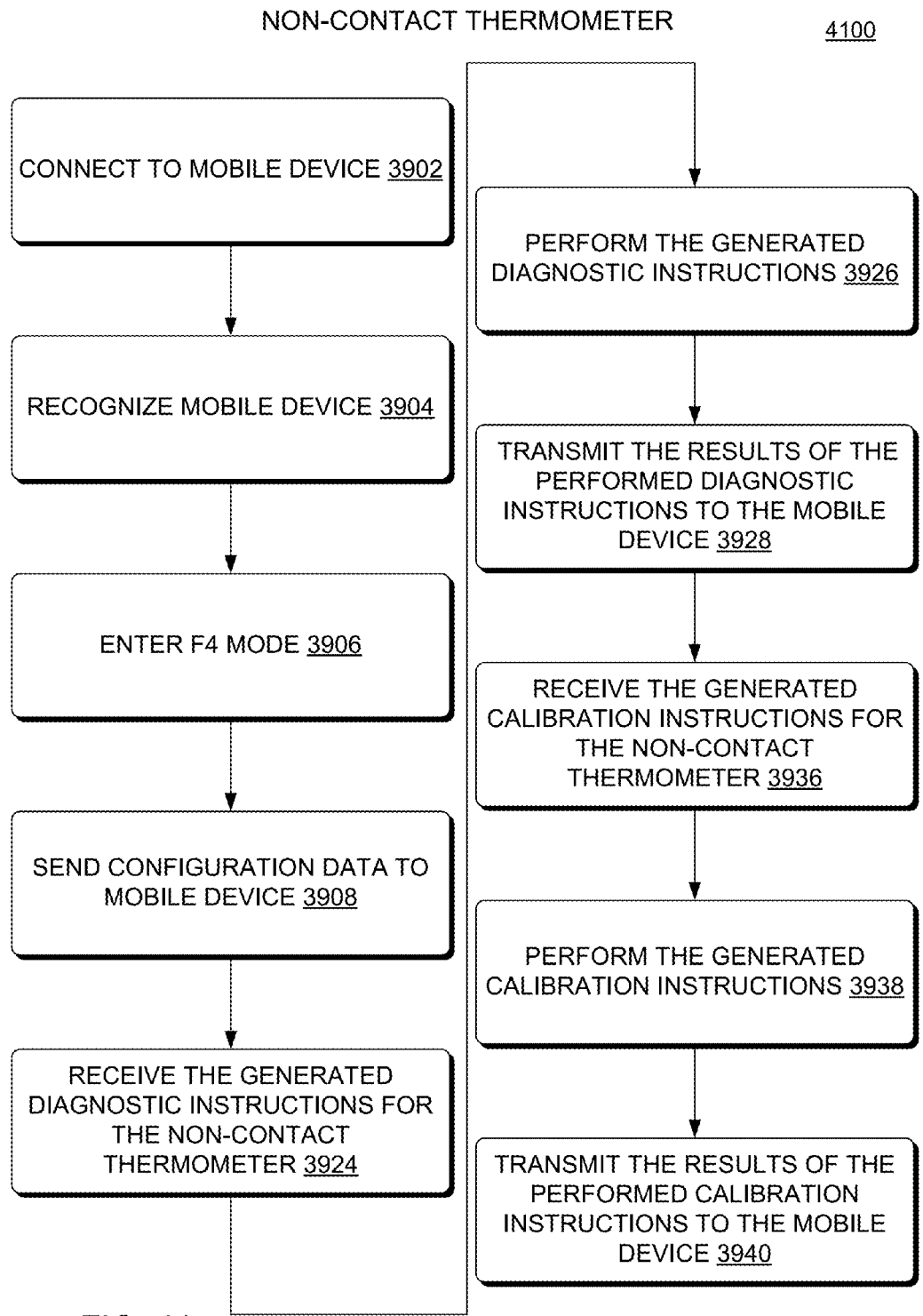
FIG. 41 is a flowchart of a method of calibrating a hand-held medical device that is in communication with a mobile device, the method performed by the hand-held medical device, according to an implementation.

FIG. 41 is a flowchart of a method 4100 of calibrating a hand-held medical device that is in communication with a mobile device, the method 4100 performed by the hand-held medical device, according to an implementation. The hand-held medical device 904 is one example of the hand-held medical device in FIG. 41. The mobile device 906 is one example of the mobile device in FIG. 41.

In some implementations, method 4100 includes connecting to a mobile device via a wireless connection (such as a Bluetooth® wireless connection) or a USB cable or other cable, at block 3902.

In some implementations, method 4100 includes recognizing the mobile device, at block 3904.

In some implementations, method 4100 includes entering calibration and diagnostic mode, at block 3906.

In some implementations, method 4100 includes sending configuration data to the mobile device, at block 3908. One example of the configuration data is configuration data 908 in FIG. 9.

In some implementations, method 4100 includes receiving generated diagnostic instructions for the hand-held medical device from the mobile device, at block 3924. The diagnostic instructions are generated specifically for the hand-held medical device. One example of the diagnostic instructions are diagnostic instructions 910 in FIG. 9.

In some implementations, method 4100 includes the hand-held medical device performing the generated diagnostic instructions, at block 3926. The performance of the generated diagnostic instructions yields diagnostic results. One example of the diagnostic results are the diagnostic results 912 in FIG. 9.

In some implementations, method 4100 includes transmitting the results of the performed diagnostic instructions to the mobile device, at block 3928.

In some implementations, method 4100 includes receiving generated calibration instructions for the hand-held medical device from the mobile device, at block 3936. One example of the calibration instructions are calibration instructions 914 in FIG. 9.

In one example of the calibration instructions that includes manual steps follows:
1. 
    Turn the hand-held medical device on
2. Set Mode to Surface Temp
3. Make temperature measurement of a Black body temperature
    a. Set and equilibrate the black body to the desired temperature (for example 30.039 C.)
    b. Take a temperature measurement of the black body using the IR thermometer in "Surface Temp" mode
    c. Record reading
    d. If the thermometer reading does not match the black body temperature follow the steps in #3 to adjust the thermometer reading
4. Setting the thermometer to "Surface Temp Mode" using the calibration tool
    a. Receive indication that the operator of the device has pressed "Prog Setting" button and held 3 seconds until F1 is displayed
    b. Receive indication that the operator of the device has pressed "Prog Setting" button twice to go to F3
    c. Verify that F3 is set to "1" (Surface Temp) i. If "0" is displayed push the "+" button on the calibration tool
    d. Confirm the F3 setting by pressing the "Prog Setting" button
    e. Receive indication that the operator of the device has pressed "Prog Setting" button again to go to F4
    f. Receive indication that the operator of the device has pressed the "+" or "−" buttons on the calibration tool adjust the temperature reading. The buttons to increase or reduce the thermometer's temperature reading that will be displayed.
  g. When desired adjustment is reached, receiving confirmation of the operator pressing the "Prog Setting" button h. The display will go off and the device is ready to make temperature readings.
5. Repeat steps in #3 until the thermometer reading matches the black body temperature
6. Re-set thermometer back to "Body" before sending to next manufacturing step. Note: the IR thermometer is calibrated in the "Surface Temp" mode because it is used to measure the surface temperature of the black body. Do not carry out calibration in any other mode or body temperature measurements will be affected. Different algorithms are used to calculate the temperature displayed based on temperature measurement mode setting.

In some implementations, method 4100 includes performing the generated calibration instructions, yielding results of performed calibration instructions, at block 3938. One example of the calibration results are the calibration results 916 in FIG. 9.

In some implementations, method 4100 includes transmitting the results of the performed calibration instructions to the mobile device, at block 3940.

Figure 42:
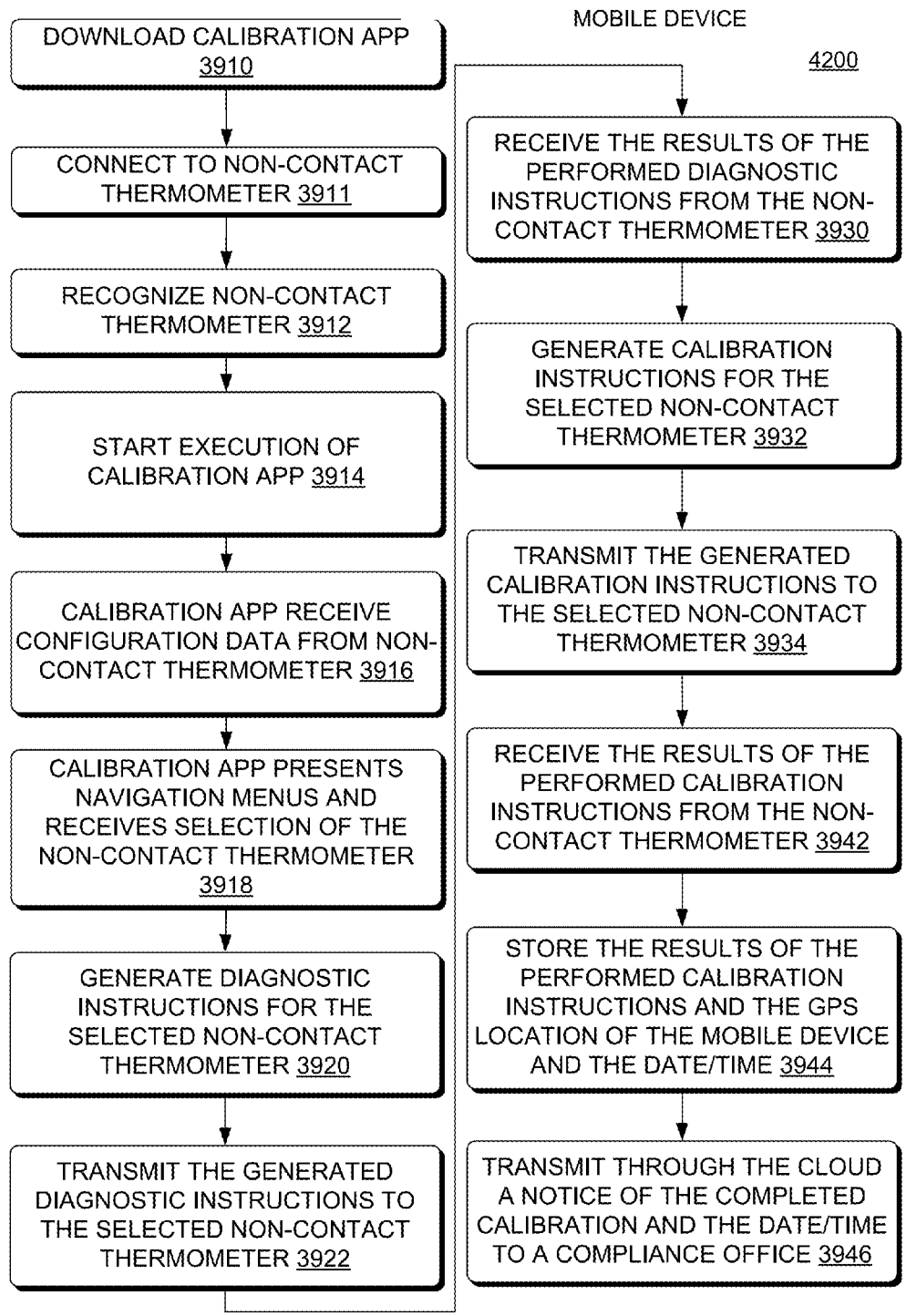
FIG. 42 is a flowchart of a method of calibrating a hand-held medical device that is in communication with a mobile device, the method is performed by the mobile device, according to an implementation.

FIG. 42 is a flowchart of a method 4200 of calibrating a hand-held medical device that is in communication with a mobile device, the method 4200 is performed by the mobile device, according to an implementation.

In some implementations, method 4200 includes downloading a calibration App, at block 3910.

In some implementations, method 4200 includes connecting to the hand-held medical device via a wireless connection (such as a Bluetooth® wireless connection) or a USB cable or other cable, at block 3911.

In some implementations, method 4200 includes recognizing the hand-held medical device, at block 3912.

In some implementations, method 4200 includes starting execution of the calibration App, at block 3914.

In some implementations, method 4200 includes the calibration App receiving configuration data from hand-held medical device, at block 3916.

In some implementations, method 4200 includes the calibration App presenting navigation menus and receiving selection of the hand-held medical device, at block 3918.

In some implementations, method 4200 includes generating diagnostic instructions for the selected hand-held medical device, at block 3920. One example of the diagnostic instructions are diagnostic instructions 910 in FIG. 9.

In some implementations, method 4200 includes transmitting the generated diagnostic instructions to the selected hand-held medical device, at block 3922.

In some implementations, method 4200 includes receiving the results of the performed diagnostic instructions from the hand-held medical device, at block 3930. One example of the diagnostic results is the diagnostic results 912 in FIG. 9.

In some implementations, method 4200 includes generating calibration instructions for the selected hand-held medical device, at block 3932.

In some implementations, method 4200 includes transmitting the generated calibration instructions to the selected hand-held medical device, at block 3934. One example of the calibration instructions are calibration instructions 914 in FIG. 9.

In some implementations, method 4200 includes receiving the results of the performed calibration instructions from the hand-held medical device, at block 3942. One example of the calibration results are the calibration results 916 in FIG. 9.

In some implementations, method 4200 includes storing the results of the performed calibration instructions and the GPS location of the mobile device and the date/time, at block 3944.

In some implementations, method 4200 includes transmitting through the Cloud a notice of the completed calibration and the date/time to the compliance office, at block 3946.

Figure 43:
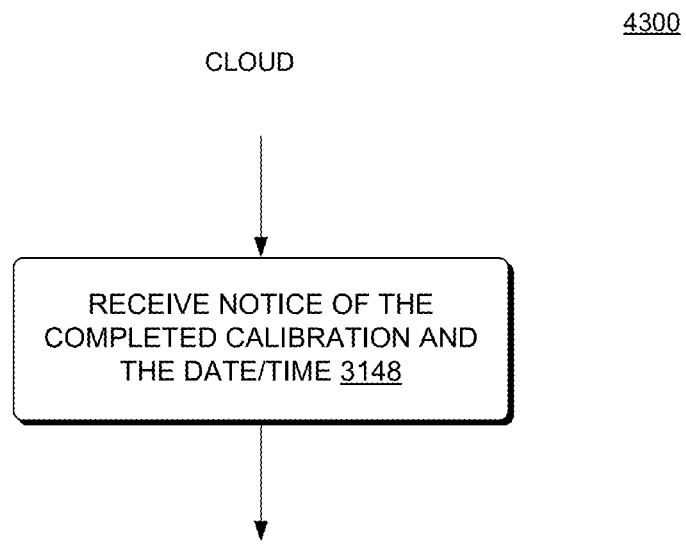
FIG. 43 is a flowchart of a method of a mobile device receiving notice of the completed calibration and the date/time of the hand-held medical device.

FIG. 43 is a flowchart of a method 4300 of a mobile device receiving notice of the completed calibration and the date/time of the hand-held medical device, at block 3948. The hand-held medical device 904 is one example of the hand-held medical device in FIG. 43. The mobile device 906 is one example of the mobile device in FIG. 42.

FIG. 44 is a flowchart of a method 4400 to measure temperature from multiple source points. Method 4400 includes sensing electromagnetic energy at a plurality of external source points on a subject, at block 4402. The sensing at block 4400 yields a sensed electromagnetic energy of the plurality of external source points. In one implementation, block 4402 includes sensing the electromagnetic energy from only at the tympanic membrane surface source point on the subject and sensing the electromagnetic energy at no other point on the subject.

Method 4400 also includes correlating a temperature of the subject from the sensed electromagnetic energy of the plurality of external source points, at block 4404. The correlating at block 4404 yields a correlated temperature. In some implementations, the correlating at block 4404 is performed by the multi-source temperature correlator 1112 in FIG. 11. In some implementations, block 4404 includes correlating only the temperature of the subject from the sensed electromagnetic energy of the tympanic membrane surface source point on the subject. In one implementation, block 4404 includes correlating the electromagnetic energy from only the tympanic membrane surface source point on the subject and correlating the electromagnetic energy at no other point on the subject.

FIG. 45 is a flowchart of a method 4500 to measure temperature of a forehead and a tympanic membrane surface, according to an implementation. Method 4500 includes sensing the electromagnetic energy at the tympanic membrane surface source point on the subject and/or the forehead source point on the subject, at block 4502. In one implementation, block 4502 includes sensing the electromagnetic energy from only at the tympanic membrane surface source point on the subject and sensing the electromagnetic energy at no other point on the subject. The sensing at block 4502 yields the sensed electromagnetic energy of the external source point(s).

Method 4500 also includes correlating the temperature of the subject from the sensed electromagnetic energy of the tympanic membrane surface source point on the subject and/or from the forehead source point on the subject, at block 4504. The correlating at block 4504 yields a correlated temperature. In some implementations, block 4504 includes correlating only the temperature of the subject from the sensed electromagnetic energy of the tympanic membrane surface source point on the subject. In some implementations, the correlating at block 4504 is performed by the multi-source temperature correlator 1112 in FIG. 11. In one implementation, block 4504 includes correlating the electromagnetic energy from only the tympanic membrane surface source point on the subject and correlating the electromagnetic energy at no other point on the subject.

In some implementations of method 4400 and 4500, the correlated temperature of the subject includes only a core temperature of the subject, an axillary temperature of the subject, a rectal temperature of the subject and an oral temperature of the subject. Methods 4400 and 4500 permit an operator to take the temperature of a subject at multiple locations on a patient and from the temperatures at multiple locations to determine the temperature at a number of other locations of the subject. The multiple source points of which the electromagnetic energy is sensed are mutually exclusive to the location of the correlated temperature. In one example, the tympanic membrane surface source point on the subject and a forehead source point are mutually exclusive to the core temperature of the subject, an axillary temperature of the subject, a rectal temperature of the subject and an oral temperature of the subject.

The correlation of action 4404 in FIG. 44 and action 4504 can include a calculation based on Formula 1:

$$T_{body} = |f_{stb}(T_{surface\ temp} + f_{ntc}(T_{ntc})) + F4_{body}|$$ Formula 1 where $T_{body}$ is the temperature of a body or subject
where $f_{stb}$ is a mathematical formula of a surface of a body
where $f_{ntc}$ is mathematical formula for ambient temperature reading
where $T_{surface\ temp}$ is a surface temperature determined from the sensing 4402 in FIG. 4400 or 4502 in FIG. 45.
where $T_{ntc}$ is an ambient air temperature reading
where $F4_{body}$ is a calibration difference in axillary mode, which is stored or set in a memory of the apparatus either during manufacturing or in the field. The apparatus also sets, stores and retrieves $F4_{oral}$, $F4_{core}$, and $F4_{rectal}$ in the memory.
$f_{ntc}(T_{ntc})$ is a bias in consideration of the temperature sensing mode. For example $f_{axillary}(T_{axillary}) = 0.2°$ C., $f_{oral}(T_{oral}) = 0.4°$ C., $f_{rectal}(T_{rectal}) = 0.5°$ C. and $f_{core}(T_{core}) = 0.3°$ C.

FIG. 46 is a flowchart of a method 4600 of a method of determining correlated body temperature of tympanic membrane surface, according to an implementation.

Method 4600 includes determining a correlated body temperature of tympanic membrane surface by biasing a sensed temperature of a tympanic membrane surface, at block 4602. In one example, the sensed temperature is biased by +0.5° C. to yield the correlated body temperature. In another example, the sensed temperature is biased by −0.5° C. to yield the correlated body temperature. Method 4600 in FIG. 46 is one example of block 4404 in FIG. 44 and block 4504 in FIG. 45. An example of correlating body temperature of a tympanic membrane surface follows:

$f_{ntc}(T_{ntc}) = 0.2°$ C. when $T_{ntc} = 26.2°$ C. as retrieved from a data table for body sensing mode.

assumption: $T_{surface\ temp} = 37.8°$ C.

$T_{surface\ temp} + f_{ntc}(T_{ntc}) = 37.8°$ C. +0.2° C. = 38.0° C.

$f_{stb}(T_{surface\ temp} + f_{ntc}(T_{ntc})) = 38°$ C. +1.4° C. = 39.4° C.

assumption: $F4_{body} = 0.5°$ C.

$T_{body} = |f_{stb}(T_{surface\ temp} + f_{ntc}(T_{ntc})) + F4_{body}| = |39.4°$ C. +0.5 C| = 39.9° C.

The correlated temperature for the tympanic membrane surface is 40.0° C.

Figure 47:
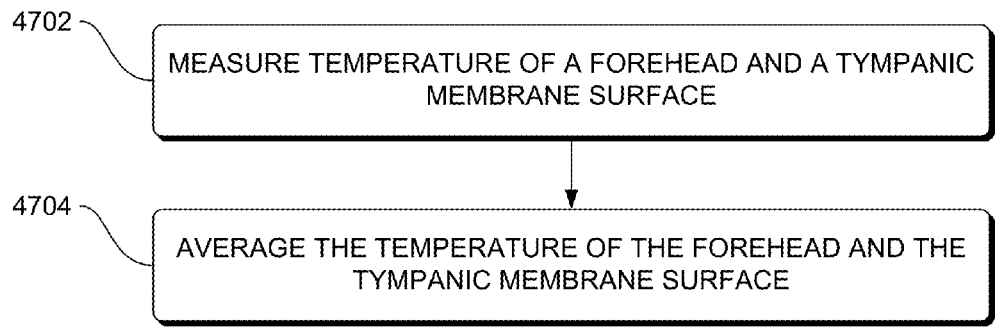
FIG. 47 is a flowchart of a method of forehead and tympanic membrane surface sensing, according to an implementation.

FIG. 47 is a flowchart of a method 4700 of forehead and tympanic membrane surface sensing, according to an implementation.

Method 4700 includes measuring temperature of a forehead and a tympanic membrane surface, at block 4702.

Method 4400 in FIG. 44 is one example of block 4702. In an example of correlating temperature of a plurality of external locations, such as a forehead and a tympanic membrane surface to an axillary temperature, first a forehead temperature is calculated using formula 1 as follows:

$f_{ntc}(T_{ntc}) = 0.2°$ C. when $T_{ntc} = 26.2°$ C. as retrieved from a data table for axillary sensing mode.

assumption: $T_{surface\ temp} = 37.8°$ C.

$T_{surface\ temp} + f_{ntc}(T_{ntc}) = 37.8°$ C. +0.2° C. = 38.0° C.

$f_{stb}(T_{surface\ temp} + f_{ntc}(T_{ntc})) = 38°$ C. +1.4° C. = 39.4° C.

assumption: $F4_{body} = 0°$ C.

$T_{body} = |f_{stb}(T_{surface\ temp} + f_{ntc}(T_{ntc})) + F4_{body}| = |39.4°$ C. +0 C| = 39.4° C.

And second, a tympanic temperature is calculated using formula 1 as follows:

$f_{ntc}(T_{ntc}) = 0.6°$ C. when $T_{ntc} = 26.4°$ C. as retrieved from a data table.

assumption: $T_{surface\ temp} = 38.0°$ C.

$T_{surface\ temp} + f_{ntc}(T_{ntc}) = 38.0°$ C. +0.6° C. = 38.6° C.

$f_{stb}(T_{surface\ temp} + f_{ntc}(T_{ntc})) = 38.6°$ C. +1.4 C = 40.0° C.

assumption: $F4_{body} = 0°$ C.

$T_{body} = |f_{stb}(T_{surface\ temp} + f_{ntc}(T_{ntc})) + F4_{body}| = |40.0°$ C. +0 C| = 40.0° C.

Thereafter the correlated temperature for the forehead (39.4° C.) and the correlated temperature for the tympanic membrane surface (40.0° C.) are averaged, at block 3904, yielding the final result of the scan of the forehead and the tympanic membrane surface as 39.7° C.

Figure 48:
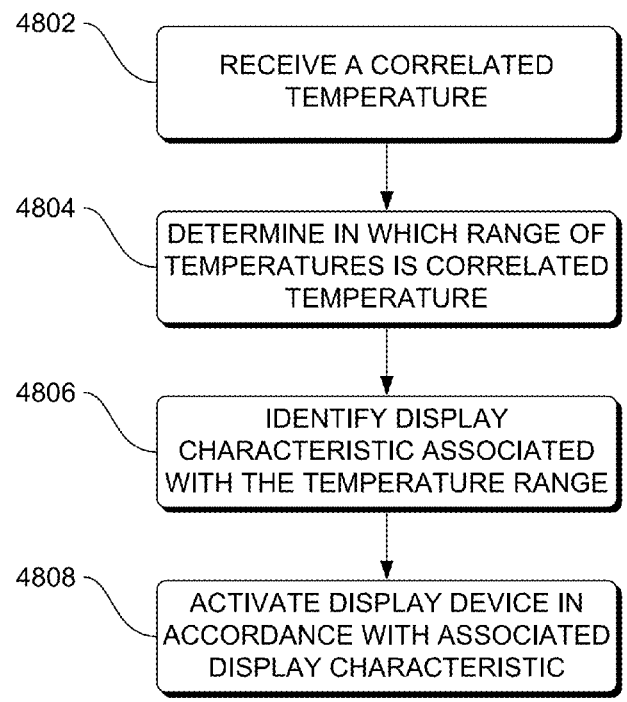
FIG. 48 is a flowchart of a method to display temperature color indicators, according to an implementation.

FIG. 48 is a flowchart of a method 4800 to display temperature color indicators, according to an implementation. Method 4800 provides color rendering in the display device 904 to indicate a general range of a correlated temperature.

Method 4800 includes receiving a correlated temperature, at block 4802. The correlated temperature can be received from the non-contact sensor 1110 or the contact sensor 1312, or the correlated temperature can be received from a printed circuit board that has adjusted a temperature in reference to either the site on the human or animal of the temperature sensing and or the ambient temperature detected in the vicinity of the apparatus performing the method 4800.

Method 4800 also includes determining in which of a plurality of ranges is the correlated temperature, at block 4804.

Method 4800 also includes identifying a display characteristic that is associated with the determined temperature range, at block 4806. In some implementations, the display characteristic is a color of text. In some implementations, the display characteristic is an image such as a commercial advertisement image.

Method 4800 also includes activating the display device 1104 in accordance with the identified display characteristic, at block 4808. In the implementations in which the display characteristic is a color of text, method 4800 provides color rendering in the display device 1104 to indicate the general range of the sensed temperature. The medical significance of the temperature is indicated by the displayed color. In the implementations in which the display characteristic is an image such as a commercial advertisement image, method 4800 provides advertising that is relevant to the medical condition of a patient.

In one implementation of a method to display temperature color indicators, according to an implementation of two colors, the method includes the non-contact sensor (such as 1004 in FIG. 10) yielding a sensed temperature that is correlated and color changes of the display device (such as 1104 in FIG. 11) are related to the correlated temperature, and the display device activates pixels in at least two colors, the colors being in accordance with the correlated temperature.

Figure 49:
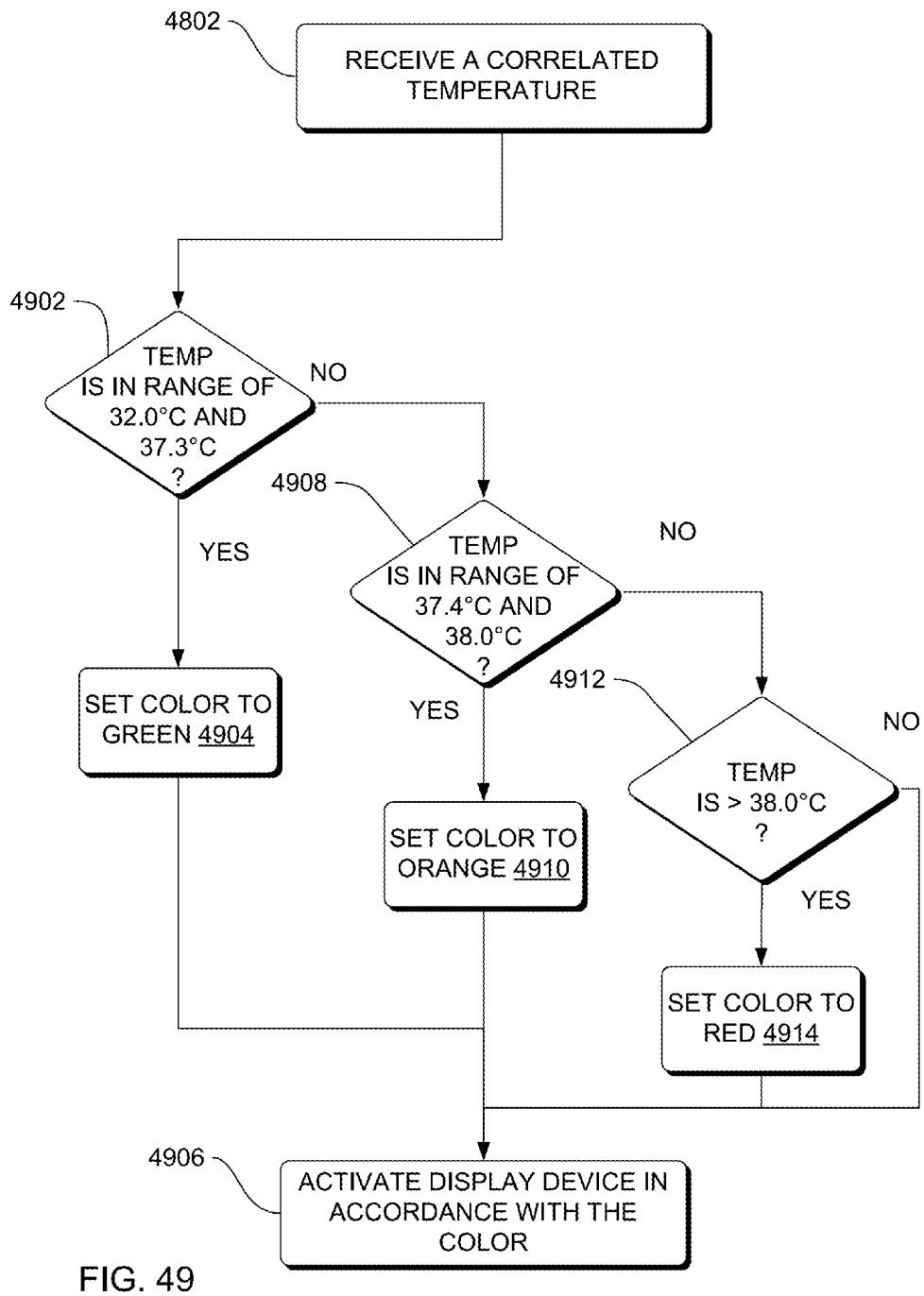
FIG. 49 is a flowchart of a method to display temperature color indicators, according to an implementation of three colors.

FIG. 49 is a flowchart of a method 4900 to display temperature color indicators, according to an implementation of three colors. Method 4900 provides color rendering in the display device 1104 to indicate a general range of a correlated temperature.

Method 4900 includes receiving a correlated temperature, at block 2502. The correlated temperature can be received from the non-contact sensor 1004 or the contact sensor 1312, or the correlated temperature can be received from a printed circuit board that has adjusted a temperature in reference to either the site on the human or animal of the temperature sensing and or the ambient temperature detected in the vicinity of the apparatus performing the method 4900.

Method 4900 also includes determining whether or not the correlated temperature is in the range of 32.0° C. and 37.3° C., at block 4902. If the correlated temperature is in the range of 32.0° C. and 37.3° C., then the color is set to 'green' to indicate a temperature of no medical concern, at block 4904 and the background of the display device 1104 is activated in accordance with the color, at block 4906.

If the correlated temperature is not the range of 32.0° C. and 37.3° C., then method 4900 also includes determining whether or not the correlated temperature is in the range of 37.4° C. and 38.0° C., at block 4908. If the sensed temperature is in the range of 37.4° C. and 38.0° C., then the color is set to 'orange' to indicate caution, at block 4910 and the background of the display device 1104 is activated in accordance with the color, at block 4906.

If the correlated temperature is not the range of 37.4° C. and 38.0° C., then method 4900 also includes determining whether or not the correlated temperature is over 38.0° C., at block 4912. If the correlated temperature is over 38.0° C., then the color is set to 'red' to indicate alert, at block 4912 and the background of the display device 1104 is activated in accordance with the color, at block 4906.

Method 4900 assumes that temperature is correlated in gradients of 10ths of a degree. Other temperature range boundaries are used in accordance with other gradients of temperature sensing.

In some implementations, some pixels in the display device 1104 are activated as a green color when the correlated temperature is between 36.3° C. and 37.3° C. (97.3° F. to 99.1° F.), some pixels in the display device 1104 are activated as an orange color when the correlated temperature is between 37.4° C. and 37.9° C. (99.3° F. to 100.2° F.), some pixels in the display device 1104 are activated as a red color when the correlated temperature is greater than 38° C. (100.4° F.). In some implementations, the display device 1104 is a backlit LCD screen (which is easy to read in a dark room) and some pixels in the display device 1104 are activated (remain lit) for about 5 seconds after the button 1104 is released. After the display device 1104 has shut off, another temperature reading can be taken by the apparatus. The color change of the display device 1104 is to alert the user of the apparatus of a potential increase of body temperature of the human or animal subject. Temperature reported on the display can be used for treatment decisions.

In some implementations, methods 4100-5000 are implemented as a sequence of instructions which, when executed by a processor 5302 in FIG. 53, cause the processor to perform the respective method. In other implementations, methods 4100-5000 are implemented as a computer-accessible medium having executable instructions capable of directing a processor, such as processor 5302 in FIG. 53, to perform the respective method. In varying implementations, the medium is a magnetic medium, an electronic medium, or an optical medium.

Figure 50:
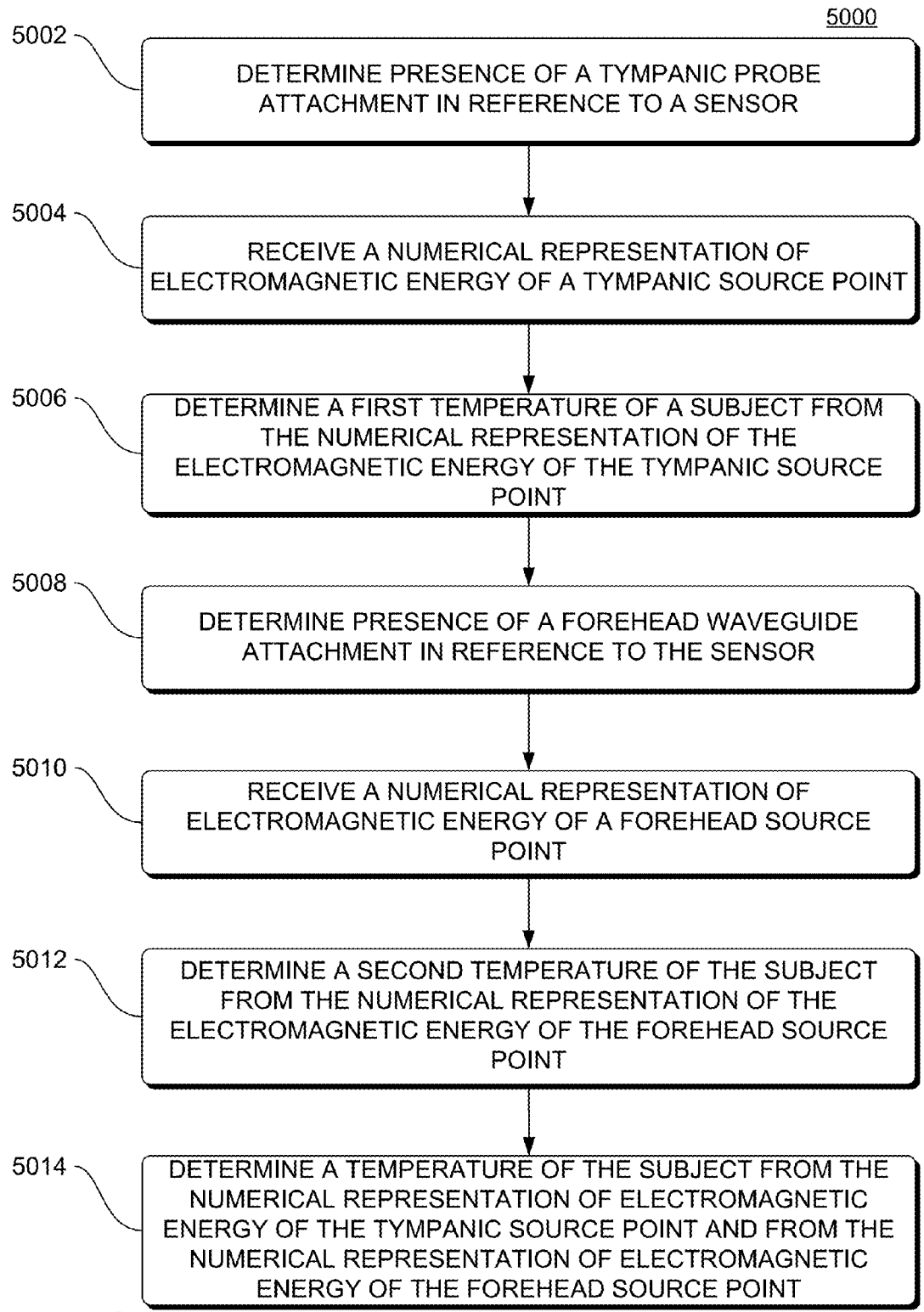
FIG. 50 is a flowchart of a method to control a dual tympanic and forehead electronic thermometer, according to an implementation.

FIG. 50 is a flowchart of a method 5000 to control a dual tympanic and forehead electronic thermometer, according to an implementation of three colors. Method 5000 provides a temperature of a subject based in both tympanic and forehead non-contact sensor readings.

Some implementations of method 5000 includes determining presence of a tympanic probe on a sensor, at block 5002.

In response to the determining of the presence of the tympanic probe at block 5002, method 5000 includes receiving a numerical representation of electromagnetic energy of a tympanic source point, at block 5004.

In response to receiving the numerical representation of the electromagnetic energy of the tympanic source point at block 5004, method 5000 determining a first temperature of a subject from the numerical representation of the electromagnetic energy of the tympanic source point, at block 5006.

Some implementations of method 5000 also includes determining presence of a forehead waveguide attachment in reference to the sensor, at block 5008.

In response to the determining of the presence of the forehead waveguide attachment at block 5008, method 5000 includes receiving a numerical representation of electromagnetic energy of a forehead source point, at block 5010. Numerical representation of electromagnetic energy from no other source points is received in method 5000.

In response to receiving the numerical representation of the electromagnetic energy of the forehead source point at block 5010, method includes determining a second temperature of the subject from the numerical representation of the electromagnetic energy of the forehead source point, at block 5012.

Method 5000 also includes determining a temperature of the subject from a numerical representation of electromagnetic energy of the tympanic source point and a numerical representation of electromagnetic energy of the forehead source point, at block 5014.

In method 5000, no source points other than the tympanic source point and the forehead source point are sensed, and no more than one sensor senses the tympanic source point and the forehead source point.

Hardware and Operating Environment

The implementations described herein generally relate to a mobile wireless communication device, hereafter referred to as a mobile device, which can be configured according to an IT policy. It should be noted that the term IT policy, in general, refers to a collection of IT policy rules, in which the IT policy rules can be defined as being either grouped or non-grouped and global or per-user. The terms grouped, non-grouped, global and per-user are defined further below. Examples of applicable communication devices include pagers, cellular phones, cellular smart-phones, wireless organizers, personal digital assistants, computers, laptops, handheld wireless communication devices, wirelessly enabled notebook computers and the like.

Figure 51:
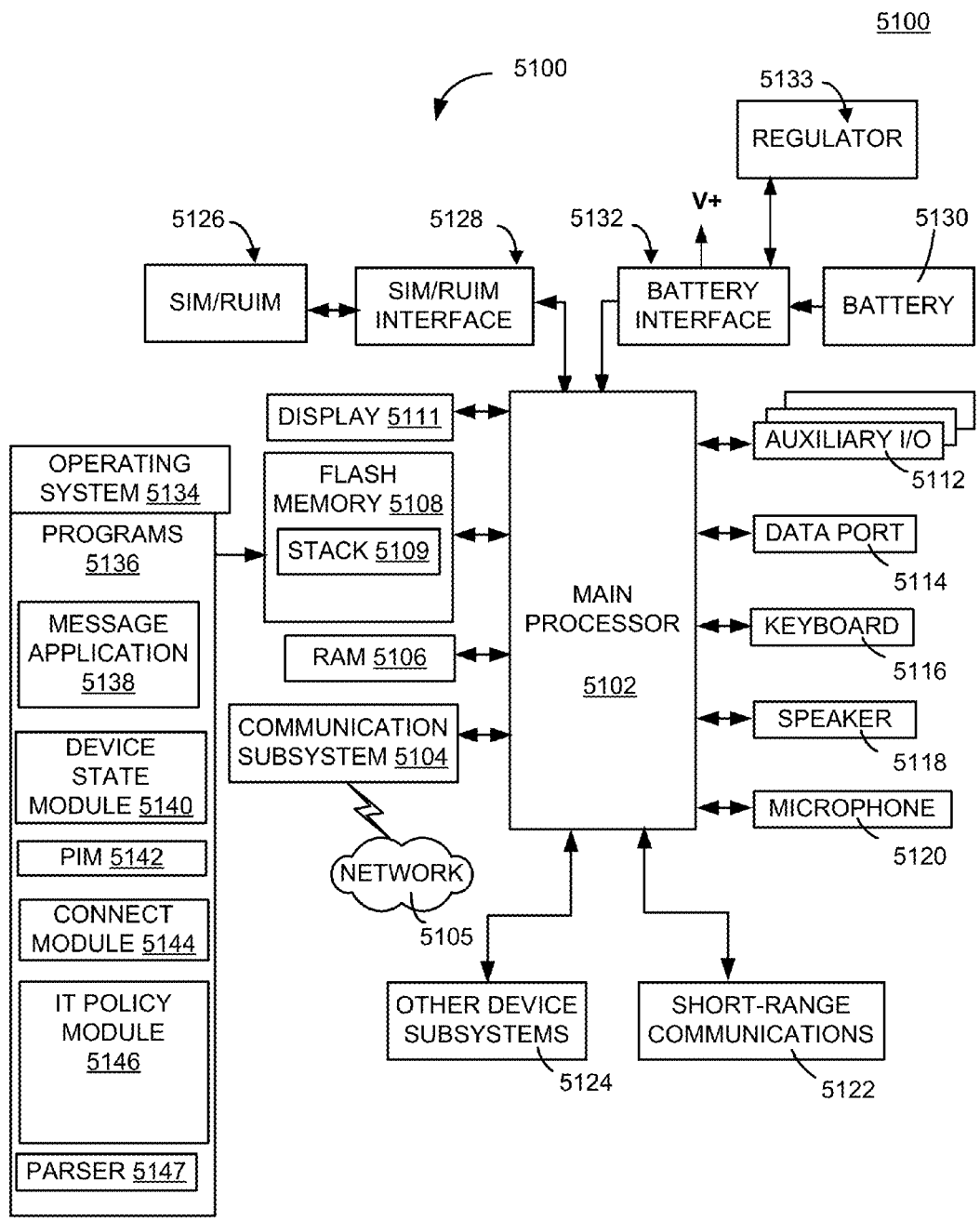
FIG. 51 is a block diagram of a mobile device, according to an implementation.

FIG. 51 is a block diagram of a mobile device 5100, according to an implementation. The mobile device is a two-way communication device with advanced data communication capabilities including the capability to communicate with other mobile devices or computer systems through a network of transceiver stations. The mobile device may also have the capability to allow voice communication. Depending on the functionality provided by the mobile device, it may be referred to as a data messaging device, a two-way pager, a cellular telephone with data messaging capabilities, a wireless Internet appliance, or a data communication device (with or without telephony capabilities).

Mobile device 5100 is one implementation of mobile device 906 in FIG. 9. The mobile device 5100 includes a number of components such as a main processor 5102 that controls the overall operation of the mobile device 5100. Communication functions, including data and voice communications, are performed through a communication subsystem 5104. The communication subsystem 5104 receives messages from and sends messages to wireless networks 5105. Other implementations of the mobile device 5100, the communication subsystem 5104 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 5104 with the wireless network 5105 represents one or more different Radio Frequency (RF) channels. With newer network protocols, these channels are capable of supporting both circuit switched voice communications and packet switched data communications.

The main processor 5102 also interacts with additional subsystems such as a Random Access Memory (RAM) 5106, a flash memory 5108, a display 5110, an auxiliary input/output (I/O) subsystem 5112, a data port 5114, a keyboard 5116, a speaker 5118, a microphone 5120, short-range communications 5122 and other device subsystems 5124. The configuration data 908, the diagnostic results 912 and the calibration results 916 is received by the communication subsystem 5104 and transferred by the main processor 5102 to the flash memory 5108. The diagnostic instructions 910 and the calibration instructions 914 are also transferred by the main processor 5102 from the flash memory 5108 through the cable 902.

Some of the subsystems of the mobile device 5100 perform communication-related functions, whereas other subsystems may provide "resident" or on-device functions. By way of example, the display 5110 and the keyboard 5116 may be used for both communication-related functions, such as entering a text message for transmission over the wireless network 5105, and device-resident functions such as a calculator or task list.

The mobile device 5100 can transmit and receive communication signals over the wireless network 5105 after required network registration or activation procedures have been completed. Network access is associated with a subscriber or user of the mobile device 5100. To identify a subscriber, the mobile device 5100 requires a SIM/RUIM card 5126 (i.e. Subscriber Identity Module or a Removable User Identity Module) to be inserted into a SIM/RUIM interface 5128 in order to communicate with a network. The SIM card or RUIM 5126 is one type of a conventional "smart card" that can be used to identify a subscriber of the mobile device 5100 and to personalize the mobile device 5100, among other things. Without the SIM card 5126, the mobile device 5100 is not fully operational for communication with the wireless network 5105. By inserting the SIM card/RUIM 5126 into the SIM/RUIM interface 5128, a subscriber can access all subscribed services. Services may include: web browsing and messaging such as e-mail, voice mail, Short Message Service (SMS), and Multimedia Messaging Services (MMS). More advanced services may include: point of sale, field service and sales force automation. The SIM card/RUIM 5126 includes a processor and memory for storing information. Once the SIM card/RUIM 5126 is inserted into the SIM/RUIM interface 5128, it is coupled to the main processor 5102. In order to identify the subscriber, the SIM card/RUIM 5126 can include some user parameters such as an International Mobile Subscriber Identity (IMSI). An advantage of using the SIM card/RUIM 5126 is that a subscriber is not necessarily bound by any single physical mobile device. The SIM card/RUIM 5126 may store additional subscriber information for a mobile device as well, including datebook (or calendar) information and recent call information. Alternatively, user identification information can also be programmed into the flash memory 5108.

The mobile device 5100 is a battery-powered device and includes a battery interface 5132 for receiving one or more rechargeable batteries 5130. In one or more implementations, the battery 5130 can be a smart battery with an embedded microprocessor. The battery interface 5132 is coupled to a regulator 5133, which assists the battery 5130 in providing power V+ to the mobile device 5100. Although current technology makes use of a battery, future technologies such as micro fuel cells may provide the power to the mobile device 5100.

The mobile device 5100 also includes an operating system 5134 and software components 5136 to 5146 which are described in more detail below. The operating system 5134 and the software components 5136 to 5146 that are executed by the main processor 5102 are typically stored in a persistent store such as the flash memory 5108, which may alternatively be a read-only memory (ROM) or similar storage element (not shown). Those skilled in the art will appreciate that portions of the operating system 5134 and the software components 5136 to 5146, such as specific device applications, or parts thereof, may be temporarily loaded into a volatile store such as the RAM 5106. Other software components can also be included.

The subset of software applications 5136 that control basic device operations, including data and voice communication applications, will normally be installed on the mobile device 5100 during its manufacture. Other software applications include a message application 5138 that can be any suitable software program that allows a user of the mobile device 5100 to transmit and receive electronic messages. Various alternatives exist for the message application 5138 as is well known to those skilled in the art. Messages that have been sent or received by the user are typically stored in the flash memory 5108 of the mobile device 5100 or some other suitable storage element in the mobile device 5100. In one or more implementations, some of the sent and received messages may be stored remotely from the device 5100 such as in a data store of an associated host system with which the mobile device 5100 communicates.

The software applications can further include a device state module 5140, a Personal Information Manager (PIM) 5142, and other suitable modules (not shown). The device state module 5140 provides persistence, i.e. the device state module 5140 ensures that important device data is stored in persistent memory, such as the flash memory 5108, so that the data is not lost when the mobile device 5100 is turned off or loses power.

The PIM 5142 includes functionality for organizing and managing data items of interest to the user, such as, but not limited to, e-mail, contacts, calendar events, voice mails, appointments, and task items. A PIM application has the ability to transmit and receive data items via the wireless network 5105. PIM data items may be seamlessly integrated, synchronized, and updated via the wireless network 5105 with the mobile device subscriber's corresponding data items stored and/or associated with a host computer system. This functionality creates a mirrored host computer on the mobile device 5100 with respect to such items. This can be particularly advantageous when the host computer system is the mobile device subscriber's office computer system.

The mobile device 5100 also includes a connect module 5144, and an IT policy module 5146. The connect module 5144 implements the communication protocols that are required for the mobile device 5100 to communicate with the wireless infrastructure and any host system, such as an enterprise system, with which the mobile device 5100 is authorized to interface. Examples of a wireless infrastructure and an enterprise system are given in FIGS. 29 and 30, which are described in more detail below.

The connect module 5144 includes a set of APIs that can be integrated with the mobile device 5100 to allow the mobile device 5100 to use any number of services associated with the enterprise system. The connect module 5144 allows the mobile device 5100 to establish an end-to-end secure, authenticated communication pipe with the host system. A subset of applications for which access is provided by the connect module 5144 can be used to pass IT policy commands from the host system to the mobile device 5100. This can be done in a wireless or wired manner. These instructions can then be passed to the IT policy module 5146 to modify the configuration of the device 5100. Alternatively, in some cases, the IT policy update can also be done over a wired connection.

The IT policy module 5146 receives IT policy data that encodes the IT policy. The IT policy module 5146 then ensures that the IT policy data is authenticated by the mobile device 5100. The IT policy data can then be stored in the flash memory 5106 in its native form. After the IT policy data is stored, a global notification can be sent by the IT policy module 5146 to all of the applications residing on the mobile device 5100. Applications for which the IT policy may be applicable then respond by reading the IT policy data to look for IT policy rules that are applicable.

The IT policy module 5146 can include a parser 5147, which can be used by the applications to read the IT policy rules. In some cases, another module or application can provide the parser. Grouped IT policy rules, described in more detail below, are retrieved as byte streams, which are then sent (recursively) into the parser to determine the values of each IT policy rule defined within the grouped IT policy rule. In one or more implementations, the IT policy module 5146 can determine which applications are affected by the IT policy data and transmit a notification to only those applications. In either of these cases, for applications that are not being executed by the main processor 5102 at the time of the notification, the applications can call the parser or the IT policy module 5146 when they are executed to determine if there are any relevant IT policy rules in the newly received IT policy data.

All applications that support rules in the IT Policy are coded to know the type of data to expect. For example, the value that is set for the "WEP User Name" IT policy rule is known to be a string; therefore the value in the IT policy data that corresponds to this rule is interpreted as a string. As another example, the setting for the "Set Maximum Password Attempts" IT policy rule is known to be an integer, and therefore the value in the IT policy data that corresponds to this rule is interpreted as such.

After the IT policy rules have been applied to the applicable applications or configuration files, the IT policy module 5146 sends an acknowledgement back to the host system to indicate that the IT policy data was received and successfully applied.

Other types of software applications can also be installed on the mobile device 5100. These software applications can be third party applications, which are added after the manufacture of the mobile device 5100. Examples of third party applications include games, calculators, utilities, etc.

The additional applications can be loaded onto the mobile device 5100 through at least one of the wireless network 5105, the auxiliary I/O subsystem 5112, the data port 5114, the short-range communications subsystem 5122, or any other suitable device subsystem 5124. This flexibility in application installation increases the functionality of the mobile device 5100 and may provide enhanced on-device functions, communication-related functions, or both. For example, secure communication applications may enable electronic commerce functions and other such financial transactions to be performed using the mobile device 5100.

The data port 5114 enables a subscriber to set preferences through an external device or software application and extends the capabilities of the mobile device 5100 by providing for information or software downloads to the mobile device 5100 other than through a wireless communication network. The alternate download path may, for example, be used to load an encryption key onto the mobile device 5100 through a direct and thus reliable and trusted connection to provide secure device communication.

The data port 5114 can be any suitable port that enables data communication between the mobile device 5100 and another computing device. The data port 5114 can be a serial or a parallel port. In some instances, the data port 5114 can be a USB port that includes data lines for data transfer and a supply line that can provide a charging current to charge the battery 5130 of the mobile device 5100.

The short-range communications subsystem 5122 provides for communication between the mobile device 5100 and different systems or devices, without the use of the wireless network 5105. For example, the subsystem 5122 may include an infrared device and associated circuits and components for short-range communication. Examples of short-range communication standards include standards developed by the Infrared Data Association (IrDA), Bluetooth, and the 802.11 family of standards developed by IEEE.

In use, a received signal such as a text message, an e-mail message, or web page download will be processed by the communication subsystem 5104 and input to the main processor 5102. The main processor 5102 will then process the received signal for output to the display 5110 or alternatively to the auxiliary I/O subsystem 5112. A subscriber may also compose data items, such as e-mail messages, for example, using the keyboard 5116 in conjunction with the display 5110 and possibly the auxiliary I/O subsystem 5112. The auxiliary subsystem 5112 may include devices such as: a touch screen, mouse, track ball, infrared fingerprint detector, or a roller wheel with dynamic button pressing capability. The keyboard 5116 is preferably an alphanumeric keyboard and/or telephone-type keypad. However, other types of keyboards may also be used. A composed item may be transmitted over the wireless network 5105 through the communication subsystem 5104.

For voice communications, the overall operation of the mobile device 5100 is substantially similar, except that the received signals are output to the speaker 5118, and signals for transmission are generated by the microphone 5120. Alternative voice or audio I/O subsystems, such as a voice message recording subsystem, can also be implemented on the mobile device 5100. Although voice or audio signal output is accomplished primarily through the speaker 5118, the display 5110 can also be used to provide additional information such as the identity of a calling party, duration of a voice call, or other voice call related information.

Figure 52:
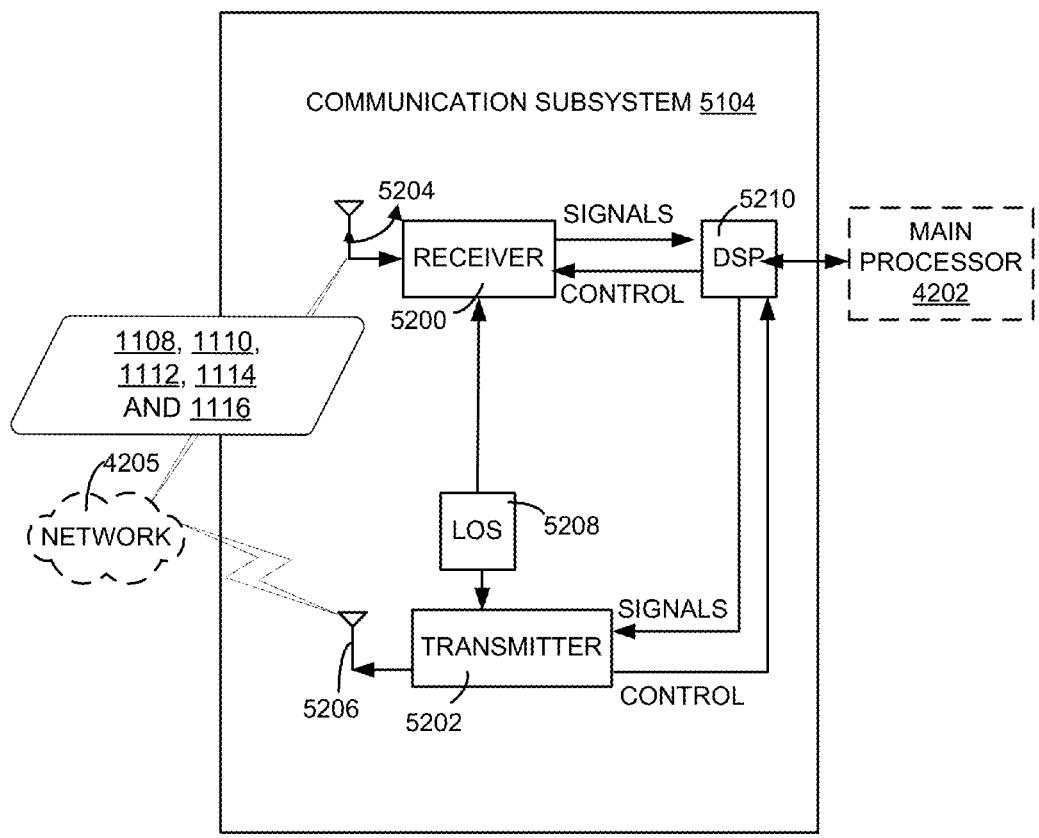
FIG. 52, a block diagram of the communication subsystem component is shown, according to an implementation.

Referring now to FIG. 52, a block diagram of the communication subsystem component 5104 is shown, according to an implementation. The communication subsystem 5104 includes a receiver 5200, a transmitter 5202, as well as associated components such as one or more embedded or internal antenna elements 5204 and 5206, Local Oscillators (LOS) 5208, and a processing module such as a Digital Signal Processor (DSP) 5210. The particular implementation of the communication subsystem 5104 is dependent upon the communication wireless network 5105 with which the mobile device 5100 is intended to operate. Thus, it should be understood that the implementation illustrated in FIG. 52 serves only as one example.

Signals received by the antenna 5204 through the wireless network 5105 are input to the receiver 5200, which may perform such common receiver functions as signal amplification, frequency down conversion, filtering, channel selection, and analog-to-digital (A/D) conversion. A/D conversion of a received signal allows more complex communication functions such as demodulation and decoding to be performed in the DSP 5210. In a similar manner, signals to be transmitted are processed, including modulation and encoding, by the DSP 5210. These DSP-processed signals are input to the transmitter 5202 for digital-to-analog (D/A) conversion, frequency up conversion, filtering, amplification and transmission over the wireless network 5105 via the antenna 5206. The DSP 5210 not only processes communication signals, but also provides for receiver and transmitter control. For example, the gains applied to communication signals in the receiver 5200 and the transmitter 5202 may be adaptively controlled through automatic gain control algorithms implemented in the DSP 5210.

The wireless link between the mobile device 5100 and the wireless network 5105 can contain one or more different channels, typically different RF channels, and associated protocols used between the mobile device 5100 and the wireless network 5105. An RF channel is a limited resource that must be conserved, typically due to limits in overall bandwidth and limited battery power of the mobile device 5100.

When the mobile device 5100 is fully operational, the transmitter 5202 is typically keyed or turned on only when it is transmitting to the wireless network 5105 and is otherwise turned off to conserve resources. Similarly, the receiver 5200 is periodically turned off to conserve power until the receiver 5200 is needed to receive signals or information (if at all) during designated time periods.

The configuration data 908, the diagnostic results 912 and the calibration results 916 is received by the communication subsystem 5104 from the wireless network 5105 through the antenna 5204 of the receiver 5200 and transferred to the DSP 5210 and to the main processor 5102.

FIG. 53 is a block diagram of a thermometer control computer 5300, according to an implementation. The thermometer control computer 5300 includes a processor (such as a Pentium III processor from Intel Corp. in this example) which includes dynamic and static ram and non-volatile program read-only-memory (not shown), operating memory 5304 (SDRAM in this example), communication ports 5306 (e.g., RS-232 5308 COM1/2 or Ethernet 5310), and a data acquisition circuit 5312 with analog inputs 5314 and analog outputs 5316.

In some implementations of the thermometer control computer 5300, the data acquisition circuit 5312 is also coupled to counter timer ports 5340 and watchdog timer ports 5342. In some implementations of the thermometer control computer 5300, an RS-232 port 5344 is coupled through a universal asynchronous receiver/transmitter (UART) 5346 to a bridge 5326.

In some implementations of the thermometer control computer 5300, the Ethernet port 5310 is coupled to the bus 5328 through an Ethernet controller 5350.

With proper digital amplifiers and analog signal conditioners, the thermometer control computer 5300 can be programmed to drive the display device 4202. The sensed temperatures can be received by thermal sensors 910 and 3912, the output of which, after passing through appropriate signal conditioners, can be read by the analog to digital converters that are part of the data acquisition circuit 5312. Thus the temperatures can be made adjusted for ambient temperature or the physical site of the human or animal that was examined for temperature on in as part of its decision-making software that acts to process and display sensed temperature.

FIG. 54 is a block diagram of a data acquisition circuit 5400 of a thermometer control computer, according to an implementation. The data acquisition circuit 5400 is one example of the data acquisition circuit 5312 in FIG. 53 above. Some implementations of the data acquisition circuit 5400 provide 16-bit A/D performance with input voltage capability up to +/−10V, and programmable input ranges.

The data acquisition circuit 5400 can include a bus 5402, such as a conventional PC/104 bus. The data acquisition circuit 5400 can be operably coupled to a controller chip 5404. Some implementations of the controller chip 5404 include an analog/digital first-in/first-out (FIFO) buffer 5406 that is operably coupled to controller logic 5408. In some implementations of the data acquisition circuit 5400, the FIFO 5406 receives signal data from and analog/digital converter (ADC) 5410, which exchanges signal data with a programmable gain amplifier 5412, which receives data from a multiplexer 5414, which receives signal data from analog inputs 5416.

In some implementations of the data acquisition circuit 5400, the controller logic 5408 sends signal data to the ADC 5410 and a digital/analog converter (DAC) 5418. The DAC 5418 sends signal data to analog outputs. The analog outputs, after proper amplification, can be used to modulate coolant valve actuator positions. In some implementations of the data acquisition circuit 5400, the controller logic 5408 receives signal data from an external trigger 5422.

In some implementations of the data acquisition circuit 5400, the controller chip 5404 includes a digital input/output (I/O) component 5438 that sends digital signal data to computer output ports.

In some implementations of the data acquisition circuit 5400, the controller logic 5408 sends signal data to the bus 5402 via a control line 5446 and an interrupt line 5448. In some implementations of the data acquisition circuit 5400, the controller logic 5408 exchanges signal data to the bus 5402 via a transceiver 5450.

Some implementations of the data acquisition circuit 5400 include 12-bit D/A channels, programmable digital I/O lines, and programmable counter/timers. Analog circuitry can be placed away from the high-speed digital logic to ensure low-noise performance for important applications. Some implementations of the data acquisition circuit 5400 are fully supported by operating systems that can include, but are not limited to, DOS™, Linux™, RTLinux™, QNX™, Windows 98/NT/2000/XP/CE™, Forth™, and VxWorks™ to simplify application development.

Figure 55:
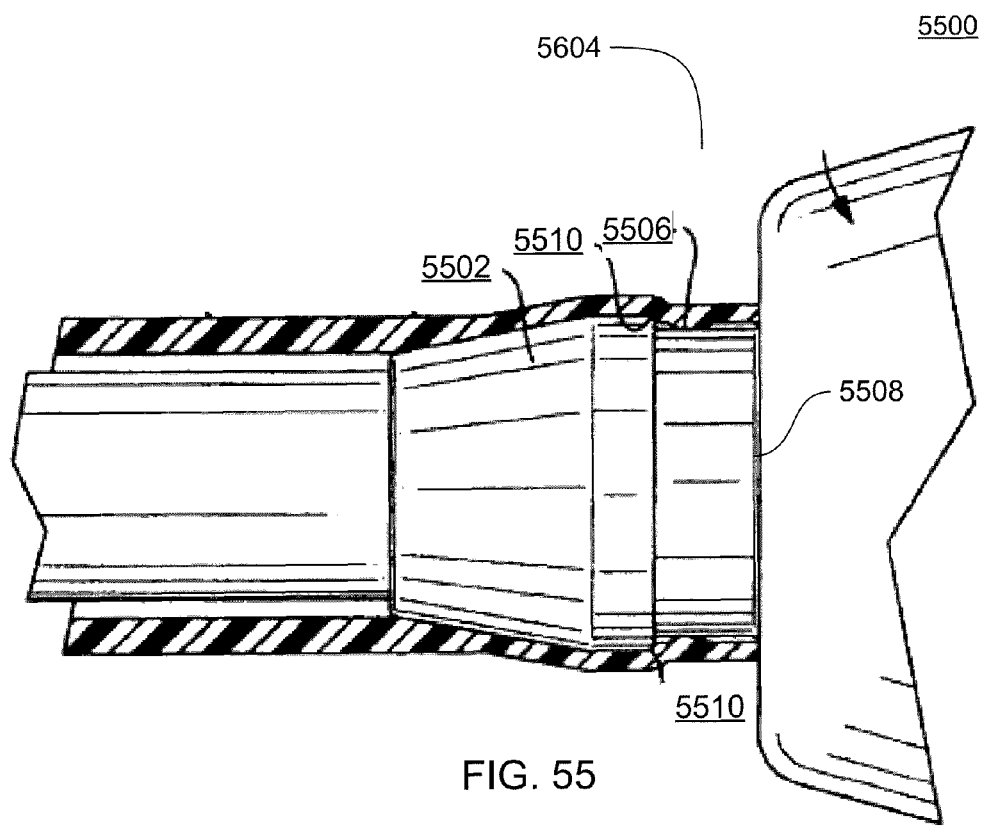
FIG. 55 is a partial side cross-section view of a probe cover and a probe, according to an implementation.
Figure 56:
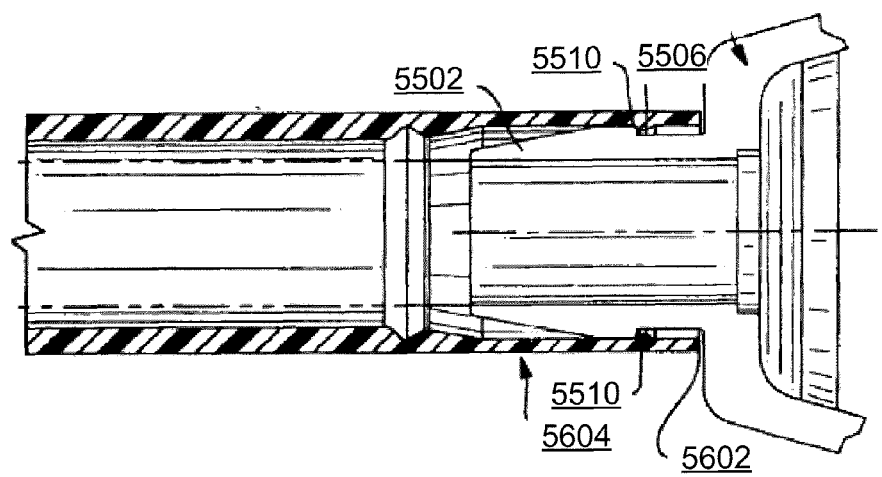
FIG. 56 is a partial side cross-section view of a probe cover prior to ejection from a probe, according to an implementation.

FIG. 55 is a partial side cross-section view of a probe cover and a probe 5500, according to an implementation FIG. 56 is a partial side cross-section view of a probe cover 5600 prior to ejection from a probe, according to an implementation The conical tympanic probe 100, the tapered tympanic probe 300, the conical tympanic probe 500 and the tapered tympanic probe 700 is a substantially cylindrical member that extends to a holding barb 5502 at a proximal end 5504 thereof. A thermometer that includes the conical tympanic probe 100, the tapered tympanic probe 300, the conical tympanic probe 500 and the tapered tympanic probe 700 further a handle (not shown) at the proximal or upper end 5504 of the probe in relation to the holding barb 5502, wherein the handle includes a depressible button (not shown) which permits the holding barb to move relative to the attached probe cover, effecting release thereof, as part of an ejection mechanism. The depression of the button (not shown) causes an attached probe cover to be pushed off of the probe by moving the stainless steel shaft forward, causing the attached probe cover to be pushed beyond the holding barb 5502. The probe cover is sized in terms of its length such that initial engagement of the probe cover with the conical tympanic probe 100, the tapered tympanic probe 300, the conical tympanic probe 500 and the tapered tympanic probe 700 causes the stainless steel shaft to be pushed rearwardly, causing the button (not shown) to be pushed outwardly from the handle (not shown).

As to the operation of the conical tympanic probe 100, the tapered tympanic probe 300, the conical tympanic probe 500 and the tapered tympanic probe 700, a disposable probe cover is placed onto the exterior of the probe. The probe cover, being a hollow elongated member, is constructed to overlay the elongate probe, including the holding barb 5502, so as to protect the probe from contamination. A retaining rib 5506 is caused to engage the holding barb 5502 and further due to the length differences between the shaft portion of the probe and the probe cover, engagement with same causes the shaft portion to be pushed rearwardly extending the button outwardly from the handle. The probe covers are manufactured with a substantially constant thickness in the proximal end that is being attached to the holding barb 5502.

The probe cover (e.g. 101 in FIG. 1-2, 301 in FIG. 3-4, 501 in FIG. 5-6 and 701 in FIG. 7-8) is an elongated hollow plastic member made from a low density polypropylene or other suitable material. The probe cover (e.g. 101 in FIG. 1-2, 301 in FIG. 3-4, 501 in FIG. 5-6 and 701 in FIG. 7-8) has an open proximal end 5508 and an opposing distal tip 5602. The probe cover (e.g. 101 in FIG. 1-2, 301 in FIG. 3-4, 501 in FIG. 5-6 and 701 in FIG. 7-8) is appropriately sized in terms of its overall dimensions to be fitted over a conical tympanic probe 100, the tapered tympanic probe 300, the conical tympanic probe 500 and the tapered tympanic probe 700.

The probe cover (e.g. 101 in FIG. 1-2, 301 in FIG. 3-4, 501 in FIG. 5-6 and 701 in FIG. 7-8) has a substantially constant wall thickness extending over substantially the majority of the axial portion of the probe cover probe cover (e.g. 101 in FIG. 1-2, 301 in FIG. 3-4, 501 in FIG. 5-6 and 701 in FIG. 7-8). A proximal attachment portion 5604 extends approximately 0.250 inches from the proximal end 5508 of the probe cover (e.g. 101 in FIG. 1-2, 301 in FIG. 3-4, 501 in FIG. 5-6 and 701 in FIG. 7-8), the attachment portion having a variable wall thickness as will be described below. The wall thickness across the major axial portion of the probe cover (e.g. 101 in FIG. 1-2, 301 in FIG. 3-4, 501 in FIG. 5-6 and 701 in FIG. 7-8) is approximately 0.022-0.028 inches between the distal tip 5602 of the probe cover and the proximal attachment portion 5604.

The interior wall thickness at the proximal attachment portion 5604 of the probe cover (e.g. 101 in FIG. 1-2, 301 in FIG. 3-4, 501 in FIG. 5-6 and 701 in FIG. 7-8) tapers inwardly from a first wall thickness of about 0.025 inches to a second wall thickness of about 0.010 inches, the wall thicknesses according to this implementation having a variability of about 0.002 inches. Immediately adjacent the proximal end 5508, the wall thickness is locally increased in order to provide an annular retaining rib 5506 that is used to engage the rear edge 5510 of the holding barb 5502 of the conical tympanic probe 100, the tapered tympanic probe 300, the conical tympanic probe 500 and the tapered tympanic probe 700.

The overall reduction in wall thickness in the proximal attachment portion 5604 permits the thinned portions of the herein described probe cover (e.g. 101 in FIG. 1-2, 301 in FIG. 3-4, 501 in FIG. 5-6 and 701 in FIG. 7-8) to elastically deform in a radial direction when mounted onto the holding barb 5502 of the conical tympanic probe 100, the tapered tympanic probe 300, the conical tympanic probe 500 and the tapered tympanic probe 700, wherein the resulting elastic deformation creates a storage of energy in the form of a created hoop stress component. Moreover, the thinned wall portion is structurally weakened, wherein the ejection mechanism of the conical tympanic probe 100, the tapered tympanic probe 300, the conical tympanic probe 500 and the tapered tympanic probe 700, when employed, ruptures the thinned wall portion.

In operation, the probe cover (e.g. 101 in FIG. 1-2, 301 in FIG. 3-4, 501 in FIG. 5-6 and 701 in FIG. 7-8) is fitted onto the conical tympanic probe 100, the tapered tympanic probe 300, the conical tympanic probe 500 and the tapered tympanic probe 700 wherein the proximal end 5508 and more particularly, the proximal attachment portion 5604 is elastically fitted over the holding barb 5502 when attached in which the retaining rib 5506 engages the rear edge 5510 of the barb and creates a spring force due to the elastic deformation that is created when the probe cover is attached. Following attachment of the probe cover (e.g. 101 in FIG. 1-2, 301 in FIG. 3-4, 501 in FIG. 5-6 and 701 in FIG. 7-8), a temperature measuring procedure can then be performed on the patient using the conical tympanic probe 100, the tapered tympanic probe 300, the conical tympanic probe 500 and the tapered tympanic probe 700 in accordance with known techniques.

In some implementations, wherein a retaining rib 5506 is also provided for engaging the rear edge 5510 of the holding barb 5502 of the conical tympanic probe 100, the tapered tympanic probe 300, the conical tympanic probe 500 and the tapered tympanic probe 700 wherein a thinned wall portion enables elastic deformation of the probe cover in the vicinity of the holding barb to create the desired stored energy upon attachment/engagement.

To initiate ejection, the user applies forward pressure to the ejection member of the probe by depression of the button (not shown), provided on the proximal end 5504 of the conical tympanic probe 100, the tapered tympanic probe 300, the conical tympanic probe 500 and the tapered tympanic probe 700. As a result, the connected ejection member, as well as the distally connected holding barb 5502, are each pushed laterally forward (toward the distal end of the probe). As the holding barb 5502 is moved laterally, the rear edge 5510 is also moved forward, thereby causing the retaining rib 5506 to disengage from the holding barb. This release further creates a release of the stored energy and the probe cover (e.g. 101 in FIG. 1-2, 301 in FIG. 3-4, 501 in FIG. 5-6 and 701 in FIG. 7-8) is thrust forward along the length of the conical tympanic probe 100, the tapered tympanic probe 300, the conical tympanic probe 500 and the tapered tympanic probe 700, thereby pushing the probe cover clear of the holding barb 5502 and enabling the probe cover to fall from the conical tympanic probe 100, the tapered tympanic probe 300, the conical tympanic probe 500 and the tapered tympanic probe 700. In addition, the release further ruptures at least a portion of the weakened wall portion, rendering the probe cover (e.g. 101 in FIG. 1-2, 301 in FIG. 3-4, 501 in FIG. 5-6 and 701 in FIG. 7-8) useless. The lubricious and hoop strength properties of the material of the probe cover assist in the ejection process by reducing friction (lubricity) and aiding ejection (hoop strength).

The creation of a weakened wall region ensures that the probe cover (e.g. 101 in FIG. 1-2, 301 in FIG. 3-4, 501 in FIG. 5-6 and 701 in FIG. 7-8) is rendered useless upon ejection. Therefore, the probe cover (e.g. 101 in FIG. 1-2, 301 in FIG. 3-4, 501 in FIG. 5-6 and 701 in FIG. 7-8) cannot be reused, inadvertently or otherwise. Second, the storage of energy within the probe cover (e.g. 101 in FIG. 1-2, 301 in FIG. 3-4, 501 in FIG. 5-6 and 701 in FIG. 7-8) of the present implementation built up during the installation of the probe cover to the probe due to the thinned wall thickness of the proximal attachment portion 5604 ensures that the probe cover (e.g. 101 in FIG. 1-2, 301 in FIG. 3-4, 501 in FIG. 5-6 and 701 in FIG. 7-8) can be removed successfully without user intervention, other than that required to initially impart a lateral force on the probe cover to initiate ejection/removal. The spring force ensures that the probe cover (e.g. 101 in FIG. 1-2, 301 in FIG. 3-4, 501 in FIG. 5-6 and 701 in FIG. 7-8) is successfully ejected without requiring the user to have to overly handle the probe cover.

As noted by the preceding implementation, varying the wall thickness of the probe cover is not limited to the proximal end 5508 to aid in the removal of the probe cover (e.g. 101 in FIG. 1-2, 301 in FIG. 3-4, 501 in FIG. 5-6 and 701 in FIGS. 7-8) and further to disable the probe cover from re-use. Further enhanced benefits are provided by also reducing the wall thickness at the distal tip 5602 relative to the remainder of the probe cover.

Conclusion

A probe cover that has a geometry to fit an ear canal and an infrared parabolic condenser inside the probe cover. A technical effect of the probe cover is higher signal strength to an IR sensor. Although specific implementations are illustrated and described herein, it will be appreciated by those of ordinary skill in the art that any arrangement which is calculated to achieve the same purpose may be substituted for the specific implementations shown. This application is intended to cover any adaptations or variations.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future non-contact temperature sensing devices, different temperature sensing devices and tympanic probe covers.

The terminology used in this application meant to include all temperature sensors, processors and user environments and alternate technologies which provide the same functionality as described herein.

The invention claimed is:

1. A tympanic probe cover comprising:
   a probe cover body that has a geometry to fit an ear canal, the probe cover body having an upper free frontal end, the upper free frontal end of the probe cover body having a tip, the probe cover body does not include any further structures;
   a probe cover window at the upper free frontal end of the probe cover body that closes off the upper free frontal end of the probe cover body, probe cover window being attached to the probe cover body by a weaving, the probe cover window being transparent to infrared radiation at a radiation range relevant for human temperature measurement;
   a probe cover base that is attached at a bottom of the probe cover body that is an opposite end of the upper free frontal end of the probe cover body; and
   an infrared parabolic condenser inside the tip of the upper free frontal end of the probe cover body.

2. The tympanic probe cover of claim 1, wherein the probe cover body further comprises:
   a tapered probe cover body.

3. The tympanic probe cover of claim 1, wherein the probe cover body further comprises:
   a conical probe cover body.

4. A tympanic probe cover comprising:
   a probe cover body that has a geometry to fit an ear canal, the probe cover body having an upper free frontal end, the probe cover body does not include any further structures;
   a probe cover window at the upper free frontal end of the probe cover body that closes off the upper free frontal end of the probe cover body, the probe cover window being transparent to infrared radiation at a radiation range relevant for human temperature measurement;
   a probe cover base that is attached at a bottom of the probe cover body that is an opposite end of the upper free frontal end of the probe cover body; and
   an infrared parabolic condenser inside the probe cover body.

5. The tympanic probe cover of claim 4, wherein the probe cover window being attached to the probe cover body by a weaving.

6. The tympanic probe cover of claim 4, wherein the upper free frontal end of the probe cover body further comprises:
   a tip.

7. The tympanic probe cover of claim 6, wherein infrared parabolic condenser is inside the tip of the upper free frontal end of the probe cover body.

8. The tympanic probe cover of claim 4, wherein the probe cover body further comprises:
a tapered probe cover body.

9. The tympanic probe cover of claim 4, wherein the probe cover body further comprises:
a conical probe cover body.

10. A tympanic probe cover comprising:
a probe cover body that has a geometry to fit an ear canal, the probe cover body having an upper free frontal end, the probe cover body does not include any further structures;
a probe cover window at the upper free frontal end of the probe cover body that closes off the upper free frontal end of the probe cover body, the probe cover window being transparent to infrared radiation at a radiation range relevant for human temperature measurement; and
an infrared parabolic condenser inside the probe cover body.

11. The tympanic probe cover of claim 10, wherein the probe cover window being attached to the probe cover body by a weaving.

12. The tympanic probe cover of claim 10, wherein the upper free frontal end of the probe cover body further comprises:
a tip.

13. The tympanic probe cover of claim 12, wherein infrared parabolic condenser is inside the tip of the upper free frontal end of the probe cover body.

14. The tympanic probe cover of claim 10, wherein the probe cover body further comprises:
a tapered probe cover body.

15. The tympanic probe cover of claim 10, wherein the probe cover body further comprises:
a conical probe cover body.

16. The tympanic probe cover of claim 10, further comprising:
a probe cover base that is attached at a bottom of the probe cover body, wherein the bottom is an opposite end of the upper free frontal end of the probe cover body.

* * * * *